United States Patent [19]

Zimmerman

[11] Patent Number: 5,356,862

[45] Date of Patent: Oct. 18, 1994

[54] HERBICIDAL SULFONYLUREAS

[75] Inventor: William T. Zimmerman, Landenberg, Pa.

[73] Assignee: E. I. Du Pont de Nemours and Company, Wimington, Del.

[21] Appl. No.: 915,838

[22] PCT Filed: Jan. 9, 1991

[86] PCT No.: PCT/US91/00023

§ 371 Date: Jul. 22, 1992

§ 102(e) Date: Jul. 22, 1992

[87] PCT Pub. No.: WO91/10668

PCT Pub. Date: Jul. 25, 1991

Related U.S. Application Data

[63] Continuation-in-part of Ser. No. 468,283, Jan. 22, 1990.

[51] Int. Cl.$^5$ .................. A01N 43/54; C07D 403/12; C07D 417/12; C07D 413/12
[52] U.S. Cl. ........................ 504/215; 544/105; 544/47; 544/48; 544/295; 544/101; 544/32; 544/2; 544/10; 544/9; 544/320; 544/321; 544/324; 544/323; 544/331; 544/332
[58] Field of Search .................. 504/215; 544/105, 47, 544/48, 295, 101, 32, 2, 10, 9, 320, 321, 324, 323, 331, 332

[56] References Cited

U.S. PATENT DOCUMENTS

| | | | |
|---|---|---|---|
| 4,368,067 | 1/1983 | Budzinski et al. | 71/92 |
| 4,473,394 | 9/1984 | Budzinski et al. | 71/93 |
| 4,549,898 | 10/1985 | Bohner et al. | 71/90 |
| 4,557,752 | 12/1985 | Budzinski et al. | 71/92 |
| 4,622,062 | 11/1986 | Wexler | 71/90 |
| 4,671,817 | 6/1987 | Wexler | 71/91 |
| 4,737,184 | 4/1988 | Pasteris | 71/90 |
| 4,756,742 | 7/1988 | Thompson | 71/90 |
| 4,764,610 | 8/1988 | Zimmerman | 71/92 |
| 4,921,527 | 5/1990 | Tseng | 71/90 |

FOREIGN PATENT DOCUMENTS 238070 9/1987 European Pat. Off.

Primary Examiner—John M. Ford

[57] ABSTRACT

The invention relates to herbicidal sulfonylurea compounds, agriculturally suitable compositions thereof and a method for their use as general or selective preemergent or postemergent herbicides or plant growth regulants.

33 Claims, No Drawings

HERBICIDAL SULFONYLUREAS

CROSS-REFERENCE TO RELATED APPLICATION

This is a continuation-in-part of U.S. Ser. No. 07/468,283 filed Jan. 22, 1990.

BACKGROUND OF THE INVENTION

This invention relates to certain herbicidal sulfonylureas, agriculturally suitable compositions thereof and a method for their use as general or selective preemergent or postemergent herbicides or as plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

EP-A-238,070 discloses herbicidal sulfonylureas of the general formula

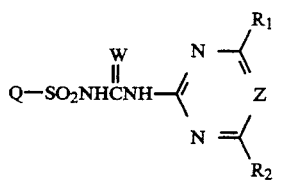

wherein:
Q is a condensed heterocyclic group having an N atom in the bridgehead, which may be substituted.

SUMMARY OF THE INVENTION

Now new compounds have been found that are pre-emergence and/or postemergence herbicides or plant growth regulants. Accordingly, the compounds of the invention are compounds of the formula

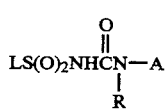

wherein:
L is

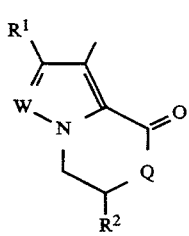

L-1

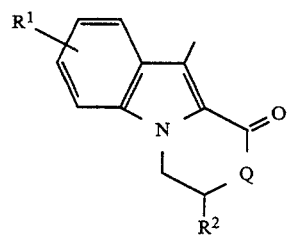

L-2

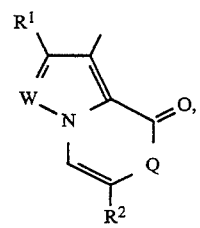

L-3

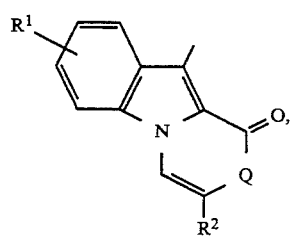

L-4

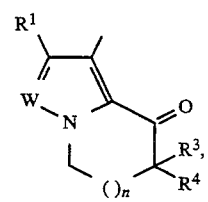

L-5

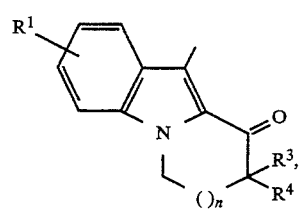

L-6

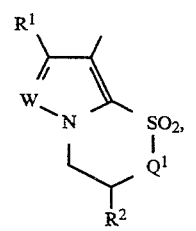

L-7

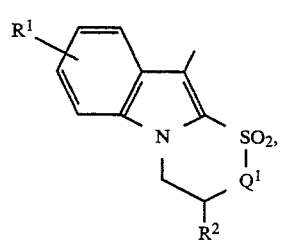

L-8

-continued

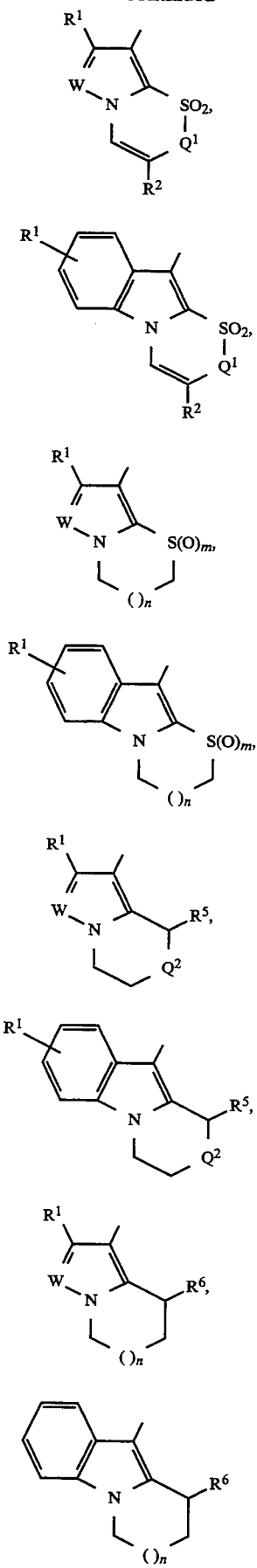

Q is O, S or $NR^8$;
$Q^1$ is O or $NR^8$;
$Q^2$ is O, S or $NCH_3$;
R is H or $CH_3$;
$R^1$ is H, $CH_3$, Cl or Br;
$R^2$ is H or $CH_3$;
$R^3$ is H, $CH_3$, F, Cl or Br;
$R^4$ is H, $CH_3$, F, Cl or Br;
$R^5$ is H or $C_1$–$C_3$ alkyl;
$R^6$ is H, $C_1$–$C_3$ alkyl, $C_1$–$C_3$ alkoxy, F, Cl, ($C_1$–$C_2$ alkyl)carbonyloxy or $C_1$–$C_2$ alkylsulfonyloxy;
$R^7$ is $CO_2R^9$, $CO_2NR^{10}R^{11}$, $S(O)_2NR^{10}R^{11}$ or $S(O)_2R^{12}$;
$R^8$ is H, $C_1$–$C_4$ alkyl, $C_1$–$C_4$ haloalkyl, allyl, propargyl or $C_2$–$C_4$ alkoxyalkyl;
$R^9$ is $C_1$–$C_4$ alkyl;
$R^{10}$ is H or $C_1$–$C_2$ alkyl;
$R^{11}$ is H or $C_1$–$C_2$ alkyl;
$R^{12}$ is $C_1$–$C_3$ alkyl;
W is $CR^{13}$ or N;
$R^{13}$ is H, $CH_3$, Cl or Br;
m is 0, 1 or 2;
n is 0 or 1;

A is 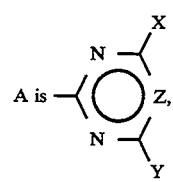 A-1

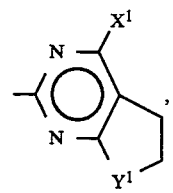 A-2

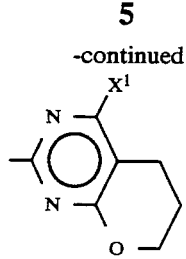 A-3

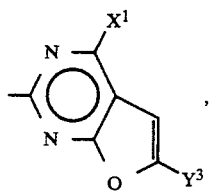 A-4

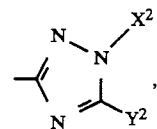 A-5

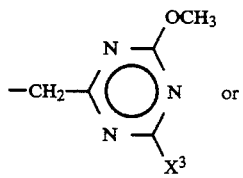 A-6 or

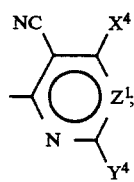 A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido, cyano,

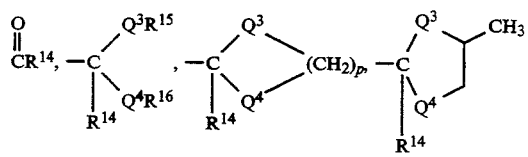

or N(OCH$_3$)CH$_3$;
p is 2 or 3;
$Q^3$ and $Q^4$ are independently O or S;
$R^{14}$ is H or $C_1$-$C_3$ alkyl;
$R^{15}$ and $R^{16}$ are independently $C_1$-$C_3$ alkyl;
Z is CH, N, CCH$_3$, CC$_2$H$_5$, CCl or CBr;
$Z^1$ is CH or N;
$Y^1$ is O or CH$_2$;
$X^1$ is CH$_3$, OCH$_3$, OCH$_2$CH$_3$ or OCF$_2$H;
$X^2$ is CH$_3$, CH$_2$CH$_3$ or CH$_2$CF$_3$;

$Y^2$ is OCH$_3$, OCH$_2$CH$_3$, SCH$_3$, SCH$_2$CH$_3$, CH$_3$ or CH$_2$CH$_3$;
$X^3$ is CH$_3$ or OCH$_3$;
$Y^3$ is H or CH$_3$;
$X^4$ is CH$_3$, OCH$_3$, OCH$_2$CH$_3$, CH$_2$OCH$_3$ or Cl; and
$Y^4$ is CH$_3$, OCH$_3$, OCH$_2$CH$_3$ or Cl;
and their agriculturally suitable salts;
provided that 1) when X is halogen, then Z is CH and Y is OCH$_3$, OCH$_2$CH$_3$, NH$_2$, NHCH$_3$, N(CH$_3$)$_2$, OCF$_2$H, OCF$_2$Br or N(OCH$_3$)CH$_3$;
2) when X or Y is $C_1$ haloalkoxy, then Z is CH; and
3) $X^4$ and $Y^4$ are not simultaneously Cl.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyloxy isomers.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include CH$_2$CH$_2$F, CF$_2$CF$_3$ and CH$_2$CHFCl.

The total number of carbon atoms in a substituent group is indicated by the $C_i$-$C_j$ prefix where i and j are numbers from 1 to 5. For example, $C_1$-$C_3$ alkylsulfonyl would designate methylsulfonyl through propylsulfonyl and $C_2$ alkoxyalkoxy would designate OCH$_2$OCH$_3$.

Compounds of the invention preferred for reasons of increased ease of synthesis and/or greater herbicidal efficacy are:

1. Compounds of Formula I where
   A is A-1
   X is $C_1$-$C_2$ alkyl, $C_1$-$C_2$ alkoxy, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
   Y is H, $C_1$-$C_2$ alkyl, $C_1$-$C_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$,

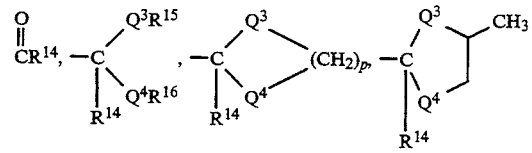

OCF$_2$H, SCF$_2$H, cyclopropyl, C≡CH or C≡CCH$_3$;
$R^{14}$ is H or CH$_3$;

$R^{15}$ and $R^{16}$ are independently $CH_3$ or $CH_2CH_3$;
Z is CH or N; and
R is H.
2. Compounds of Preferred 1 wherein L is L-1, L-2, L-3, L-7, L-8 or L-9.
3. Compounds of Preferred 2 where $R^8$ is H, $C_1$-$C_3$ alkyl or allyl.
4. Compounds of Preferred 3 where
Z is CH;
X is $CH_3$, $OCH_3$, $OCH_2CH_3$, Cl or $OCF_2H$; and
Y is $CH_3$, $OCH_3$, $CH(OCH_3)_2$ or $OCF_2H$.
5. Compounds of Preferred 4 where
L is L-1; and
W is CH.
6. Compounds of Preferred 4 where
L is L-2.
7. Compounds of Preferred 4 where
L is L-7.

Compounds of the invention specifically preferred for reasons of greatest ease of synthesis and/or greatest herbicidal efficacy are:
3,4-dihydro-N-[[(4-methoxy-6-methyl-2-pyrimidin-2-yl)amino]carbonyl]-1-oxo-1H-[1,4]-oxazine[4,3-a]indole-10-sulfonamide;
3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide;
N-[[(4,6-dimethoxy-2-pyrimidinyl)amino]carbonyl]-3-4-dihydro-2H-pyrrolo[1,2-e][1,2,5]thiadiazine-8-sulfonamide, 1,1-dioxide;
N-[[(4,6-dimethoxy-2-pyrimidinyl)amino]carbonyl]-3,4-dihydro-2-methyl-2H-pyrazolo[1,5-e][1,2,5]thiadiazine-8-sulfonamide, 1,1-dioxide.

This invention also comprises novel compounds, such as the pyrrolesulfonamides of Formulas II and III, useful as intermediates to the compounds of Formula I.

$$\underset{H}{\underset{|}{N}}\diagdown \diagup SO_2NHR^{17} \qquad II$$

wherein
$R^{17}$ is H or $C(CH_3)_3$; and $LSO_2NH_2$ III
wherein
L is as defined above.

The compounds of this invention are active preemergent and postemergent herbicides and plant growth regulants. Some are especially useful for selective control of grass weeds in broad leaf crops such as cotton and soybeans.

DETAILED DESCRIPTION OF THE INVENTION SYNTHESIS

Compounds of the Invention

The sulfonylureas of Formula I may be prepared by a number of methods. These methods are described below, along with the appropriate references for greater detail.

Equation 1

$$\underset{2}{RNHA} + \underset{3}{LSO_2NCO} \longrightarrow I$$

One method of synthesis of sulfonylureas of Formula I is depicted in Equation 1 wherein R, A, and L are as defined above. A sulfonylisocyanate of Formula 3 is contacted with a heterocyclic amine of Formula 2 in an inert solvent to afford sulfonylurea of Formula I. Reaction time necessary can vary from several minutes to 24 hours or more, and temperature is preferably in the range of 20° to 80° C. Useful solvents for this reaction include aprotic inert solvents such as acetonitrile, dichloromethane, etc.

U.S. Pat. Nos. 4,127,405, 4,257,802 and 4,221,585 disclose this equation and are herein incorporated by reference.

Equation 2

$$\underset{4}{LSO_2NH_2} + \underset{5}{R^{18}O\overset{O}{\overset{\|}{C}}-NRA} \xrightarrow{R_3^{18}Al} I$$

Another method of synthesis of compounds of Formula I is depicted in Equation 2 wherein A, R, and L are as defined previously and $R^{18}$ is lower alkyl such as methyl or ethyl and so on. In this reaction, a sulfonamide of Formula 4 is contacted with an alkyl carbamate of Formula 5 in the presence of a trialkylaluminum in an inert solvent such as dichloromethane, 1,2-dichloroethane, etc., and subsequently treated with aqueous acid to afford sulfonylureas of Formula I. This reaction is taught in EP-A-83,975 (published Jul. 20, 1983).

Equation 3

$$\underset{4}{L-SO_2NH_2} + \underset{6}{ArO\overset{O}{\overset{\|}{C}}NRA} \xrightarrow{Base} I$$

A third method of preparation for herbicides of Formula I is depicted in Equation 3 wherein A, R, and L are as defined previously, and Ar represents an aryl group, for example a phenyl or substituted phenyl group. In this reaction, a sulfonamide of Formula 4 is contacted with an aryl carbamate of Formula 6 and a base such as 1,8-diazabicyclo[5.4.0]undec-7-ene (DBU) in an inert solvent such as acetonitrile or p-dioxane, and subsequently treated with aqueous acid to afford sulfonylureas of Formula I. The reaction is taught in EP-A-44,807, and EP-A-85,028.

Compounds of Formula I are generally best prepared by the procedure outlined in Equation 3. The methods of Equations 1 and 2 may, in many cases, be equally well employed to prepare compounds of Formula I.

Intermediate Compounds

Heterocyclic sulfonyl isocyanates of Formula 3 may be prepared by procedures taught in U.S. Pat. No. 4,127,405.

Heterocyclic carbamates of Formula 5 are prepared by procedures taught in EP-A-83,975. The heterocyclic carbamates of Formula 6 may be prepared by procedures taught in EP-A-44,807, EP-A-72,347, EP-A-173,498, U.S. Pat. No. 4,666,506, and references cited therein.

The sulfonamides 4 of this invention may be prepared in a variety of ways, some of which are described in Equations 4 through 13 and Equation 15.

Precursors to sulfonamides of Formula 4 where L contains a pyrrole or pyrazole ring (L-1, L-3, L-5, L-7, L-9, L-11, L-13, L-15, L-18) are depicted in Formula 7. The bicyclic fused ring sulfonamides of Formula 4 may be synthesized from these precursors, where $R^{19}$ is a suitable protecting group such as tert-alkyl or trialkylsilyl, by a variety of methods, some of which are described in Equations 4 through 13.

Equation 4

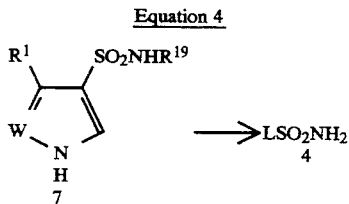

Similarly, precursors to sulfonamides of Formula 4 where L contains an indole ring system (L-2, L-4, L-6, L-8, L-10, L-12, L-14, L-16, L-19) are indole-3-sulfonamides of Formula 8, where $R^{19}$ is a suitable protecting group as defined above.

Equation 5

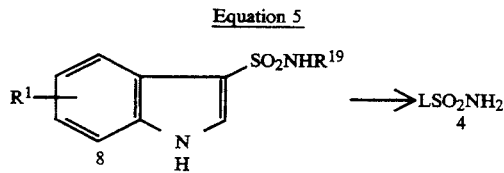

The methods that will be described for the conversion of sulfonamides of Formula 7 to bicyclic sulfonamides of Formula 4 are equally applicable for the conversion of indole-3-sulfonamides 8 to tricyclic sulfonamides of Formula 4; therefore, only the transformations of 7 will be outlined below.

Sulfonamides of Formula 4 where L is L-1 and $R^{19}$, $R^2$ and Q are as previously defined, $X^5$ is a suitable leaving group such as chloro, bromo, iodo, alkyl- or arylsulfonate, and $R^{20}$ is a suitable protecting group such as trialkylsilyl, tetrahydropyran-2-yl, may be prepared as outlined in Equation 6.

Equation 6

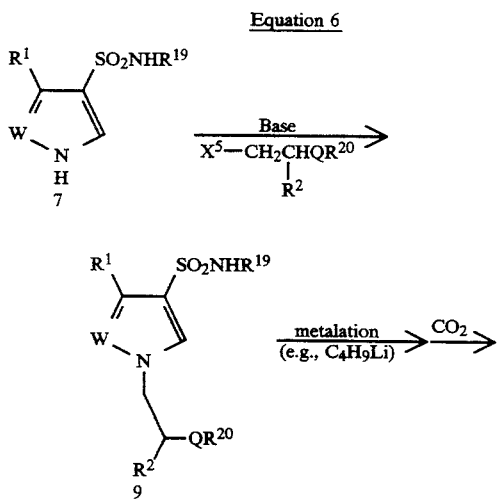

-continued
Equation 6

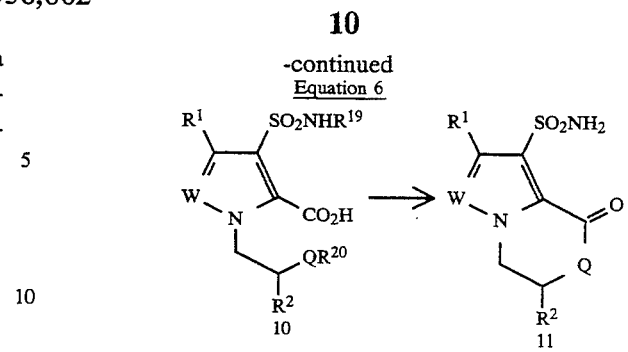

Sulfonamide 7 is treated with a base such as an alkali metal alkoxide, hydride or tertiary amine and an appropriate electrophilic reagent as shown in an inert solvent, preferably a polar aprotic solvent such as dimethylformamide (DMF) to afford intermediate 9. In the case where Q is oxygen, the electrophilic reagent may also be ethylene oxide or propylene oxide to afford sulfonamides 9 where $QR^{20}$ is OH. Sulfonamide 9 is then metalated on carbon using an excess of organometallic base, preferably an organolithium reagent such as n-butyllithium in an inert solvent such as diethyl ether or tetrahydrofuran (THF), under anhydrous conditions, followed by quenching with carbon dioxide to afford sulfonamides 10. The protecting groups $R^{20}$ are then removed by appropriate methods known to one skilled in the art. The resultant sulfonamides are then cyclized under dehydrating conditions, for example by heating in an aprotic solvent with acid catalysis and removal of water by azeotropic distillation.

Sulfonamides of Formula 4 where L is L-3 or L-9 may be prepared from corresponding sulfonamides of Formula 4 where L is L-1 or L-7 by known methods of dehydrogenation such as heating in a suitable inert solvent with dehydrogenating agents such as palladium on carbon or manganese dioxide. Additionally, sulfonamides of Formula 4 where L is L-3 and Q is O or S may be prepared from the corresponding acetals or ketals 12 as depicted in Equation 7, wherein $R^1$, $R^{19}$, and $X^5$ are as defined previously and $R^{21}$ is lower alkyl or the two $QR^{21}$ groups may be taken together to form a cyclic ketal such as 1,3-dioxolane or 1,3-dioxane ring.

Equation 7

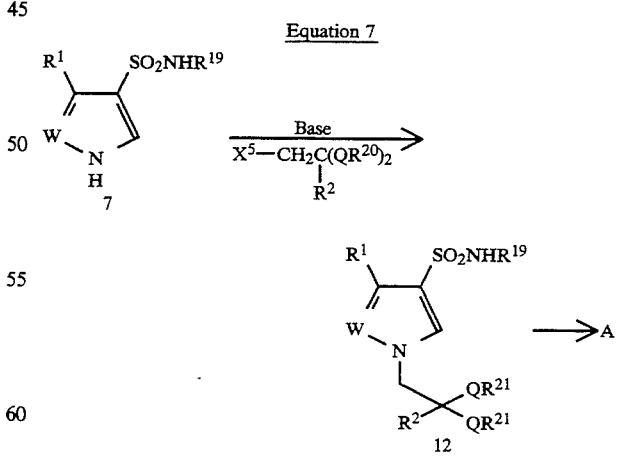

Subsequent metalation, quenching with carbon dioxide, and acid catalyzed cyclization as described above for Equation 6, afford sulfonamides of Formula 4 where L is L-3.

Preparation of sulfonamides 4 where L is L-5 may be accomplished by a similar sequence of reactions to that of Equation 6 and is outlined in Equation 8, wherein $X^5$, $R^{19}$, $R^{21}$, n and $R^1$ are as previously defined, $R^3$ and $R^4$ are H, F, or $CH_3$, and $Q^5$ is O or $NCH_3$.

Equation 8

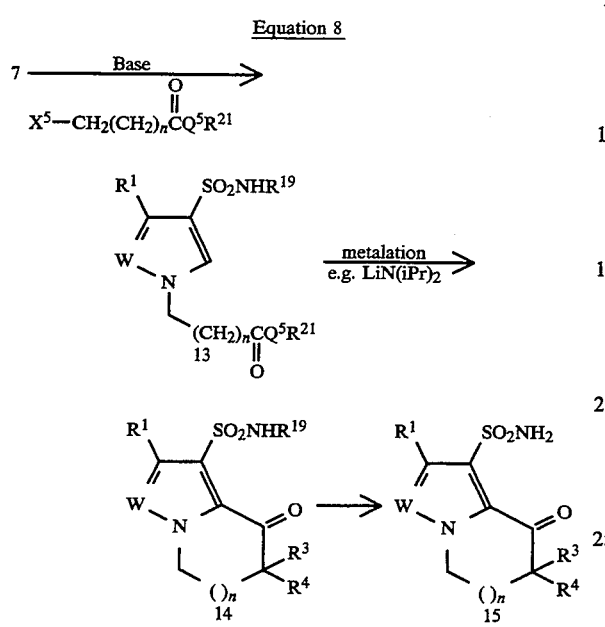

Sulfonamide 7 is treated with base as described above and a suitable electrophilic reagent to afford the carboxylic acid derivative 13. Metalation with a suitable base taken in at least two-fold excess relative to 13 results in cyclization to 14 after aqueous work-up. Protecting group removal affords sulfonamides of Formula 15. Sulfonamides 15 where $R^3$ and/or $R^4$ is chloro or bromo may be prepared from the corresponding ketones 15 where $R^3$ and/or $R^4$ is hydrogen by standard halogenation reactions known to one skilled in the art.

Unsaturated ketone sulfonamides 4 where L is L-18 or L-19 can be prepared from the corresponding saturated ketone sulfonamide intermediates 4 where L is L-5 or L-6 respectively using a variety of standard oxidation methods known in the literature; for example, by the chlorination, dehydrochlorination sequence described in "Organic Syntheses" Coll. Vol. IV, p. 162 (1963, John Wiley).

Sulfonamides of Formula 4 where L is L-7 may be prepared as outlined in Equation 9, wherein $R^1$, $R^2$, $R^{19}$ and $Q^1$ are as previously defined, and $R^{22}$ is a trialkylsilyl protecting group.

Equation 9

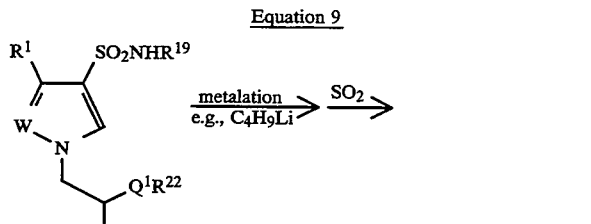

Equation 9 -continued

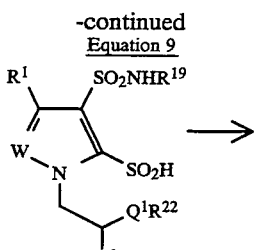

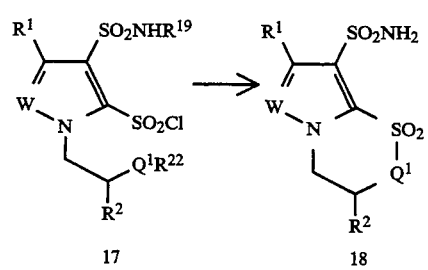

Metalation of sulfonamide 9 as described earlier in Equation 6, followed by quenching with sulfur dioxide affords sulfinic acid derivative 16. This intermediate may then be oxidized to sulfonyl chloride 17 using any of a variety of chlorinating reagents such as N-chlorosuccinimide, sodium hypochlorite, chlorine and the like. Protecting group removal induces cyclization to sulfonamides 18.

Preparation of sulfonamides 4 where L is L-11 may be achieved through the sequence outlined in Equation 10, wherein $R^1$, $R^{19}$, $X^5$ and W are as previously defined.

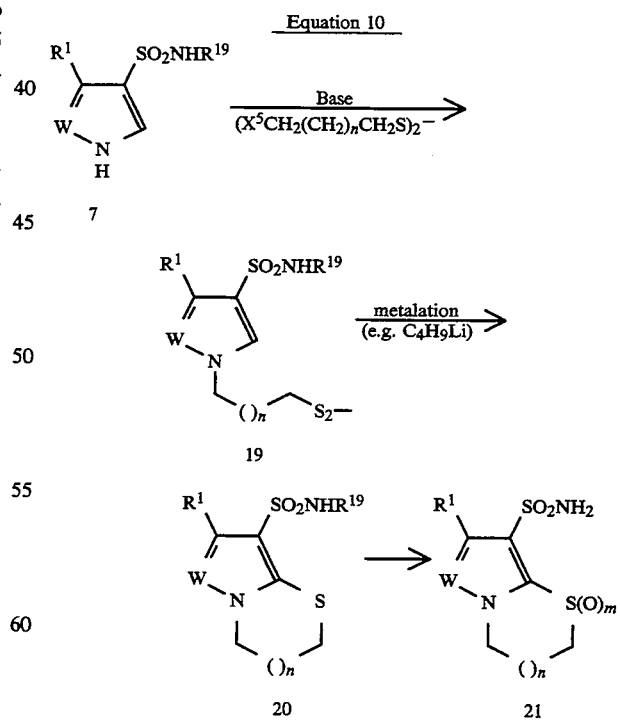

Sulfonamide of Formula 7 may be alkylated on nitrogen with a suitable electrophilic reagent containing a disulfide using conditions described in Equation 6 to afford intermediates 19. Metalation of 19 results in cyclization to cyclic sulfide 20 which can then be further oxidized with a suitable oxidant such as a peroxy acid or hydrogen peroxide to sulfoxides (m=1) or sulfones (m=2). Sulfonamide protecting group removal affords bicyclic sulfonamides 21.

The preparation of sulfonamides of Formula 4 wherein L is L-13 is depicted in Equation 11, wherein $R^1$, $R^5$, $R^{19}$, $R^{20}$, $Q^2$, and W are as previously defined.

Equation 11

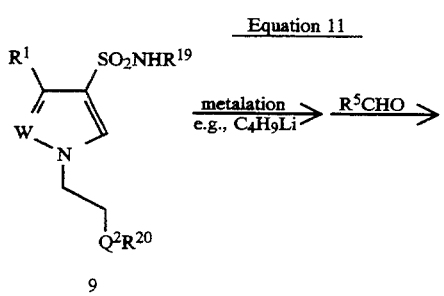

9

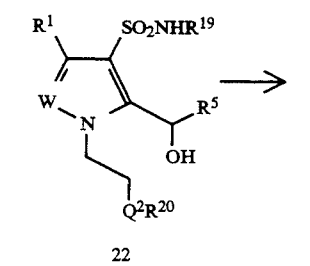

22

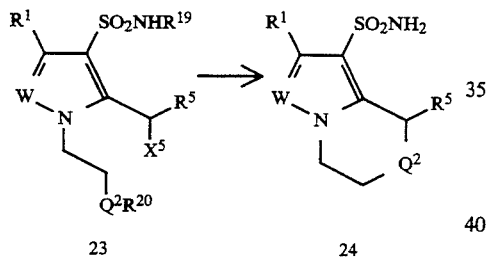

23  24

Metalation of 9 as described above, followed by quenching with an aldehyde, $R^5CHO$, affords alcohols 22. This alcohol is converted to a leaving group, $X^5$, such as halogen, or sulfonate, using standard methods. Removal of protecting group $R^{20}$, followed by treatment with base, as needed, induces cyclization to sulfonamides 24.

Sulfonamides of Formula 4 where L is L-15 may be prepared as outlined in Equation 12, wherein $R^{19}$ is tert-alkyl, $R^6$ is H or alkyl, and $R^{22}$ is a trialkylsilyl protecting group.

Equation 12

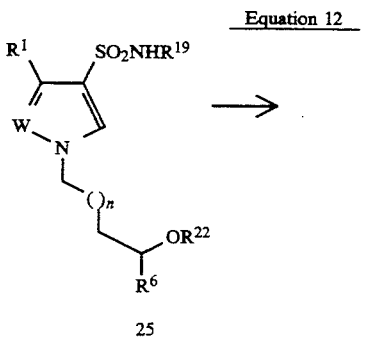

25

-continued
Equation 12

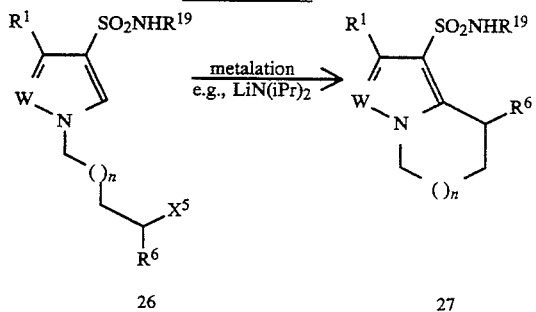

26  27

Silyl protecting group $R^{22}$ may be removed from 25 using fluoride in some form, then the resulting alcohol is converted to a suitable leaving group $X^5$, described above. Metalation of intermediate 26 affords bicyclic sulfonamide 27.

Alternatively, for sulfonamides of Formula 4 where L is L-15, and $R^6$ is as described in the Summary, the methods depicted in Equation 13 may be used.

Equation 13

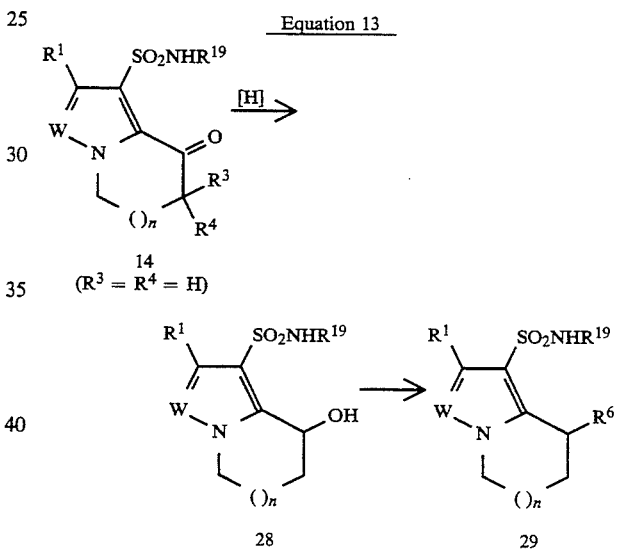

28  29

The ketone 14, wherein $R^3=R^4=H$, described in Equation 8 can be further treated with reducing agents such as borohydrides, aluminum hydrides and the like to afford the corresponding alcohols 28. Conversion of this alcohol to a variety of derivatives such as halides, ethers, esters, sulfonates as encompassed by $R^6$ may then be achieved by standard methods widely known in the art.

Pyrrole-3-sulfonamide precursors 7 wherein W=CH, $R^1$=H and $R^{19}$ is a suitable protecting group as defined above are available from the corresponding bromo pyrrole 30 as depicted in Equation 14, wherein $R^{23}$ is lower alkyl, such as isopropyl.

Equation 14

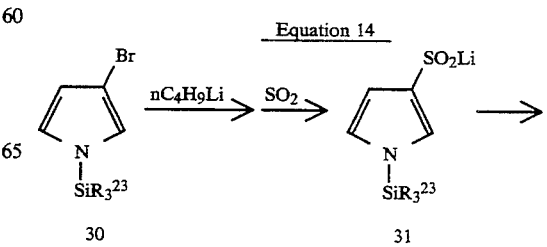

30  31

-continued
Equation 14

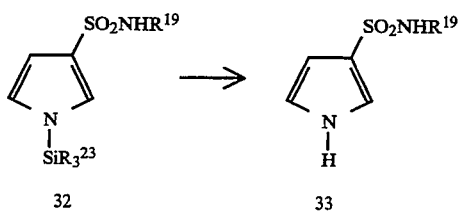

N-silyl-protected pyrrole 30, where $R^{23}$ is preferably an isopropyl group, is treated with an alkyllithium reagent such as n-butyllithium as described in Chem. Ber., Vol. 122, p. 169 (1989), and references cited therein. The resultant metalated species is treated with sulfur dioxide to afford sulfinate salt 31 which is then converted to sulfonamide 32 by any of a number of known methods, for example, treatment with N-chlorosuccinimide followed by amination with an appropriate primary amine as disclosed in U.S. Pat. No. 4,481,029. The N-silyl group is then removed, most conveniently with an alkali fluoride or quaternary ammonium fluoride salt, to afford pyrrole-3-sulfonamide 33 (equivalent to Formula 7 wherein $R^1$=H, W=CH). Additional derivatives of Formula 7 where $R^1$ is other than H, and W is $CR^{13}$ (where $R^{13} \neq H$) may be prepared by analogous methods. In sulfonamides of Formula 4 in the pyrrole and pyrazole series, where $R^1$ and/or $R^2$ is chloro or bromo, it may be more practical to introduce the halogens via a halogenation reaction on the corresponding unsubstituted bicyclic sulfonamides.

Pyrrole-2-sulfonamides where L is L-17 are available from precursors 35 as depicted in Equation 15, wherein $R^{19}$, $R^{20}$, $R^{23}$, $X^5$, and $R^7$ are as defined above, and $R^9$ is t-butyl.

Pyrrole derivatives 35 are available from the 3-bromo derivative 30 as described in Equation 14, using the appropriate electrophilic reagent in place of sulfur dioxide that would be apparent to one skilled in the art. N-Alkylation followed by metalation, sulfur dioxide treatment, and conversion of the sulfinate to a sulfonamide 37 proceeds by methods described above, for example, in Equations 6 and 9. Subsequent conversion of 37 to 38 where $X^5$ is a leaving group such as a sulfonate ester, followed by metalation analogous to that described in Equation 12, affords the bicyclic pyrrole-2-sulfonamides 39.

In the case where $R^7$ is an ester functionality, esters in which $R^9$ is other than t-butyl may be prepared from the t-butyl ester by heating 39 in the appropriate alcohol solvent with acid catalysis to effect a transesterification to sulfonamides 39 wherein $R^9$ is $C_1$-$C_4$ alkyl.

Indole-3-sulfonamide precursors 40 are available via the sequence outlined in Equation 16, wherein $R^1$ and $R^{19}$ are as previously defined, and $X^6$ is chloro or bromo.

Equation 16

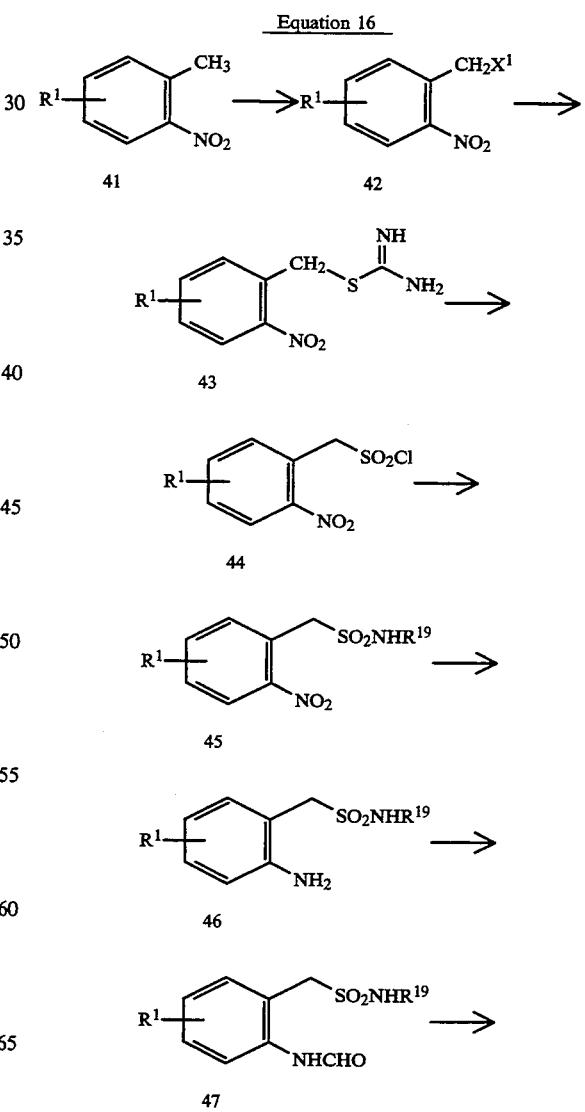

Equation 15

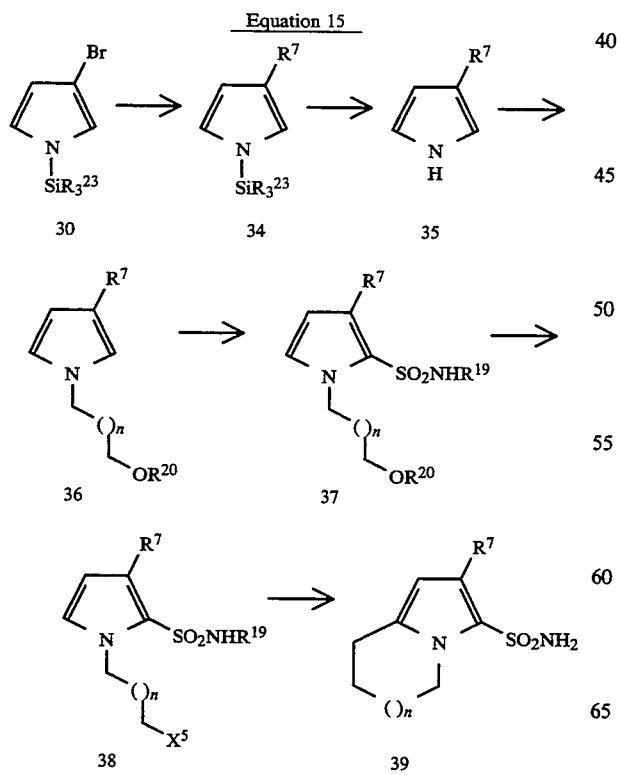

-continued
Equation 16

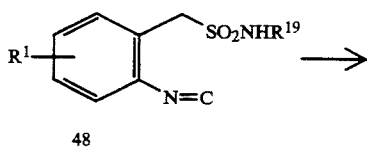

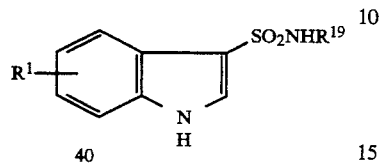

O-Nitro toluenes 41 are converted to benzylic halides 42 with halogenating agents such as N-bromosuccinimide, and subsequently to sulfonamides 45 by known methods, for example, as reported in U.S. Pat. No. 4,420,325. The nitro group of 45 is reduced to aniline 46 with any of a number of reducing agents such as iron powder in acetic acid, hydrogen and palladium metal catalyst, and the like. Formylation to 47 occurs upon reaction with formic acetic anhydride, then dehydration to isonitrile 48 is achieved with a variety of reagents, for example, with diphosgene and base as described in Chem. Ber., Vol. 121, p. 507 (1988), J. Org. Chem., Vol. 45, p. 4059 (1980), and Angewandte Chem. Int'l. Ed., Vol. 16, p. 259 (1977). Cyclization of 48 to 40 occurs upon addition of a strong base such as lithium dialkylamide bases, preferably with cooling of the reaction medium below ambient temperature, followed by work-up with aqueous acid.

Pyrazole sulfonamide intermediates 49 are known to be available from the corresponding pyrazoles as depicted in Equation 17 and taught in U.S. Pat. No. 3,665,009.

Equation 17

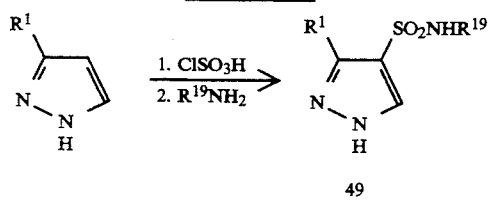

Metalation of 49 and subsequent reaction with electrophiles as depicted in Equations 6 through 12 is further described in EP-A-95,925 (published Dec. 7, 1983).

The heterocyclic amines of Formula (2a) to (2g) below are either known, or can be prepared by obvious methods by one skilled in the art.

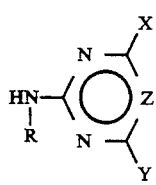 (2a)

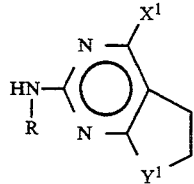 (2b)

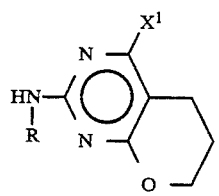 (2c)

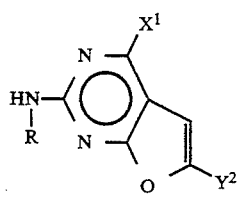 (2d)

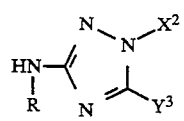 (2e)

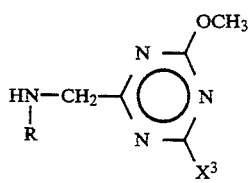 (2f)

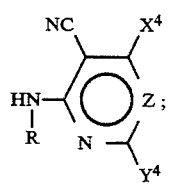 (2g)

For a review of the synthesis and reactions of 2-amino- and 2-methylaminopyrimidines see *The Chemistry of Heterocyclic Compounds*, Vol. 16, Wiley-Interscience, New York (1962). For a review of the synthesis and reactions of 2-amino- and 2-methylamino-s-triazines, see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963). *J. Chem. Soc.*, 2031 (1986), EP-A-173,498 and U.S. Pat. No. 4,666,506 describe further methods. The synthesis of the bicyclic amines (2b) and (2c) is taught in U.S. Pat. No. 4,339,267. The synthesis of bicyclic amines (2d) is taught in European Patent Application EP-A-46,667.

Compounds of Formula (2e) are described in EP-A-73,562. Compounds of Formula (2f) are described in EP-A-94,260.

The amines of Formula (2q) can be prepared by methods taught in EP-A-125,864 (published Nov. 11, 1984) or by suitable modifications that would be obvious to one skilled in the art.

The amines of Formula (2) where X or $X^1$ is $OCF_2H$ and/or Y is $OCF_2H$ or $SCF_2H$ can be prepared by methods taught in EP-A-72,347, or by suitable modifications that would be obvious to one skilled in the art.

The pyrimidines of Formula (2a) (Z=CH) where Y is

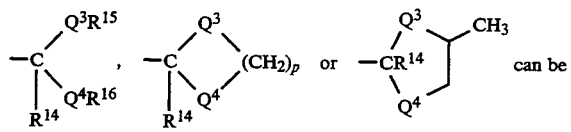 can be prepared according to the methods taught in European Patent Applicant EP-A-84,224 or suitable modifications thereof known to one skilled in the art.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Temperatures are reported in degrees Celsius; abbreviations for nuclear magnetic resonance (NMR) are: s=singlet, d=doublet, t=triplet, m=multiplet, and peak positions are reported as parts per million downfield from internal tetramethylsilane. Infrared (IR) peak positions are given in reciprocal centimeters ($cm^{-1}$) and sh denotes a shoulder.

EXAMPLE 1

N-(1,1-Dimethylethyl)-1-[tris(1-methylethyl)silyl]-1H-pyrrole-3-sulfonamide

A solution of 4.55 g (0.0151 mol) of 3-bromo-N-triisopropylsilylpyrrole in 100 mL anhydrous tetrahydrofuran (THF) under nitrogen atmosphere was cooled to −60° C. then treated with 10.4 mL of 1.6M butyllithium in hexanes (0.0166 mol) dropwise at such a rate as to keep the temperature below −60° C. After ca. 30 minutes at this temperature, liquified sulfur dioxide was added (3.9 mL, 0.090 mol). The brown solution was then warmed to room temperature, and the THF was removed under reduced pressure. The resulting light brown solid was dissolved in 100 mL acetic acid and then treated with 2.0 g (0.015 mol) N-chlorosuccinimide with cooling to keep the temperature less than 25° C. After 2 hours, the acetic acid was evaporated under reduced pressure and the residue taken up in ethyl acetate. This solution was washed successively with water, $NaHCO_3$ solution, 5% $NaHSO_3$ solution, $NaHCO_3$ solution, brine, then dried with $MgSO_4$ and evaporated in vacuo. The resulting dark brown oil residue was dissolved in methylene chloride (200 mL) and treated with 8 mL (0.075 mol) t-butylamine and then stirred for 3 days at ambient temperature. The solution was then washed with 1N HCl, dried ($MgSO_4$), and evaporated to a dark oil. Chromatography on silica gel (10% ethyl acetate/hexanes) afforded 4.0 g of the title compound as an amber oil that solidified on standing.

NMR ($CDCl_3$, 200 MHz) δ: 0.80 (d, 18H), 1.22 (s, 9H), 1.45 (m, 3H), 4.32 (s, NH), 6.55 (m, 1H), 6.72 (m, 1H), 7.25 (m, 1H). IR (nujol): 3240 $cm^{-1}$.

EXAMPLE 2

N-(1,1-Dimethylethyl)-1H-pyrrole-3-sulfonamide

A solution of N-(1,1-dimethylethyl)-1-[tris(1-methylethyl)sily]-1H-pyrrole-3-sulfonamide (1.7 g, 4.7 mmol) in 25 mL THF was treated with 5.2 mL of 1M tetrabutylammonium fluoride/THF solution, followed by 0.3 mL of acetic acid. After stirring 30 minutes at room temperature, the reaction mixture was filtered through silica with THF rinse, and the filtrate stripped. The solid residue was triturated with hexanes to afford 0.77 g of tan solids, m.p. 145°-147° C. dec.

NMR ($CDCl_3$, 400 MHz) δ: 1.27 (s, 9H), 4.36 (s, NH), 6.52 (m, 1H), 6.80 (m, 1H), 7.31 (m, 1H), 8.58 (s, NH). IR (nujol): 2270, 2360, 1300, 1125 $cm^{-1}$.

EXAMPLE 3

N-(1,1-Dimethylethyl)-1-[2-[(1,1-dimethylethyl)-dimethylsilyloxylethyl]-1H-pyrrole-3-sulfonamide A solution of 0.99 g (4.49 mmol) of N-(1,1-dimethylethyl)-1H-pyrrole-3-sulfonamide in 10 mL N,N-dimethylformamide (DMF) was cooled to 15° C. under nitrogen atmosphere. To this was added 1.41 g (5.9 mmol) of (2-bromoethoxy)(1,1-dimethylethyl)dimethylsilane followed by 0.61 g (5.4 mmol) of potassium t-butoxide. The mixture was briefly warmed to 60° C. then cooled, diluted with diethyl ether, washed three times with 1N HCl, once with brine, dried ($MgSO_4$) and evaporated under reduced pressure. The resulting solids were triturated with hexanes and collected by filtration to afford 1.31 g of the title compound, m.p. 73°-76° C.

NMR ($CDCl_3$, 200 MHz) δ: 0.86 (s, 9H), 1.26 (s, 9H), 3.83 (t, 2H), 3.94 (t, 2H), 4.25 (s, NH), 6.40 (m, 1H), 6.65 (m, 1H), 7.17 (m, 1H). IR (nujol): 3280 $cm^{-1}$.

EXAMPLE 4

3-[[(1,1-Dimethylethyl)amino]sulfonyl]-1-[2-[(1,1-dimethylethyl)dimethylsilyloxylethyl]-1H-pyrrole-2-carboxylic acid To a solution of 1.30 g (3.61 mmol) of N-(1,1-dimethylethyl-1-[2-[(1,1-dimethylsilyloxy]ethyl]-1H-pyrrole-3-sulfonamide in 30 mL THF under nitrogen atmosphere cooled to −60° C. was added dropwise 5.7 mL (9.03 mmol) 1.6M butyllithium in hexanes. The resultant yellow solution was warmed to 0° C. for 20 minutes then recooled to less than −60° C. and a large excess of crushed dry ice (4.5 g of $CO_2$) was added in one portion. After warming to room temperature, the mixture was acidified with 1N HCl and water, extracted with ethyl acetate three times. The organic extracts were washed with brine, dried (Na$_2$SO$_4$) and evaporated in vacuo. The residue was crystallized by dissolving the residue in ether and adding five volumes of hexane to afford 1.17 g of the title compound, m.p. 107°–122° C.

NMR (CDCl$_3$, 200 MHz) δ: 0.82 (s, 9H), 1.25 (s, 9H), 3.88 (t, 2H), 4.45 (t, 2H), 5.4 (s, NH), 6.68 (d, 1H), 6.91 (d, 1H). IR (nujol): 1670, 3300 cm$^{-1}$.

EXAMPLE 5

3,4-Dihydro-1-oxo-1H-pyrrolo[2,1-c][1,4]oxazine-8-sulfonamide

A mixture of 0.33 g (5.8 mmol) potassium fluoride, 1 mL water and 20 mL trifluoroacetic acid was stirred at room temperature while 1.17 g (2.9 mmol) of 3-[[(1,1-dimethylethyl)amino]sulfonyl]-1-[2-[1,1-dimethylethyl)dimethylsilyloxy]ethyl]-1H-pyrrole-2-carboxylic acid was added gradually. After several hours at room temperature, the solvent was evaporated under reduced pressure, 15 mL water was added, and the product extracted with five 50 mL portions of ethyl acetate. The organic extract was dried (MgSO$_4$) and stripped to 0.67 g of 3-(aminosulfonyl)-1-(2-hydroxyethyl)-1H-pyrrole-2-carboxylic acid. This residue was taken up in 5 mL THF and added dropwise to 120 mL toluene with stirring. p-Toluenesulfonic acid (30 mg) was added and the mixture refluxed with water separation for 3 hours. Toluene was then evaporated under reduced pressure, the residue dissolved in ethyl acetate, and washed in turn with water, and aqueous NaHCO$_3$. The ethyl acetate solution was then dried and stripped to leave 0.3 g solid residue. Trituration with CHCl$_3$:CH$_3$OH (1:1) and filtration afforded 0.10 g of the title compound, m.p. 204°–206° C.

NMR (DMSO-d$_6$, 200 MHz) δ: 4.35 (t, 2H), 4.62 (t, 2H), 6.58 (d, 1H), 6.96 (NHz), 7.26 (d, 1H). IR (nujol): 1715, 1725 sh, 3250, 3360 cm$^{-1}$.

EXAMPLE 6

3,4-Dihydro-N-[[(4-methoxy-6-methyl-1,3,5-triazin-2-yl)amino]carbonyl]-1-oxo-1H-pyrrolo[2,1-c][1,4]-oxazine-8-sulfonamide A solution of 40 mg (0.185 mmol) of 3,4-dihydro-1-oxo-1H-pyrrolo[2,1-c][1,4]oxazine-8-sulfonamide and 53 mg (0.204 mmol) of phenyl (4-methoxy-6-methyl-1,3,5-triazin-2-yl)carbamate in 0.8 mL acetonitrile was treated with 0.03 mL 1,8-diazabicyclo[5.4.0]undec-7-ene (DBU) and then stirred 40 minutes at ambient temperature. Water (5 mL) plus 0.5 mL 1N HCl was added with stirring followed by ca. 1 mL of ethyl ether. The product crystallized from the two phase mixture and was collected by filtration to afford 40 mg of the title compound, m.p. 204°–207° C. dec.

NMR (DMSO-d$_6$, 200 MHz) δ: 2.48 (s, 3H), 3.98 (s, 3H), 4.38 (t, 2H), 4.62 (t, 2H), 6.8 (d, 1H), 7.22 (d, 1H), 10.9 (NH), 12.45 (NH). IR (nujol): 1725, 1705 sh cm$^{-1}$.

EXAMPLE 7

2-Amino-N-(1,1-dimethylethyl)benzenemethanesulfonamide

A mixture of 12 g (0.044 mol) of N-(1,1-dimethylethyl)-2-nitrobenzenemethanesulfonamide and 1 g of 10% palladium on carbon in 175 mL ethanol was reduced by shaking in a hydrogen atmosphere at 50 psi for 30 minutes. The catalyst was removed by filtration through a pad of diatomaceous earth with ethanol rinsing. The filtrate was then evaporated under reduced pressure and the residue crystallized from n-butyl chloride and hexanes to afford 10.1 g of the title compound, m.p. 115°–117° C.

NMR (CDCl$_3$, 200 MHz) δ: 1.38 (s, 3H), 3.5 (br, NH$_2$), 4.12 (s, NH), 4.29 (s, 2H), 6.8 (m, 2H), 7.15 (m, 2H). IR (nujol): 3300, 3360, 3450 cm$^{-1}$.

EXAMPLE 8

N-(1,1-Dimethylethyl)-2-(formylamino)benzenemethanesulfonamide

Formic acetic anhydride was prepared by stirring a slurry of 34.4 g (0.42 mol) sodium formate in 35 mL ethyl ether and adding 24.9 mL (0.35 mol) of acetyl chloride dropwise keeping the temperature at 25° C. with intermittent cooling. After vigorous stirring for 5 hours the slurry was filtered into another reaction vessel and diluted with 100 mL CH$_2$Cl$_2$, then chilled to 0° C. A solution of 40 g (0.16 mol) 2-amino-N-(1,1-dimethylethyl)benzenemethanesulfonamide in 200 mL CH$_2$Cl$_2$ was then added dropwise keeping the temperature below 10° C. The mixture was then allowed to warm to room temperature and 50 mL methanol was added then stirred 18 hours. Evaporation of the solvent in vacuo left a residue that was taken up in chloroform, washed two times with NaHCO$_3$ solution, dried (MgSO$_4$) and stripped to dryness. The residue was triturated with n-butyl chloride and hexanes (1:1) and collected by filtration to afford 36.8 g of the title compound, m.p. 114°–115° C.

NMR (CDCl$_3$, 200 MHz) δ: 1.38 (s, 9H), 4.19 and 4.40 (NH), 4.31 and 4.33 (s, 2H), 7.3 (m, 3H), 7.83 (d, 1H), 8.42 (s, 1H), 8.62 (NH). IR (nujol): 1680, 3180, 3290 cm$^{-1}$.

EXAMPLE 9

N-(1,1-Dimethylethyl)-2-isocyanaobenzenemethanesulfonamide

A mixture of 33.6 g (0.124 mol) of N-(1,1-dimethylethyl)-2-(formylamino)benzenemethanesulfonamide and 36.8 mL (0.264 mol) triethylamine was stirred in 165 mL CH$_2$Cl$_2$ and chilled to −10° C. under nitrogen atmosphere. To this solution was added a solution of 7.5 mL (0.062 mol) trichloromethyl chloroformate in 65 mL CH$_2$Cl$_2$ dropwise over a 1 hour period, keeping the temperature less than 0° C. The mixture was then stirred for 30 minutes at 0° C., then 1 hour at room temperature. After dilution with more CH$_2$Cl$_2$, the mixture was washed with water, then NaHCO$_3$ solution, dried over 4A molecular sieves and evaporated in vacuo. The residue was taken up in ethyl acetate/hexane (1:1) and filtered through several hundred grams of neutral alumina with ethyl acetate rinse and evaporated in vacuo. This residue was triturated and collected with a mixture of n-butyl chloride and hexane to afford 25.7 g of the title compound, m.p. 106°–108° C.

NMR (CDCl$_3$, 200 MHz) δ: 1.36 (s, 9H), 4.30 (NH), 4.45 (s, 2H), 7.42 (m, 3H), 7.60 (m, 1H). IR (nujol): 3240, 2115, 1340, 1150, 1135 cm$^{-1}$.

EXAMPLE 10

N-(1,1-Dimethylethyl)-1H-indole-3-sulfonamide

A solution of 25.2 g (0.10 mol) of N-(1,1-dimethylethyl)-2-isocyanobenzenemethanesulfonamide in 600 mL anhydrous THF was cooled to −70° C. under nitrogen atmosphere and treated with 147 mL (0.22 mol) 1.5M lithium diisopropylamide mono(tetrahydrofuran) in cyclohexane at such a rate as to keep the temperature under −60° C. The mixture was stirred at −70° C. for 15 minutes then warmed to 0° C. Saturated ammonium chloride solution (75 mL) was then added and the product was extracted with two 200 mL portions of ethyl acetate. The organic extract was washed with 10% HCl, brine, dried (MgSO$_4$) and evaporated in vacuo. The resulting residue was triturated with ether/n-butyl chloride and collected by filtration to afford 22.7 g of the title compound, m.p. 157°–158° C.

NMR (CDCl$_3$, 200 MHz) δ: 1.23 (s, 9H), 4.60 (NH), 7.30 (m, 2H), 7.42 (m, 1H), 7.72 (d, 1H). 7.89 (m, 1H), 8.78 (NH). IR (nujol): 3250, 3290 cm$^{-1}$.

EXAMPLE 11

N-(1,1-Dimethylethyl)-1-[2-(tetrahydro-2-pyranyloxy)ethyl]-1H-indole-3-sulfonamide A solution of 5.0 g (0.020 mol) of N-(1,1-dimethylethyl)-1H-indole-3-sulfonamide in 30 mL anhydrous DMF was cooled to 10° C. under nitrogen atmosphere and was treated slowly with 0.87 g (0.022 mol) 60% sodium hydride (oil dispersion). The mixture was stirred for 20 minutes at room temperature then recooled to 10° C., whereupon 5.0 g (0.024 mol) of 2-(2'-bromoethoxy)tetrahydropyran (J. Org. Chem., Vol. 50, p. 4243, 1985) was added followed by heating to 70° C. for 3 hours. After cooling in an ice bath, 20 mL of saturated NH$_4$Cl solution plus 20 mL of water was added and the mixture was extracted twice with ethyl acetate. The organic extract was washed twice with dilute HCl solution, then brine followed by drying (MgSO$_4$) and evaporation in vacuo. The residue was triturated and collected by filtration with n-butyl chloride to afford 6.61 g of the title compound, m.p. 125°–132° C.

NMR (CDCl$_3$, 200 MHz) δ: 1.24 (s, 9H), 1.45 (m, 6H), 3.3–3.75 (m, 3H), 4.02 (m, 2H), 4.3 (m, 2H), 4.5 (m, 2H), 7.3 (m, 3H), 7.76 (s, 1H), 7.87 (m, 1H). IR (nujol): 1520, 3300 cm$^{-1}$.

EXAMPLE 12

3-[[(1,1-Dimethylethyl)amino]sulfonyl]-1-[2-(tetrahydro-2-pyranyloxy)ethyl]-1H-indole-2-carboxylic acid A solution of 1.8 g (4.7 mmol) of N-(1,1-dimethylethyl)-1-[2-(tetrahydro-2-pyranyloxy)-ethyl]-1H-indole-3-sulfonamide was dissolved in 30 mL anhydrous THF and cooled to −60° C. under nitrogen atmosphere. To this was added dropwise, with stirring, 8.0 mL (12.8 mmol) 1.6M butyllithium in hexanes and the mixture allowed to warm to 0° C. for 20 minutes then recooled to −60° C. A large excess of crushed dry ice (4 g CO$_2$) was added all at once then the mixture was stirred overnight at ambient temperature. Hydrochloric acid (1N, 15 mL) plus ice was then added and the mixture extracted three times with ethyl acetate. The organic extracts were washed once with brine, dried (Na$_2$SO$_4$) and evaporated in vacuo. The solid residue was triturated and collected by filtration with n-butyl chloride and hexane to afford 1.80 g of the title compound, m.p. 149°–151° C. dec.

NMR δ: 1.21 (s, 9H), 1.3–1.8 (m, 6H), 3.3–4.9 (m, 9H), 7.4 (m, 3H), 8.32 (d, 1H). IR (nujol): 1705, 3250 sh, 3100 sh cm$^{-1}$.

EXAMPLE 13

3-(Aminosulfonyl)-1-(2-hydroxyethyl)-1H-indole-2-carboxylic acid

To 50 mL acetone plus 1.80 g (4.2 mmol) of 3-[[(1,1-dimethylethyl)amino]sulfonyl]-1-[2-(tetrahydro-2-pyranyloxy)ethyl]1H-indole-2-carboxylic acid was added 4.2 mL 1N HCl and the mixture was stirred overnight. Acetone was then evaporated and the residue extracted with ethyl acetate three times. The organic layer was washed once with brine, dried (Na$_2$SO$_4$) and stripped to dryness. The residue was then taken up in trifluoroacetic acid (20 mL) then evaporated in vacuo after several hours at room temperature. The residue was triturated and collected with ethyl ether to afford 1.37 g of the title compound, m.p. 145°–146° C. dec.

NMR (DMSO-d$_6$, 200 MHz) δ: 3.65 (t, 2H), 4.41 (t, 2H), 7.1 (NH$_2$), 7.3 (m, 2H), 7.68 (d, 1H), 8.04 (d, 1H). IR (nujol): 1712, 3240, 3380, 3450 cm$^{-1}$.

EXAMPLE 14

3,4-Dihydro-1-oxo-1H-[2,4]oxazino[4,3-a]indole-10-sulfonamide

To 100 mL benzene was added 0.40 g (1.4 mmol) of 3-(aminosulfonyl)-1-(2-hydroxyethyl)-1H-indole-2-carboxylic acid followed by 20 mg of p-toluenesulfonic acid. The mixture was heated to reflux for 20 hours, cooled to room temperature, and the resulting precipitate collected by filtration to afford 0.32 g of the title compound, m.p. 254°–260° C.

NMR (DMSO-d$_6$, 200 MHz) δ: 4.59 (t, 2H), 4.84 (t, 2H), 7.13 (NH$_2$), 7.33 (t, 1H), 7.49 (t 1H), 7.72 (d, 1H), 8.79 (d, 1H). IR (nujol): 1700, 3260, 3400 cm$^{-1}$.

EXAMPLE 15

3,4-Dihydro-N-[[(4,6-dimethoxy-2-pyrimidinyl)amino]carbonyl]-1-oxo-1H[1,4]oxazino[4,3-a]indole-10-sulfonamide A 60 mg (0.23 mmol) sample of 3,4-dihydro-1-oxo-1H-[1,4]oxazino[4,3-a]indole-10-sulfonamide was dissolved in 1 mL dry acetonitrile and 70 mg (0.27 mmol) of phenyl (4,6-dimethoxypyrimidin-2-yl)carbamate was added. To this was added 0.040 mL of DBU and the mixture was stirred at room temperature for 30 minutes. A 0.2N solution of HCl was then added until the pH of the mixture was less than 2. Additional water was added and the resulting precipitate was collected by filtration and rinsed with water, then ethyl ether to afford 70 mg of the title compound, m.p. 206°–210° C. dec.

NMR (DMSO-d$_6$, 200 MHz) δ: 3.95 (s, 6H), 4.6 (t, 2H), 4.82 (t, 2H), 5.96 (s, 1H), 7.4 (t, 1H), 7.52 (t, 1H), 7.76 (d, 1H), 8.24 (d, 1H), 10.41 (NH), 12.77 (NH). IR (nujol): 1715, 1725 sh cm$^{-1}$.

By applying the procedures of Examples 1 through 15 and Equations 1 through 17, the compounds in Tables 1 through 20 can be prepared by one skilled in the art. In the following tables, abbreviations for various alkyl chains and rings have been used with the following corresponding definitions.

| | | | |
|---|---|---|---|
| Et | = ethyl | = | $CH_2CH_3$, |
| iPr | = isopropyl | = | $CH(CH_3)_2$, |
| nPr | = n-propyl | = | $CH_2CH_2CH_3$, |
| cPr | = cyclopropyl | = | $CH(CH_2)_2$, |
| cBu | = cyclobutyl | = | $CH(CH_2)_3$, |
| cC$_5$H$_9$ | = cyclopentyl | = | $CH(CH_2)_4$. |

TABLE 1

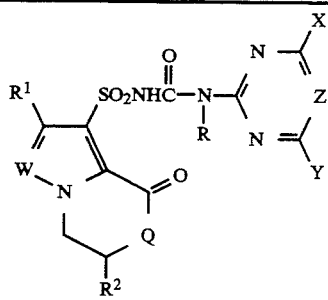

| | | R = R¹ = R² = H, Q = O, W = CH | | | |
|---|---|---|---|---|---|
| X | Y | Z | X | Y | Z |
| CH₃ | CH₃ | CH | NHCH₃ | OCH₃ | N |
| CH₃ | OCH₃ | CH | N(CH₃)₂ | OCH₃ | N |
| OCH₃ | OCH₃ | CH | C₂H₅ | OC₂H₅ | N |
| Cl | OCH₃ | CH | NHCH₃ | OC₂H₅ | N |
| CH₃ | OCH₃ | CCH₃ | N(CH₃)₂ | OC₂H₅ | N |
| CH₃ | OC₂H₅ | CH | NHCH₃ | OCH₂CF₃ | N |
| C₂H₅ | OCH₃ | CH | N(CH₃)₂ | OCH₂CF₃ | N |
| H | OCH₃ | CH | CH₃ | OC₂H₅ | N |
| H | OC₂H₅ | CH | CF₃ | OCH₃ | N |
| OCH₃ | CH₂OCH₃ | CH | OCF₂H | OCH₃ | N |
| CH₃ | CH(OCH₃)₂ | CH | CH₃ | OCH₂CH=CH₂ | N |
| OCHF₂ | OCH₃ | CH | OCH₃ | CH₃ | CCl |
| OCH₃ | SCH₃ | CH | CH₃ | CH₃ | CCH₃ |
| OCH₃ | OCH₃ | CC₂H₅ | | | |
| OCH₃ | CH₃ | CBr | | | |
| CH₃ | OCH₃ | N | | | |
| OCH₃ | OCH₃ | N | | | |

| R = R¹ = R² = H, Q = O, W = N | | | R = R¹ = R² = H, Q = S, W = CH | | |
|---|---|---|---|---|---|
| X | Y | Z | X | Y | Z |
| CH₃ | CH₃ | CH | CH₃ | CH₃ | CH |
| CH₃ | OCH₃ | CH | CH₃ | OCH₃ | CH |
| OCH₃ | OCH₃ | CH | OCH₃ | OCH₃ | CH |
| Cl | OCH₃ | CH | Cl | OCH₃ | CH |
| CH₃ | OCH₃ | CCH₃ | CH₃ | OCH₃ | CCH₃ |
| CH₃ | OC₂H₅ | CH | CH₃ | OC₂H₅ | CH |
| C₂H₅ | OCH₃ | CH | C₂H₅ | OCH₃ | CH |
| H | OCH₃ | CH | H | OCH₃ | CH |
| H | OC₂H₅ | CH | H | OC₂H₅ | CH |
| OCH₃ | CH₂OCH₃ | CH | OCH₃ | CH₂OCH₃ | CH |
| CH₃ | CH(OCH₃)₂ | CH | CH₃ | CH(OCH₃)₂ | CH |
| OCHF₂ | OCH₃ | CH | OCHF₂ | OCH₃ | CH |
| OCH₃ | SCH₃ | CH | OCH₃ | SCH₃ | CH |
| CH₃ | OCH₃ | N | CH₃ | OCH₃ | N |
| OCH₃ | OCH₃ | N | OCH₃ | OCH₃ | N |
| NHCH₃ | OCH₃ | N | NHCH₃ | OCH₃ | N |
| N(CH₃)₂ | OCH₃ | N | N(CH₃)₂ | OCH₃ | N |
| C₂H₅ | OC₂H₅ | N | C₂H₅ | OC₂H₅ | N |
| NHCH₃ | OC₂H₅ | N | NHCH₃ | OC₂H₅ | N |
| N(CH₃)₂ | OC₂H₅ | N | N(CH₃)₂ | OC₂H₅ | N |
| NHCH₃ | OCH₂CF₃ | N | NHCH₃ | OCH₂CF₃ | N |
| N(CH₃)₂ | OCH₂CF₃ | N | N(CH₃)₂ | OCH₂CF₃ | N |
| CH₃ | OC₂H₅ | N | CH₃ | OC₂H₅ | N |
| CF₃ | OCH₃ | N | CF₃ | OCH₃ | N |
| OCF₂H | OCH₃ | N | OCF₂H | OCH₃ | N |
| CH₃ | OCH₂CH=CH₂ | N | CH₃ | OCH₂CH=CH₂ | N |

| R = R¹ = R² = H, Q = S, W = N | | | R = R¹ = R² = H, Q = NCH₃, W = CH | | |
|---|---|---|---|---|---|
| X | Y | Z | X | Y | Z |
| CH₃ | CH₃ | CH | CH₃ | CH₃ | CH |
| CH₃ | OCH₃ | CH | CH₃ | OCH₃ | CH |
| OCH₃ | OCH₃ | CH | OCH₃ | OCH₃ | CH |
| Cl | OCH₃ | CH | Cl | OCH₃ | CH |
| CH₃ | OCH₃ | CCH₃ | CH₃ | OCH₃ | CCH₃ |
| CH₃ | OC₂H₅ | CH | CH₃ | OC₂H₅ | CH |
| C₂H₅ | OCH₃ | CH | C₂H₅ | OCH₃ | CH |
| H | OCH₃ | CH | H | OCH₃ | CH |
| H | OC₂H₅ | CH | H | OC₂H₅ | CH |
| OCH₃ | CH₂OCH₃ | CH | OCH₃ | CH₂OCH₃ | CH |
| CH₃ | CH(OCH₃)₂ | CH | CH₃ | CH(OCH₃)₂ | CH |
| OCHF₂ | OCH₃ | CH | OCHF₂ | OCH₃ | CH |
| OCH₃ | SCH₃ | CH | OCH₃ | SCH₃ | CH |
| CH₃ | OCH₃ | N | CH₃ | OCH₃ | N |
| OCH₃ | OCH₃ | N | OCH₃ | OCH₃ | N |
| NHCH₃ | OCH₃ | N | NHCH₃ | OCH₃ | N |

TABLE 1-continued

| | | | | | |
|---|---|---|---|---|---|
| N(CH$_3$)$_2$ | OCH$_3$ | N | N(CH$_3$)$_2$ | OCH$_3$ | N |
| C$_2$H$_5$ | OC$_2$H$_5$ | N | C$_2$H$_5$ | OC$_2$H$_5$ | N |
| NHCH$_3$ | OC$_2$H$_5$ | N | NHCH$_3$ | OC$_2$H$_5$ | N |
| N(CH$_3$)$_2$ | OC$_2$H$_5$ | N | N(CH$_3$)$_2$ | OC$_2$H$_5$ | N |
| NHCH$_3$ | OCH$_2$CF$_3$ | N | NHCH$_3$ | OCH$_2$CF$_3$ | N |
| N(CH$_3$)$_2$ | OCH$_2$CF$_3$ | N | N(CH$_3$)$_2$ | OCH$_2$CF$_3$ | N |
| CH$_3$ | OC$_2$H$_5$ | N | CH$_3$ | OC$_2$H$_5$ | N |
| CF$_3$ | OCH$_3$ | N | CF$_3$ | OCH$_3$ | N |
| OCF$_2$H | OCH$_3$ | N | OCF$_2$H | OCH$_3$ | N |
| CH$_3$ | OCH$_2$CH=CH$_2$ | N | CH$_3$ | OCH$_2$CH=CH$_2$ | N |

| R = R$^1$ = R$^2$ = H, Q = NH, W = CH | | | R = R$^1$ = R$^2$ = H, Q = NH, W = N | | |
|---|---|---|---|---|---|
| X | Y | Z | X | Y | Z |
| CH$_3$ | CH$_3$ | CH | CH$_3$ | CH$_3$ | CH |
| CH$_3$ | OCH$_3$ | CH | CH$_3$ | OCH$_3$ | CH |
| OCH$_3$ | OCH$_3$ | CH | OCH$_3$ | OCH$_3$ | CH |
| Cl | OCH$_3$ | CH | Cl | OCH$_3$ | CH |
| CH$_3$ | OCH$_3$ | CCH$_3$ | CH$_3$ | OCH$_3$ | CCH$_3$ |
| CH$_3$ | OC$_2$H$_5$ | CH | CH$_3$ | OC$_2$H$_5$ | CH |
| C$_2$H$_5$ | OCH$_3$ | CH | C$_2$H$_5$ | OCH$_3$ | CH |
| H | OCH$_3$ | CH | H | OCH$_3$ | CH |
| H | OC$_2$H$_5$ | CH | H | OC$_2$H$_5$ | CH |
| OCH$_3$ | CH$_2$OCH$_3$ | CH | OCH$_3$ | CH$_2$OCH$_3$ | CH |
| CH$_3$ | CH(OCH$_3$)$_2$ | CH | CH$_3$ | CH(OCH$_3$)$_2$ | CH |
| OCHF$_2$ | OCH$_3$ | CH | OCHF$_2$ | OCH$_3$ | CH |
| OCH$_3$ | SCH$_3$ | CH | OCH$_3$ | SCH$_3$ | CH |
| CH$_3$ | OCH$_3$ | N | CH$_3$ | OCH$_3$ | N |
| OCH$_3$ | OCH$_3$ | N | OCH$_3$ | OCH$_3$ | N |
| NHCH$_3$ | OCH$_3$ | N | NHCH$_3$ | OCH$_3$ | N |
| N(CH$_3$)$_2$ | OCH$_3$ | N | N(CH$_3$)$_2$ | OCH$_3$ | N |
| C$_2$H$_5$ | OC$_2$H$_5$ | N | C$_2$H$_5$ | OC$_2$H$_5$ | N |
| NHCH$_3$ | OC$_2$H$_5$ | N | NHCH$_3$ | OC$_2$H$_5$ | N |
| N(CH$_3$)$_2$ | OC$_2$H$_5$ | N | N(CH$_3$)$_2$ | OC$_2$H$_5$ | N |
| NHCH$_3$ | OCH$_2$CF$_3$ | N | NHCH$_3$ | OCH$_2$CF$_3$ | N |
| N(CH$_3$)$_2$ | OCH$_2$CF$_3$ | N | N(CH$_3$)$_2$ | OCH$_2$CF$_3$ | N |
| CH$_3$ | OC$_2$H$_5$ | N | CH$_3$ | OC$_2$H$_5$ | N |
| CF$_3$ | OCH$_3$ | N | CF$_3$ | OCH$_3$ | N |
| OCF$_2$H | OCH$_3$ | N | OCF$_2$H | OCH$_3$ | N |
| CH$_3$ | OCH$_2$CH=CH$_2$ | N | CH$_3$ | OCH$_2$CH=CH$_2$ | N |

| X = Y = OCH$_3$ | | | | | |
|---|---|---|---|---|---|
| R | R$^1$ | R$^2$ | Q | W | Z |
| H | Cl | H | O | CH | CH |
| H | Br | H | O | N | CH |
| H | CH$_3$ | H | NCH$_3$ | CH | N |
| CH$_3$ | H | H | O | CH | CH |
| H | H | CH$_3$ | O | CH | N |
| H | H | CH$_3$ | S | CH | CH |
| H | H | CH$_3$ | NCH$_3$ | N | N |

| X = Y = OCH$_3$, R = R$^1$ = R$^2$ = H | | |
|---|---|---|
| Q | W | Z |
| NCH$_2$CH$_2$OCH$_3$ | N | N |
| NCH$_2$CH$_2$OEt | CH | N |
| NCH$_2$CF$_3$ | CH | CH |
| NCH$_2$CHF$_2$ | CH | N |
| N(CH$_2$)$_3$CCl$_3$ | CH | N |
| N(CH$_2$)$_3$Cl | CH | CH |
| NEt | CH | CH |
| NiPr | CH | CH |
| NtBu | N | CH |
| NCHF$_2$ | CH | N |
| NCH$_2$CCH | CH | CH |
| NCH$_2$OCH$_3$ | N | CH |

| X = OCH$_3$, Y = CH$_3$ | | | | | |
|---|---|---|---|---|---|
| R | R$^1$ | R$^2$ | Q | W | Z |
| H | Cl | H | O | CH | CH |
| H | Br | H | O | N | CH |
| H | CH$_3$ | H | NCH$_3$ | CH | N |
| CH$_3$ | H | H | O | CH | CH |
| H | H | CH$_3$ | O | CH | N |
| H | H | CH$_3$ | S | CH | CH |
| H | H | CH$_3$ | NCH$_3$ | N | N |
| H | H | H | O | CCH$_3$ | N |
| H | Cl | H | O | CCl | CH |
| H | Br | H | O | CBr | N |
| H | Cl | H | O | N | CH |
| H | CH$_3$ | H | NCH$_3$ | N | N |

R = R$^1$ = R$^2$ = H, Q = O, W = CH, Z = CH

TABLE 1-continued

| X | Y | X | Y |
|---|---|---|---|
| (CH$_2$)$_3$CH$_3$ | OCH$_3$ | OCH$_3$ | CH$_2$SO$_2$CH$_3$ |
| iPr | OCH$_3$ | OCH$_3$ | cBu |
| (CH$_2$)$_4$Cl | OCH$_3$ | CH$_3$ | O(CH$_2$)$_2$CH=CH$_2$ |
| SEt | SEt | SCH$_2$CF$_3$ | OCH$_3$ |
| SCH$_3$ | OCH$_3$ | SCHF$_2$ | CH$_3$ |
| S(CH$_2$)$_3$CH$_3$ | OCH$_3$ | CF$_3$ | CF$_3$ |
| OCH$_2$OEt | CH$_3$ | CH$_2$Cl | OCH$_3$ |
| O(CH$_2$)$_2$OiPr | OCH$_3$ | CH$_2$Br | OCH$_3$ |
| O(CH$_2$)$_2$OCH$_3$ | OC$_2$H$_5$ | CH$_2$F | OEt |
| CH$_2$CH$_2$OCH$_3$ | Et | I | OCH$_3$ |
| H | H | OCH$_2$CHF$_2$ | CH$_3$ |
| Cl | N(CH$_3$)$_2$ | NHiPr | CH$_3$ |
| Br | NHCH$_3$ | N(iPr)$_2$ | CH$_3$ |
| OCH$_3$ | CN | OCH$_2$CF$_3$ | OCH$_2$CF$_3$ |
| CH$_3$ | CH$_2$C≡CH | NEt$_2$ | NEt$_2$ |
| CH$_3$ | OCH$_2$CH$_2$≡CH | OCH$_3$ | N$_3$ |
| OCH$_3$ | OCH$_2$CH=CH$_2$ | CH$_3$ | cPr |
| NEt$_2$ | OCH$_3$ | CH$_3$ | CH$_2$SEt |
| OCH$_2$iPr | OCH$_3$ | OCH$_3$ | CC$_5$H$_9$ |
| NH$_2$ | CH$_3$ | O(CH$_2$)$_3$Cl | O(CH$_2$)$_3$Cl |
| N(CH$_3$)Et | OCH$_3$ | | |
| Cl | OC$_2$H$_5$ | | |
| Br | OCH$_3$ | | |
| OCF$_2$H | OCF$_2$H | | |
| OCH$_2$CF$_3$ | OCF$_2$H | | |
| OCH$_2$CF$_3$ | CH$_3$ | | |
| OCH$_2$CH$_2$CH$_2$F | OCH$_3$ | | |
| OiPr | OCH$_3$ | | |
| CH$_3$ | N(OCH$_3$)CH$_3$ | | |
| O(CH$_2$)$_3$CH$_3$ | O(CH$_2$)$_3$CH$_3$ | | |
| iPr | iPr | | |
| OCH$_3$ | cPr | | |

R = R$^1$ = R$^2$ = H, Q = O, W = CH, Z = N

| X | Y |
|---|---|
| N(CH$_3$)$_2$ | N(CH$_3$)$_2$ |
| OEt | NHnBu |
| OCH$_3$ | NHiPr |
| OCH$_2$F | NHtBu |
| OCH$_3$ | OCF$_2$Br |
| NEt$_2$ | NEt$_2$ |
| OCH$_3$ | NEt$_2$ |
| OEt | NHCH$_2$CF$_3$ |
| OCH$_3$ | N(CH$_2$CF$_3$)$_2$ |
| OCH$_3$ | StBu |
| OCH$_3$ | CN |
| OCH$_3$ | N$_3$ |
| OEt | cPr |
| OCH$_3$ | OCH$_2$CH=CH$_2$ |
| CH$_3$ | CH$_3$ |

R = R$^1$ = R$^2$ = H, Q = O, W = CH

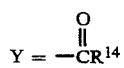

$$Y = -\overset{\overset{O}{\|}}{C}R^{14}$$

| X | R$^{14}$ | Z |
|---|---|---|
| CH$_3$ | CH$_3$ | CH |
| OCH$_3$ | CH$_3$ | CH |
| CH$_3$ | H | CH |
| OCH$_3$ | H | CH |
| CH$_3$ | (CH$_2$)$_2$CH$_3$ | CH |
| CH$_3$ | CH$_3$ | N |
| OCH$_3$ | CH$_3$ | N |
| CH$_3$ | H | N |
| OEt | H | CH |
| OCH$_3$ | Et | N |

R = R$^1$ = R$^2$ = H, Q = O, W = CH

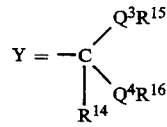

$$Y = -\underset{R^{14}}{\overset{Q^3R^{15}}{C{\diagdown Q^4R^{16}}}}$$

| X | R$^{14}$ | Q$^3$R$^{15}$ | Q$^4$R$^{16}$ | Z |
|---|---|---|---|---|
| OCH$_3$ | CH$_3$ | OCH$_3$ | OCH$_3$ | CH |
| CH$_3$ | CH$_3$ | OCH$_3$ | OCH$_3$ | CH |

TABLE 1-continued

| | | | | |
|---|---|---|---|---|
| OCH₃ | Et | OCH₃ | OCH₃ | N |
| OCH₃ | CH₃ | SEt | SEt | CH |
| CH₃ | CH₃ | S-nPr | SCH₃ | CH |
| OCH₃ | nPr | OCH₃ | OiPr | CH |

$R = R^1 = R^2 = H, Q = O, W = CH$

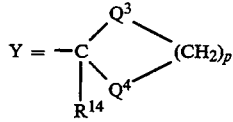

| X | R¹⁴ | O³ | O⁴ | p | Z |
|---|---|---|---|---|---|
| OCH₃ | CH₃ | S | S | 2 | CH |
| CH₃ | CH₃ | O | O | 2 | CH |
| CH₃ | CH₃ | O | O | 3 | CH |
| OCH₃ | CH₃ | S | O | 2 | N |
| OEt | CH₃ | O | O | 2 | CH |
| OCH₃ | Et | S | O | 3 | N |

$R = R^1 = R^2 = H, Q = O, W = CH, Z = CH$

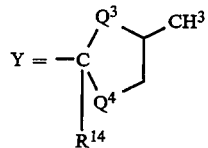

| X | R¹⁴ | O³ | O⁴ |
|---|---|---|---|
| OCH₃ | CH₃ | O | O |
| CH₃ | Et | O | O |
| OCH₃ | nPr | O | O |
| CH₃ | CH₃ | S | S |
| OCH₃ | Et | O | O |
| OCH₃ | CH₃ | S | O |

TABLE 2

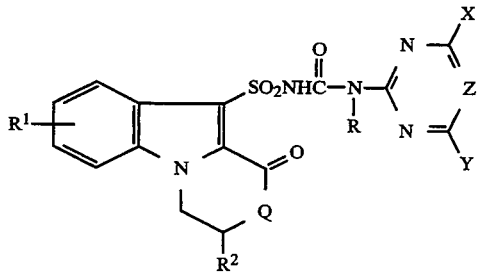

| \multicolumn{6}{c}{$R = R^1 = R^2 = H, Q = O$} |
|---|---|---|---|---|---|
| X | Y | Z | X | Y | Z |
| CH₃ | CH₃ | CH | NHCH₃ | OC₂H₅ | N |
| CH₃ | OCH₃ | CH | N(CH₃)₂ | OC₂H₅ | N |
| OCH₃ | OCH₃ | CH | NHCH₃ | OCH₂CF₃ | N |
| Cl | OCH₃ | CH | N(CH₃)₂ | OCH₂CF₃ | N |
| CH₃ | OCH₃ | CCH₃ | CH₃ | OC₂H₅ | N |
| CH₃ | OC₂H₅ | CH | CF₃ | OCH₃ | N |
| C₂H₅ | OCH₃ | CH | OCF₂H | OCH₃ | N |
| H | OCH₃ | CH | CH₃ | OCH₂CH=CH₂ | N |
| H | OC₂H₅ | CH | | | |
| OCH₃ | CH₂OCH₃ | CH | | | |
| CH₃ | CH(OCH₃)₂ | CH | | | |
| OCHF₂ | OCH₃ | CH | | | |
| OCH₃ | SCH₃ | CH | | | |
| CH₃ | OCH₃ | N | | | |
| OCH₃ | OCH₃ | N | | | |
| NHCH₃ | OCH₃ | N | | | |
| N(CH₃)₂ | OCH₃ | N | | | |
| C₂H₅ | OC₂H₅ | N | | | |

| $R = R^1 = R^2 = H, Q = NCH_3$ | | | $R = R^1 = R^2 = H, Q = S$ | | |
|---|---|---|---|---|---|
| X | Y | Z | X | Y | Z |
| CH₃ | CH₃ | CH | CH₃ | CH₃ | CH |
| CH₃ | OCH₃ | CH | CH₃ | OCH₃ | CH |

TABLE 2-continued

| R | R¹ | R² | X | Y | Z |
|---|---|---|---|---|---|
| OCH₃ | OCH₃ | CH | OCH₃ | OCH₃ | CH |
| Cl | OCH₃ | CH | Cl | OCH₃ | CH |
| CH₃ | OCH₃ | CCH₃ | CH₃ | OCH₃ | CCH₃ |
| CH₃ | OC₂H₅ | CH | CH₃ | OC₂H₅ | CH |
| C₂H₅ | OCH₃ | CH | C₂H₅ | OCH₃ | CH |
| H | OCH₃ | CH | H | OCH₃ | CH |
| H | OC₂H₅ | CH | H | OC₂H₅ | CH |
| OCH₃ | CH₂OCH₃ | CH | OCH₃ | CH₂OCH₃ | CH |
| CH₃ | CH(OCH₃)₂ | CH | CH₃ | CH(OCH₃)₂ | CH |
| OCHF₂ | OCH₃ | CH | OCHF₂ | OCH₃ | CH |
| OCH₃ | SCH₃ | CH | OCH₃ | SCH₃ | CH |
| CH₃ | OCH₃ | N | CH₃ | OCH₃ | N |
| OCH₃ | OCH₃ | N | OCH₃ | OCH₃ | N |
| NHCH₃ | OCH₃ | N | NHCH₃ | OCH₃ | N |
| N(CH₃)₂ | OCH₃ | N | N(CH₃)₂ | OCH₃ | N |
| C₂H₅ | OC₂H₅ | N | C₂H₅ | OC₂H₅ | N |
| NHCH₃ | OC₂H₅ | N | NHCH₃ | OC₂H₅ | N |
| N(CH₃)₂ | OC₂H₅ | N | N(CH₃)₂ | OC₂H₅ | N |
| NHCH₃ | OCH₂CF₃ | N | NHCH₃ | OCH₂CF₃ | N |
| N(CH₃)₂ | OCH₂CF₃ | N | N(CH₃)₂ | OCH₂CF₃ | N |
| CH₃ | OC₂H₅ | N | CH₃ | OC₂H₅ | N |
| CF₃ | OCH₃ | N | CF₃ | OCH₃ | N |
| OCF₂H | OCH₃ | N | OCF₂H | OCH₃ | N |
| CH₃ | OCH₂CH=CH₂ | N | CH₃ | OCH₂CH=CH₂ | N |

| X = Y = OCH₃ | | | | | |
|---|---|---|---|---|---|
| R | R¹ | R² | O | W | Z |
| H | Cl | H | O | CH | CH |
| H | Br | H | O | N | CH |
| H | CH₃ | H | NCH₃ | CH | N |
| CH₃ | H | H | O | CH | CH |
| H | H | CH₃ | O | CH | N |
| H | H | CH₃ | S | CH | CH |
| H | H | CH₃ | NCH₃ | N | N |

| X = CH₃, Y = OCH₃, R = R¹ = R² = H | | |
|---|---|---|
| O | W | Z |
| NCH₂CH₂OCH₃ | N | N |
| NCH₂CH₂OEt | CH | N |
| NCH₂CF₃ | CH | CH |
| NCH₂CHF₂ | CH | N |
| N(CH₂)₃CCl₃ | CH | N |
| N(CH₂)₃Cl | CH | CH |
| NEt | CH | CH |
| NiPr | CH | CH |
| NtBu | N | CH |
| NCF₂ | CH | N |
| NCH₂CCH | CH | CH |
| NCH₂OCH₃ | N | CH |

TABLE 3

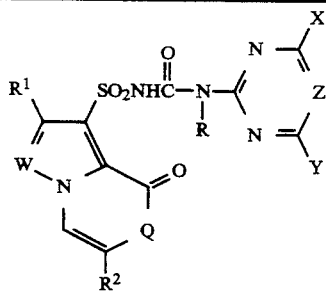

| R¹ = R² = H, Q = O, W = CH | | | | R¹ = R² = H, Q = NCH₃, W = CH | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R² = H, Q = NH, W = CH | | | | R¹ = R² = H, Q = O, W = N | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R² = H, Q = S, W = CH | | | | R¹ = R² = H, Q = NCH₃, W = N | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

TABLE 3-continued

| R¹ = R² = H, Q = NH, W = N | | | | R¹ = CH₃, R² = H, Q = O, W W = N | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = Cl, R² = H, Q = O, W = CH | | | |
|---|---|---|---|
| R | X | Y | Z |
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

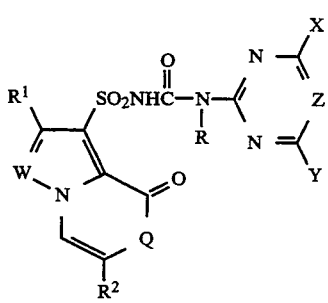

| R¹ = H, R² = CH₃, Q = O, W = CH | | | |
|---|---|---|---|
| R | X | Y | Z |
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

TABLE 4

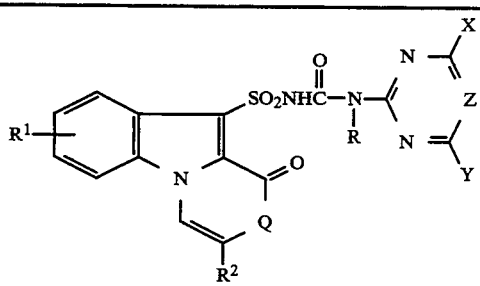

| R¹ = R² = H, Q = O | | | | R¹ = R² = H, Q = NCH₃ | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |

TABLE 4-continued

| H | OCH₃ | OCH₃ | N | H | OCH₃ | OCH₃ | N |
|---|---|---|---|---|---|---|---|
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R² = H, Q = S | | | |
|---|---|---|---|
| R | X | Y | Z |
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

TABLE 5

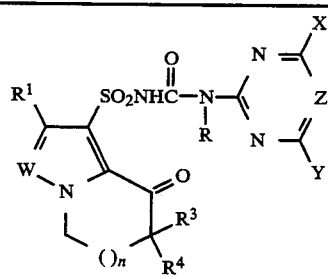

| R¹ = R³ = R⁴ = H, W = CH, n = 0 | | | | R¹ = R³ = R⁴ = H, W = N, n = 1 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R³ = R⁴ = H, W = N, n = 0 | | | | R¹ = R⁴ = H, R³ = CH₃, n = 1, W = CH | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R³ = R⁴ = H, n = 0, W = CH | | | | R¹ = H, R³ = R⁴ = CH₃, n = 1, W = N | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R = H, X = Y = OCH₃ | | | | | |
|---|---|---|---|---|---|
| R¹ | R³ | R⁴ | n | W | Z |
| H | H | Cl | 1 | N | N |
| Cl | H | H | 0 | CH | CH |

TABLE 5-continued

| | | | | | |
|---|---|---|---|---|---|
| H | Cl | Cl | 1 | N | CH |
| H | CH₃ | H | 1 | CH | N |
| H | F | F | 0 | CH | CH |
| H | Br | H | 1 | CH | CH |
| H | Br | CH₃ | 1 | CH | N |
| H | CH₃ | CH₃ | 0 | N | CH |

TABLE 6

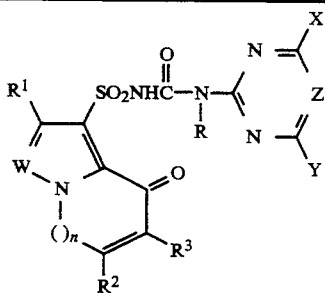

| R¹ = R³ = R² = H, W = CH, n = 1 | | | | R¹ = R³ = R² = H, W = N, n = 1 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

TABLE 7

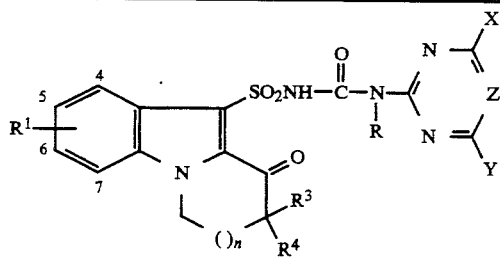

| R¹ = R³ = R⁴ = H, n = 1 | | | | R¹ = R³ = R⁴ = H, n = 0 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R³ = H, R⁴ = CH₃, n = 1 | | | |
|---|---|---|---|
| R | X | Y | Z |
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

TABLE 7-continued

| R = H, X = CH₃, Y = OCH₃ | | | | |
|---|---|---|---|---|
| R¹ | R³ | R⁴ | n | Z |
| 5-CH₃ | H | H | 1 | CH |
| 4-Cl | H | H | 0 | N |
| H | F | H | 1 | CH |
| H | Cl | Cl | 0 | N |
| H | CH₃ | H | 0 | CH |
| H | H | Br | 1 | CH |
| H | F | F | 0 | N |

TABLE 8

(structure)

| R¹ = R³ = R² = H, n = 1 | | | | R¹ = R³ = R² = H, n = 0 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

TABLE 9

(structure)

| R¹ = R² = H, W = CH, Q¹ = O | | | | R¹ = R² = H, W = CH, Q¹ = NH | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = R² = H, W = CH, Q¹ = NCH₃ | | | | R¹ = R² = H, W = N, Q¹ = NCH₃ | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |

TABLE 9-continued

| R | X | Y | Z | R | X | Y | Z |
|---|---|---|---|---|---|---|---|
| H | OCH$_3$ | OCH$_3$ | N | H | OCH$_3$ | OCH$_3$ | N |
| H | NHCH$_3$ | OC$_2$H$_5$ | N | H | NHCH$_3$ | OC$_2$H$_5$ | N |
| H | N(CH$_3$)$_2$ | OC$_2$H$_5$ | N | H | N(CH$_3$)$_2$ | OC$_2$H$_5$ | N |
| CH$_3$ | OCH$_3$ | OCH$_3$ | N | CH$_3$ | OCH$_3$ | OCH$_3$ | N |

| $R^1 = R^2 = H$, $W = N$, $Q^1 = O$ | | | | $R^1 = R^2 = H$, $W = CH$, $Q^1 = NCH_2CH_2CH_2CH_3$ | | | |
|---|---|---|---|---|---|---|---|
| R | X | Y | Z | R | X | Y | Z |
| H | CH$_3$ | CH$_3$ | CH | H | CH$_3$ | CH$_3$ | CH |
| H | CH$_3$ | OCH$_3$ | CH | H | CH$_3$ | OCH$_3$ | CH |
| H | OCH$_3$ | OCH$_3$ | CH | H | OCH$_3$ | OCH$_3$ | CH |
| H | Cl | OCH$_3$ | CH | H | Cl | OCH$_3$ | CH |
| CH$_3$ | OCH$_3$ | OCH$_3$ | CH | CH$_3$ | OCH$_3$ | OCH$_3$ | CH |
| H | CH$_3$ | OCH$_3$ | N | H | CH$_3$ | OCH$_3$ | N |
| H | OCH$_3$ | OCH$_3$ | N | H | OCH$_3$ | OCH$_3$ | N |
| H | NHCH$_3$ | OC$_2$H$_5$ | N | H | NHCH$_3$ | OC$_2$H$_5$ | N |
| H | N(CH$_3$)$_2$ | OC$_2$H$_5$ | N | H | N(CH$_3$)$_2$ | OC$_2$H$_5$ | N |
| CH$_3$ | OCH$_3$ | OCH$_3$ | N | CH$_3$ | OCH$_3$ | OCH$_3$ | N |

| $R = H$, $X = OCH_3$, $Y = OCH_3$, $Q^1 = NR^8$ | | | | |
|---|---|---|---|---|
| R$^1$ | R$^2$ | R$^8$ | N | Z |
| H | H | Et | CH | N |
| H | H | nC$_4$H$_9$ | N | CH |
| Cl | H | CH$_2$CF$_3$ | CH | CH |
| H | H | CH$_2$CH=CH$_2$ | CH | N |
| H | H | CH$_2$=CH$_2$ | CH | CH |
| CH$_3$ | H | CH$_2$OCH$_3$ | CH | N |
| H | CH$_3$ | CH$_2$CH$_2$OCH$_3$ | CH | CH |
| H | H | (CH$_2$)$_3$CH$_2$Cl | N | CH |
| H | H | CH(CH$_3$)OEt | CH | CH |

TABLE 10

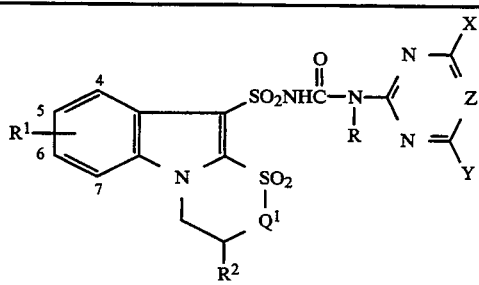

| $R^1 = R^2 = H$, $Q^1 = O$ | | | | $R^1 = R^2 = H$, $Q^1 = NCH_3$ | | | |
|---|---|---|---|---|---|---|---|
| R | X | Y | Z | R | X | Y | Z |
| H | CH$_3$ | CH$_3$ | CH | H | CH$_3$ | CH$_3$ | CH |
| H | CH$_3$ | OCH$_3$ | CH | H | CH$_3$ | OCH$_3$ | CH |
| H | OCH$_3$ | OCH$_3$ | CH | H | OCH$_3$ | OCH$_3$ | CH |
| H | Cl | OCH$_3$ | CH | H | Cl | OCH$_3$ | CH |
| CH$_3$ | OCH$_3$ | OCH$_3$ | CH | CH$_3$ | OCH$_3$ | OCH$_3$ | CH |
| H | CH$_3$ | OCH$_3$ | N | H | CH$_3$ | OCH$_3$ | N |
| H | OCH$_3$ | OCH$_3$ | N | H | OCH$_3$ | OCH$_3$ | N |
| H | NHCH$_3$ | OC$_2$H$_5$ | N | H | NHCH$_3$ | OC$_2$H$_5$ | N |
| H | N(CH$_3$)$_2$ | OC$_2$H$_5$ | N | H | N(CH$_3$)$_2$ | OC$_2$H$_5$ | N |
| CH$_3$ | OCH$_3$ | OCH$_3$ | N | CH$_3$ | OCH$_3$ | OCH$_3$ | N |

| $R^1 = R^2 = H$, $Q^1 = NH$ | | | |
|---|---|---|---|
| R | X | Y | Z |
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

| $R = H$, $X = CH_3$, $Y = OCH_3$, $Q^1 = NR^8$ | | | |
|---|---|---|---|
| R$^1$ | R$^2$ | R$^8$ | Z |
| 5-CH$_3$ | H | iPr | CH |
| H | H | CH$_2$CH(CH$_3$)$_2$ | N |
| 5-Cl | H | H | CH |
| H | CH$_3$ | CH$_2$CH=CH$_2$ | N |
| H | H | CH$_2$OCH$_3$ | N |

TABLE 10-continued

| H | H | CH$_2$CF$_3$ | CH |
|---|---|---|---|
| H | H | CHF$_2$ | N |

TABLE 11

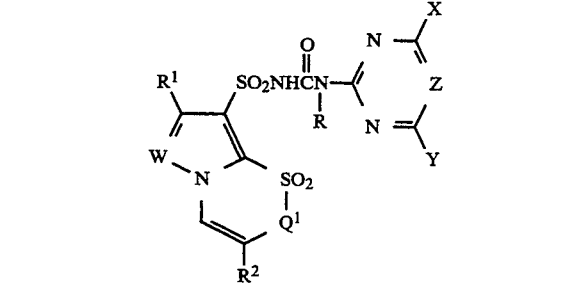

| $R^1 = R^2 = H$, $W = CH$, $Q^1 = NCH_3$ | | | | $R^1 = R^2 = H$, $W = N$, $Q^1 = NCH_3$ | | | |
|---|---|---|---|---|---|---|---|
| R | X | Y | Z | R | X | Y | Z |
| H | CH$_3$ | CH$_3$ | CH | H | CH$_3$ | CH$_3$ | CH |
| H | CH$_3$ | OCH$_3$ | CH | H | CH$_3$ | OCH$_3$ | CH |
| H | OCH$_3$ | OCH$_3$ | CH | H | OCH$_3$ | OCH$_3$ | CH |
| H | Cl | OCH$_3$ | CH | H | Cl | OCH$_3$ | CH |
| CH$_3$ | OCH$_3$ | OCH$_3$ | CH | CH$_3$ | OCH$_3$ | OCH$_3$ | CH |
| H | CH$_3$ | OCH$_3$ | N | H | CH$_3$ | OCH$_3$ | N |
| H | OCH$_3$ | OCH$_3$ | N | H | OCH$_3$ | OCH$_3$ | N |
| H | NHCH$_3$ | OC$_2$H$_5$ | N | H | NHCH$_3$ | OC$_2$H$_5$ | N |
| H | N(CH$_3$)$_2$ | OC$_2$H$_5$ | N | H | N(CH$_3$)$_2$ | OC$_2$H$_5$ | N |
| CH$_3$ | OCH$_3$ | OCH$_3$ | N | CH$_3$ | OCH$_3$ | OCH$_3$ | N |

| $R^1 = R^2 = H$, $W = CH$, $Q^1 = O$ | | | |
|---|---|---|---|
| R | X | Y | Z |
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

TABLE 12

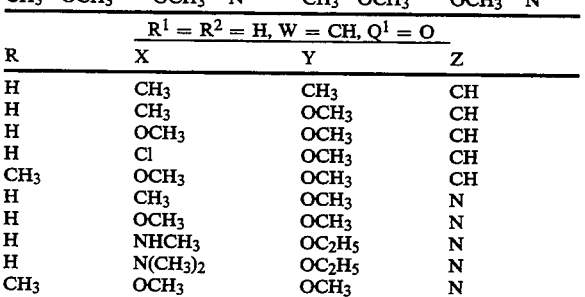

| $R^1 = R^2 = H$, $Q^1 = NCH_3$ | | | | $R^1 = R^2 = H$, $Q^1 = NH$ | | | |
|---|---|---|---|---|---|---|---|
| R | X | Y | Z | R | X | Y | Z |
| H | CH$_3$ | CH$_3$ | CH | H | CH$_3$ | CH$_3$ | CH |
| H | CH$_3$ | OCH$_3$ | CH | H | CH$_3$ | OCH$_3$ | CH |
| H | OCH$_3$ | OCH$_3$ | CH | H | OCH$_3$ | OCH$_3$ | CH |
| H | Cl | OCH$_3$ | CH | H | Cl | OCH$_3$ | CH |
| CH$_3$ | OCH$_3$ | OCH$_3$ | CH | CH$_3$ | OCH$_3$ | OCH$_3$ | CH |
| H | CH$_3$ | OCH$_3$ | N | H | CH$_3$ | OCH$_3$ | N |
| H | OCH$_3$ | OCH$_3$ | N | H | OCH$_3$ | OCH$_3$ | N |
| H | NHCH$_3$ | OC$_2$H$_5$ | N | H | NHCH$_3$ | OC$_2$H$_5$ | N |
| H | N(CH$_3$)$_2$ | OC$_2$H$_5$ | N | H | N(CH$_3$)$_2$ | OC$_2$H$_5$ | N |
| CH$_3$ | OCH$_3$ | OCH$_3$ | N | CH$_3$ | OCH$_3$ | OCH$_3$ | N |

| $R^1 = R^2 = H$, $Q^1 = O$ | | | |
|---|---|---|---|
| R | X | Y | Z |
| H | CH$_3$ | CH$_3$ | CH |

TABLE 12-continued

| | | | |
|---|---|---|---|
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

TABLE 13

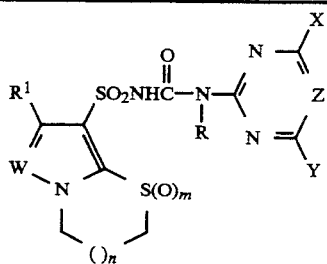

$R^1 = H$, n = 1, m = 2, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 1, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 0, m = 2, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 2, W = N

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 0, m = 2, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 1, W = N

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 0, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = CH_3$, n = 1, m = 2, W = N

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 0, W = N

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

TABLE 14

$R^1 = H$, n = 1, m = 2

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 1, m = 1

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

$R^1 = H$, n = 0, m = 0

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |
| CH$_3$ | OCH$_3$ | OCH$_3$ | CH |
| H | CH$_3$ | OCH$_3$ | N |
| H | OCH$_3$ | OCH$_3$ | N |
| H | NHCH$_3$ | OC$_2$H$_5$ | N |
| H | N(CH$_3$)$_2$ | OC$_2$H$_5$ | N |
| CH$_3$ | OCH$_3$ | OCH$_3$ | N |

TABLE 15

$R^1 = R^5 = H$, $Q^2 = O$, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |

$R^1 = R^5 = H$, $Q^2 = NCH_3$, W = CH

| R | X | Y | Z |
|---|---|---|---|
| H | CH$_3$ | CH$_3$ | CH |
| H | CH$_3$ | OCH$_3$ | CH |
| H | OCH$_3$ | OCH$_3$ | CH |
| H | Cl | OCH$_3$ | CH |

TABLE 15-continued

| | | | | | | | |
|---|---|---|---|---|---|---|---|
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

$R^1 = R^5 = H, Q^2 = S, W = N$

| R | X | Y | Z |
|---|---|---|---|
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

$R = H, X = CH_3, Y = OCH_3$

| R¹ | R⁵ | Q² | W | Z |
|---|---|---|---|---|
| H | H | NCH₃ | N | CH |
| H | CH₃ | O | CH | N |
| H | iPr | S | CH | N |
| H | nPr | NCH₃ | N | CH |
| Cl | Et | O | CH | CH |

TABLE 16

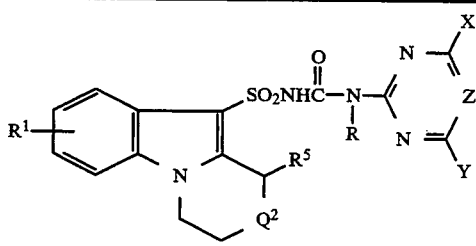

| $R^1 = R^5 = H, Q^2 = O$ | | | | $R^1 = R^5 = H, Q^2 = NCH_3$ | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

$R^1 = R^5 = H, Q^2 = S$

| R | X | Y | Z |
|---|---|---|---|
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

TABLE 17

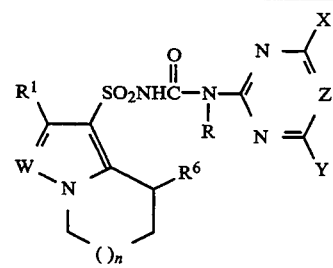

| $R^1 = R^6 = H, n = 1, W = CH$ | | | | $R^1 = R^6 = H, n = 0, W = CH$ | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| $R^1 = R^6 = H, n = 1, W = N$ | | | | $R^1 = R^6 = H, n = 0, W = N$ | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

$R^1 = H, R^6 = CH_3, n = 1, W = CH$

| R | X | Y | Z |
|---|---|---|---|
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

$R = H, X = OCH_3, Y = OCH_3$

| R¹ | R⁶ | n | W | Z |
|---|---|---|---|---|
| H | CH₃ | 1 | CH | N |
| H | iPr | 1 | N | N |
| H | OEt | 1 | CH | CH |
| H | OCH₃ | 0 | CH | CH |
| Cl | Cl | 0 | N | CH |
| H | F | 1 | CH | N |
| H | OC(O)CH₃ | 0 | CH | CH |
| H | OC(O)Et | 1 | N | CH |
| H | OSO₂CH₃ | 1 | CH | N |
| H | OSO₂Et | 0 | N | CH |
| H | OnPr | 1 | N | CH |

TABLE 18

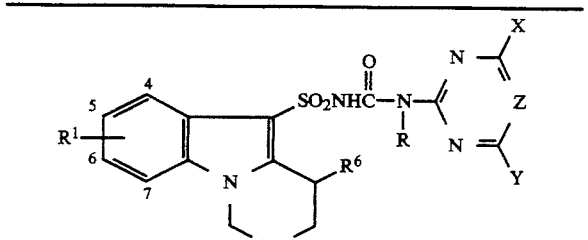

| R¹ = R⁶ = H, n = 1 | | | | R¹ = R⁶ = H, n = 0 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R¹ = H, R⁶ = CH₃, n = 1 | | | |
|---|---|---|---|
| R | X | Y | Z |
| H | CH₃ | CH₃ | CH |
| H | CH₃ | OCH₃ | CH |
| H | OCH₃ | OCH₃ | CH |
| H | Cl | OCH₃ | CH |
| CH₃ | OCH₃ | OCH₃ | CH |
| H | CH₃ | OCH₃ | N |
| H | OCH₃ | OCH₃ | N |
| H | NHCH₃ | OC₂H₅ | N |
| H | N(CH₃)₂ | OC₂H₅ | N |
| CH₃ | OCH₃ | OCH₃ | N |

| R = H, X = CH₃, Y = OCH₃ | | | |
|---|---|---|---|
| R¹ | R⁶ | n | Z |
| H | OEt | 0 | N |
| H | OSO₂CH₃ | 1 | CH |
| 6-CH₃ | OCH₃ | 1 | CH |
| H | Cl | 1 | N |
| H | OC(O)CH₃ | 0 | CH |

TABLE 19

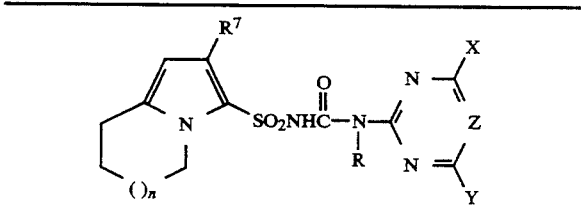

| R⁷ = CO₂CH₃, n = 1 | | | | R⁷ = CON(CH₃)₂, n = 1 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R⁷ = CO₂CH₃, n = 0 | | | | R⁷ = SO₂N(CH₃)₂, n = 1 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

TABLE 19-continued

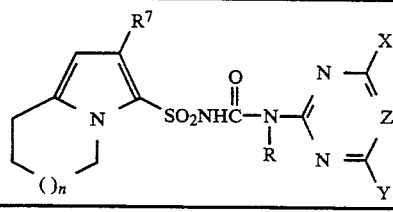

| R⁷ = SO₂CH₃, n = 1 | | | | R⁷ = SO₂N(CH₃)₂, n = 0 | | | |
|---|---|---|---|---|---|---|---|
| R | X | Y | Z | R | X | Y | Z |
| H | CH₃ | CH₃ | CH | H | CH₃ | CH₃ | CH |
| H | CH₃ | OCH₃ | CH | H | CH₃ | OCH₃ | CH |
| H | OCH₃ | OCH₃ | CH | H | OCH₃ | OCH₃ | CH |
| H | Cl | OCH₃ | CH | H | Cl | OCH₃ | CH |
| CH₃ | OCH₃ | OCH₃ | CH | CH₃ | OCH₃ | OCH₃ | CH |
| H | CH₃ | OCH₃ | N | H | CH₃ | OCH₃ | N |
| H | OCH₃ | OCH₃ | N | H | OCH₃ | OCH₃ | N |
| H | NHCH₃ | OC₂H₅ | N | H | NHCH₃ | OC₂H₅ | N |
| H | N(CH₃)₂ | OC₂H₅ | N | H | N(CH₃)₂ | OC₂H₅ | N |
| CH₃ | OCH₃ | OCH₃ | N | CH₃ | OCH₃ | OCH₃ | N |

| R = H, X = Y = OCH₃ | | |
|---|---|---|
| R⁷ | n | Z |
| CO₂Et | 1 | CH |
| CO₂tBu | 1 | CH |
| CO₂tBu | 0 | N |
| CO₂iPr | 1 | CH |
| C(O)NEt₂ | 0 | CH |
| C(O)NHCH₃ | 1 | CH |
| C(O)NHEt | 0 | N |
| SO₂NEt₂ | 1 | CH |
| SO₂NHCH₃ | 0 | CH |
| SO₂NHEt | 1 | N |
| SO₂CH₃ | 1 | CH |
| SO₂nPr | 0 | CH |
| SO₂Et | 1 | N |
| SO₂CH₃ | 0 | N |

TABLE 20

R¹ = R² = R³ = R⁴ = R⁵ = R⁶ = H
Q = Q² = O, Q¹ = NCH₃

| L | A | X¹ | Y¹ |
|---|---|---|---|
| L-1 | A-2 | CH₃ | O |
| L-1 | A-2 | OEt | O |
| L-2 | A-2 | OCH₃ | O |
| L-3 | A-2 | CH₃ | O |
| L-4 | A-2 | CH₃ | O |
| L-1 | A-3 | OCH₃ | — |
| L-5 | A-3 | OCH₃ | — |
| L-1 | A-2 | OCH₃ | CH₂ |
| L-1 | A-2 | OCF₂H | O |
| L-2 | A-2 | OCH₃ | CH₂ |
| L-2 | A-2 | CH₃ | O |
| L-4 | A-2 | OCH₃ | CH₂ |
| L-1 | A-3 | CH₃ | — |
| L-5 | A-3 | OEt | — |

| L | A | X¹ | Y³ |
|---|---|---|---|
| L-1 | A-4 | CH₃ | CH₃ |
| L-3 | A-4 | OCH₃ | H |
| L-8 | A-4 | CH₃ | CH₃ |
| L-2 | A-4 | CH₃ | CH₃ |
| L-4 | A-4 | CH₃ | H |
| L-7 | A-4 | CH₃ | H |

| L | A | X² | Y² |
|---|---|---|---|
| L-1 | A-5 | CH₃ | CH₃ |
| L-1 | A-5 | CH₃ | OCH₃ |
| L-3 | A-5 | CH₂CF₃ | OCH₃ |

TABLE 20-continued $$\underset{\text{LSO}_2\text{NHCNHA}}{\overset{\overset{\text{O}}{\|}}{}}$$

$R^1 = R^2 = R^3 = R^4 = R^5 = R^6 = H$
$Q = Q^2 = O, Q^1 = NCH_3$

| L | A | | |
|---|---|---|---|
| L-9 | A-5 | CH$_3$ | OCH$_3$ |
| L-11 | A-5 | CH$_3$ | OEt |
| L-1 | A-5 | CH$_3$ | SEt |
| L-2 | A-5 | CH$_3$ | Et |
| L-4 | A-5 | CH$_3$ | SCH$_3$ |
| L-10 | A-5 | Et | Et |
| L-12 | A-5 | CH$_3$ | OCH$_3$ |

| L | A | X$^3$ |
|---|---|---|
| L-1 | A-6 | CH$_3$ |
| L-7 | A-6 | CH$_3$ |
| L-2 | A-6 | OCH$_3$ |
| L-1 | A-6 | OCH$_3$ |
| L-8 | A-6 | OCH$_3$ |
| L-14 | A-6 | CH$_3$ |

| L | A | X$^4$ | Y$^4$ | Z$^1$ |
|---|---|---|---|---|
| L-1 | A-7 | CH$_3$ | CH$_3$ | CH |
| L-1 | A-7 | OCH$_3$ | CH$_3$ | CH$_3$ |
| L-2 | A-7 | OCH$_3$ | OCH$_3$ | N |
| L-2 | A-7 | CH$_3$ | OEt | CH |
| L-3 | A-7 | Cl | CH$_3$ | CH |
| L-4 | A-7 | OEt | OEt | N |
| L-5 | A-7 | CH$_3$ | CH$_3$ | CH |
| L-7 | A-7 | CH$_3$ | CH$_3$ | CH |
| L-8 | A-7 | CH$_3$ | CH$_3$ | CH |
| L-15 | A-7 | CH$_3$ | OCH$_3$ | N |
| L-16 | A-7 | OCH$_3$ | OCH$_3$ | CH |
| L-12 | A-7 | CH$_3$ | CH$_3$ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4; G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 16

| High Strength Concentrate | |
|---|---|
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide | 99% |
| trimethylnonyl polyethylene glycol ether | 1% |

The surfactant is sprayed upon the active ingredient in a blender and the mixture sifted through a U.S. Ser. No. 40 sieve (0.42 mm openings) prior to packaging. The concentrate may be formulated further for practical use.

EXAMPLE 17

| Wettable Powder | |
| --- | --- |
| 3,4-dihydro-N-[[(4-methoxy-6-methyl-2-pyrimidinyl)amino]carbonyl]-1-oxo-1H-[1,4]oxazine[4,3-a]indole-10-sulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S. Ser. No. 50 sieve (0.3 mm opening) and packaged.

EXAMPLE 18

| Aqueous Suspension | |
| --- | --- |
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide | 50.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 19

| Oil Suspension | |
| --- | --- |
| 3,4-dihydro-N-[[(4-methoxy-6-methyl-2-pyrimidinyl)amino]carbonyl]-1-oxo-1H-[1,4]oxazine[4,3-a]indole-10-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 20

| Oil Suspension | |
| --- | --- |
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 21

| Aqueous Suspension | |
| --- | --- |
| 3,4-dihydro-N-[[(4-methoxy-6-methyl-2-pyrimidinyl)amino]carbonyl]-1-oxo-1H-[1,4]oxazine[4,3-a]indole-10-sulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 22

| Wettable Powder | |
| --- | --- |
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide | 40.0% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S. Ser. No. 50 sieve (0.3 mm opening) before packaging.

All compounds of the invention may be formulated in the same manner.

EXAMPLE 23

| Granule | |
| --- | --- |
| wettable powder of Example 22 | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S. Ser. No. #18 to 40 sieves), the granules are removed, dried, and screened. Oversized material is crushed to produce additional material in the desired range. These granules contain % active ingredient.

EXAMPLE 24

| Wettable Powder | |
| --- | --- |
| 3,4-dihydro-N-[[(4-methoxy-6-methyl-2-pyrimidinyl)amino]carbonyl]-1-oxo-1H-[1,4]oxazine[4,3-a]indole-10-sulfonamide | 50% |
| sodium alkylnaphthalenesulfonate | 2% |
| low viscosity methyl cellulose | 2% |
| diatomaceous earth | 46% |

The ingredients are blended, coarsely hammermilled and the air milled to produce particles of active essentially all below 10 microns in diameter. The product is reblended before packaging.

EXAMPLE 25

| Extruded Pellet | |
| --- | --- |
| 3,4-dihydro-N-[[(4-methoxy-6-methyl-1,3,5- | 25% |

-continued

| Extruded Pellet | |
|---|---|
| triazin-2-yl)amino]carbonyl]-1-oxo-1H-pyrrolo[2,1-c][1,4]oxazine-8-sulfonamide | |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 26

| Wettable Powder | |
|---|---|
| 3,4-dihydro-N-[[(4-methoxy-6-methyl-2-pyrimidinyl)amino]carbonyl]-1-oxo-1H-[1,4]oxazine[4,3-a]indole-10-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S. Ser. No. 50 sieve (0.3 mm opening) before being packaged.

EXAMPLE 27

| High Strength Concentrate | |
|---|---|
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide | 98.5% |
| silica aerogel | 0.5% |
| synthetic amorphous fine silica | 1.0% |

The ingredients are blended and ground in a hammer mill to produce a high strength concentrate essentially all passing a U.S. Ser. No. 50 sieve (0.3 mm openings). This material may then be formulated in a variety of ways.

EXAMPLE 28

| Solution | |
|---|---|
| 3,4-dihydro-N-[[(4-methoxy-6-methyl-1,3,5-triazin-2-yl)amino]carbonyl]-1-oxo-1H-pyrrolo[2,1-c][1,4]oxazine-8-sulfonamide, sodium salt | 5% |
| water | 95% |

The salt is added directly to the water with stirring to produce the solution, which may then be packaged for use.

EXAMPLE 29

| Solution | |
|---|---|
| 3,4-dihydro-N-[[(4-methoxy-6-methyl-2-pyrimidinyl)amino]carbonyl]-1-oxo-1H-[1,4]oxazine[4,3-a]indole-10-sulfonamide, sodium salt | 5% |
| water | 95% |

The salt is added directly to the water with stirring to produce the solution, which may then be packaged for use.

Utility

Test results indicate that compounds of this invention are active postemergence and preemergence herbicides or plant growth regulants. Several compounds in this invention are useful for the control of selected grass and broadleaf weeds with tolerance to important agronomic crops which include, but are not limited to cotton (*Gossypium hirsutum*), wheat (*Triricum vulgaris*), barley (*Hordeum vulgare*), sugar beets (*Beta vulgaris*), and soybean (*Glycine max*). Grass and broadleaf weed species controlled include, but are not limited to barnyardgrass (*Echinochloa crus-galli*), crabgrass (*Digitaria* spp.), cheatgrass (*Bromus* spp.), cocklebur (*Xanthium pensylvanicum*), and foxtail (*Setaria* spp.).

Weed control can be achieved with normal tillage, reduced tillage and no tillage cropping systems.

These compounds also have utility for complete control and/or selected control of vegetation in specified areas such as around storage tanks, parking lots, highways, and railways, and in fallow crop, citrus, and plantation crop areas. Alternatively, these compounds may be useful to modify plant growth and as citrus abscission agents.

An effective herbicidal amount of a compound from this invention is determined by a number of factors. These factors include: formulation selected, method of application, amount and type of vegetation present, growing conditions, etc. In general terms, an effective amount of a compound from this invention is applied at rates from 0.001 to 20 kg/ha with a preferred rate range of 0.004 to 0.25 kg/ha. One skilled in the art can easily determine the application rate needed for the desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |

| Common Name | Chemical Name |
|---|---|
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142,464 | 3-(4,6-dimethoxy-1,3,5-triazin-2-yl)-1-[2-(2-methoxyethoxy)-phenyl-sulfonyl]-urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]-amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitrophenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]-phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]-propanoic acid, methyl ester |
| diethatyl | N-(chloroacetyl)-N-(2,6-diethylphenyl)-glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb (SC2957) | S-benzyl-N-ethyl-N-(1,2-dimethyl)-propyl)thiolcarbamate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]-carbonyl] amino]sulfonyl]]benzoic acid, methyl ester |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |

-continued

| Common Name | Chemical Name |
|---|---|
| fomesafen | 5-[2-chloro-4-(trifluoromethyl)phenoxy]-N-(methylsulfonyl)-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazametha-benz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl] -3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothionate |
| mecoprop | (±)-2-(4-chloro-2-methylphenoxy)-propanoic acid |
| mefenacet | 2-(2-benzothiazolyloxy-N-methyl-N-phenylacetamide |
| mefluidide | N-[2,4-dimethyl-5-[[(trifluoromethyl)-sulfonyl]amino]phenyl]acetamide |
| methal-propalin | N-(2-methyl-2-propenyl)-2,6-dinitro-N-propyl-4-(trifluoromethyl)benzenamide |
| methabenz-thiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[((1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dihemthyl-N',-(octahydro-4,7-methano-1H-inden-5-yl)urea 3aα,-4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridine-carboxylic acid |
| PPG-1013 | 5-[2-chloro-4-(trifluoromethyl)-phenoxy]-2-nitroacetophenone oxime-O-acetic acid, methyl ester |
| pretilachlor | α-chloro-2,6-diethyl-N-(2-propoxyethyl)acetanilide |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitro-phenyl]sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethyl-pyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(α,α-dimethylbenzyl)-3-(4-methylphenyl)urea |

-continued

| Common Name | Chemical Name |
|---|---|
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-toyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl] diethylcarbamothioate |
| triallate | S-(2,3,3-trichloro-2-propenyl) bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test results and procedures follow.

COMPOUNDS

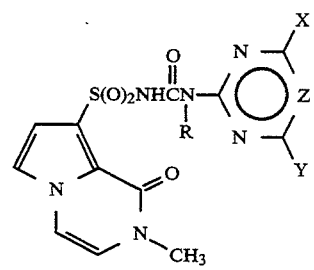

| COMPOUND | R | X | Y | Z | m.p. (°C.) |
|---|---|---|---|---|---|
| 1 | H | OCH3 | OCH3 | CH | 221-223 (d) |
| 2 | H | CH3 | OCH3 | N | 204-207 (d) |
| 3 | H | CH3 | CH3 | CH | 202-205 (d) |
| 4 | H | OCH3 | CH3 | CH | 195-197 (d) |
| 5 | H | OCH3 | OCH3 | N | 208-210 (d) |
| 6 | H | Cl | OCH3 | CH | 197-200 (d) |
| 7 | H | NHCH3 | OCH2CH3 | N | 234-237 (d) |

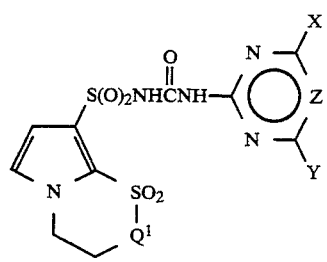

| COMPOUND | R | X | Y | Z | m.p. (°C.) |
|---|---|---|---|---|---|
| 8 | H | CH3 | OCH3 | CH | 225-227 (d) |
| 9 | H | OCH3 | OCH3 | CH | 206-210 (d) |
| 10 | H | OCH3 | CH3 | N | 209-212 (d) |
| 11 | H | OCH3 | OCH3 | N | 167-169 (d) |
| 12 | H | Cl | OCH3 | CH | 118-125 (d) |

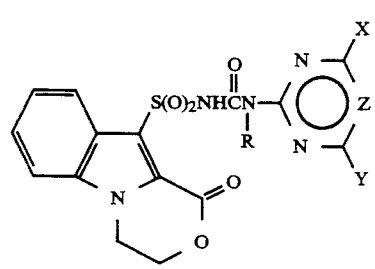

| COMPOUND | R | X | Y | Z | m.p. (°C.) |
|---|---|---|---|---|---|
| 13 | H | CH3 | OCH3 | CH | 95-98 (d) |
| 14 | H | OCH3 | OCH3 | CH | 173-175 (d) |
| 15 | H | CH3 | OCH3 | N | 160-162 (d) |
| 16 | H | OCH3 | OCH3 | N | 157-161 (d) |
| 17 | H | Cl | OCH3 | CH | 195-198 (d) |

| COMPOUND | Q¹ | X | Y | Z | m.p. (°C.) |
|---|---|---|---|---|---|
| 18 | NCH3 | CH3 | OCH3 | CH | 230-231 (d) |
| 19 | NCH3 | OCH3 | OCH3 | CH | 226-229 (d) |
| 20 | NCH3 | CH3 | OCH3 | N | 225-227 (d) |
| 21 | NCH3 | OCH3 | OCH3 | N | 217-219 (d) |
| 22 | NCH3 | Cl | OCH3 | N | 221-224 (d) |
| 23 | NCH2CH2CH2CH3 | CH3 | OCH3 | CH | 108-110 (d) |
| 24 | NCH2CH2CH2CH3 | OCH3 | OCH3 | CH | 112-114 (d) |
| 25 | NCH2CH2CH2CH3 | CH3 | OCH3 | N | 124-125 (d) |
| 26 | NCH2CH2CH2CH3 | OCH3 | OCH3 | N | 117-179 (d) |
| 27 | NCH2CH3 | CH3 | CH3 | CH | 205-207 (d) |
| 28 | NCH2CH3 | OCH3 | CH3 | CH | 210-212 (d) |
| 29 | NCH2CH3 | OCH3 | OCH3 | CH | 211-213 (d) |
| 30 | NCH2CH3 | CH3 | OCH3 | N | 201-203 (d) |
| 31 | NCH2CH3 | OCH3 | OCH3 | N | 184-186 (d) |
| 32 | NCH2CH3 | Cl | OCH3 | CH | 198-200 (d) |
| 33 | NCH2CH3 | OC2H5 | NHCH3 | N | 164-166 (d) |

-continued

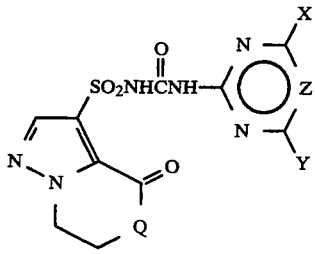

| COMPOUND | Q | X | Y | Z | m.p. (°C.) |
|---|---|---|---|---|---|
| 34 | O | CH$_3$ | CH$_3$ | CH | 206–208 (d) |
| 35 | O | CH$_3$ | OCH$_3$ | CH | 183–193 (d) |
| 36 | O | OCH$_3$ | OCH$_3$ | CH | 208–209 (d) |
| 37 | O | CH$_3$ | OCH$_3$ | N | 021–206 (d) |
| 38 | O | OCH$_3$ | OCH$_3$ | N | 207–208 (d) |
| 39 | O | Cl | OCH$_3$ | CH | 200–202 (d) |
| 40 | O | NHCH$_3$ | OC$_2$H$_5$ | N | 189–191 (d) |
| 41 | NCH$_3$ | CH$_3$ | OCH$_3$ | CH | 187–189 (d) |
| 42 | NCH$_3$ | OCH$_3$ | OCH$_3$ | CH | 214–216 (d) |
| 43 | NCH$_3$ | CH$_3$ | OCH$_3$ | N | 70–74 (d) |
| 44 | NCH$_3$ | OCH$_3$ | OCH$_3$ | N | 205–207 (d) |

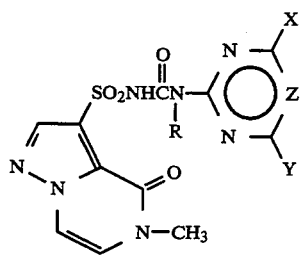

| COMPOUND | R | X | Y | Z | m.p. (°C.) |
|---|---|---|---|---|---|
| 45 | H | CH$_3$ | CH$_3$ | CH | 231–233 (d) |
| 46 | H | CH$_3$ | OCH$_3$ | CH | 191–194 (d) |
| 47 | H | OCH$_3$ | OCH$_3$ | CH | 188–192 (d) |
| 48 | H | OCH$_3$ | CH$_3$ | N | 207–208 (d) |
| 49 | H | OCH$_3$ | OCH$_3$ | N | 166–172 (d) |
| 50 | H | Cl | OCH$_3$ | CH | 198–202 (d) |

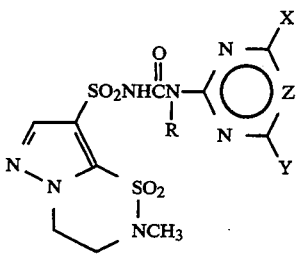

-continued

| COMPOUND | R | X | Y | Z | m.p. (°C.) |
|---|---|---|---|---|---|
| 51 | H | CH$_3$ | OCH$_3$ | CH | 149–150 (d) |
| 52 | H | OCH$_3$ | OCH$_3$ | CH | 219–220 (d) |
| 53 | H | CH$_3$ | OCH$_3$ | N | 199–200 (d) |
| 54 | H | OCH$_3$ | OCH$_3$ | N | 186–187 (d) |

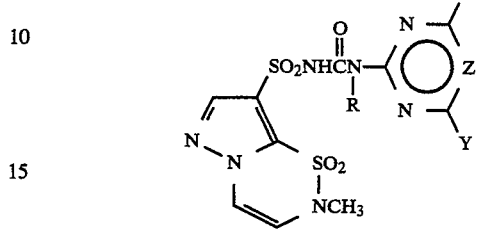

| COMPOUND | R | X | Y | Z | m.p. (°C.) |
|---|---|---|---|---|---|
| 55 | H | CH$_3$ | CH$_3$ | CH | 209–210 (d) |
| 56 | H | OCH$_3$ | OCH$_3$ | CH | 215–216 (d) |
| 57 | H | OCH$_3$ | OCH$_3$ | N | 204–205 (d) |
| 58 | H | Cl | OCH$_3$ | CH | 200–201 (d) |
| 59 | H | CH$_3$ | OCH$_3$ | CH | 142–143 (d) |
| 60 | H | CH$_3$ | OCH$_3$ | N | 143–145 (d) |

(d) Indicates melting with apparent decomposition.

TEST A

Seeds of barely (*Hordeum vulgare*), barnyardgrass (*Echinochloa crus-galli*), cheatgrass (*Bromus secalinus*), cocklebur (*Xanthium pensylvanicum*), corn (*Zea mays*), cotton (*Gossypium hirsutum*), crabgrass (*Digitaria* spp.), giant foxtail (*Setaria faberi*), morningglory (*Ipomoea* spp.), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a nonphytotoxic solvent. At the same time, these crop and weed species were also treated with postemergence applications of test chemicals. Plants ranged in height from two to eighteen cm (two to three leaf stage) for postemergence treatments.

Treated plants and controls were maintained in a greenhouse for approximately sixteen days, after which all species were compared to controls and visually evaluated. Plant response ratings, summarized in Table A, are based on a scale of 0 to 10 where 0 is no effect and 10 is complete control. A dash (—) response means no test result.

TABLE A

| Rate (50 g/ha) | COMPOUND | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| POSTEMERGENCE | | | | | | | | | | | | | | | | | | | | | | |
| Barley | 9 | 9 | 9 | 9 | 10 | 8 | 3 | 9 | 9 | 9 | 9 | 8 | 9 | 9 | 9 | 9 | 0 | 9 | 9 | 7 | 9 | 9 |
| Barnyardgrass | 10 | 9 | 9 | 10 | 6 | 9 | 0 | 9 | 9 | 9 | 9 | 9 | 9 | 9 | 9 | 9 | 9 | 9 | 9 | 3 | 7 | 9 |
| Cheatgrass | 9 | 9 | 9 | 10 | 10 | 9 | 7 | 9 | 9 | 9 | 9 | 9 | 9 | 9 | 9 | 9 | 5 | 8 | 9 | 9 | 9 | 9 |
| Cocklebur | 10 | 9 | 9 | 9 | 9 | 9 | 0 | — | — | 9 | 9 | — | 9 | 9 | 5 | 1 | 1 | 9 | 9 | 9 | 8 | 10 |
| Corn | 9 | 9 | 9 | 10 | 8 | 9 | 3 | 10 | 9 | 9 | 9 | 9 | 9 | 9 | 9 | 9 | 9 | 9 | 9 | 9 | 9 | 9 |
| Cotton | 9 | 3 | 9 | 9 | 0 | 9 | 0 | 2 | 10 | 9 | 2 | 2 | 9 | 9 | 9 | 8 | 7 | 10 | 10 | 9 | 9 | 9 |
| Crabgrass | 9 | 9 | 9 | 9 | 4 | 10 | 0 | 9 | 9 | 9 | 9 | 9 | 7 | 9 | 8 | 9 | 3 | 10 | 10 | 2 | 5 | 10 |
| Giant foxtail | 9 | 9 | 9 | 9 | 9 | 9 | — | 8 | 9 | 7 | 7 | 6 | 9 | 9 | 9 | 8 | 8 | 9 | 9 | 9 | 8 | 9 |
| Morningglory | 9 | 7 | 9 | 9 | 1 | 10 | 0 | 8 | 9 | 10 | 9 | 8 | 9 | 10 | 8 | 6 | 5 | 9 | 10 | 5 | 4 | 10 |
| Nutsedge | — | 6 | — | 9 | 2 | 10 | 0 | 9 | 2 | 9 | 9 | 9 | 8 | 5 | 5 | 0 | 0 | 10 | 10 | 5 | 4 | 10 |
| Rice | 9 | 9 | 9 | 9 | 9 | 9 | 7 | 9 | 9 | 9 | 9 | 9 | 9 | 9 | 9 | 9 | 9 | 9 | 9 | 6 | 9 | 9 |
| Sorghum | 9 | 9 | 9 | 9 | 9 | 9 | 6 | 9 | 9 | 9 | 9 | 9 | 9 | 9 | 9 | 9 | 9 | 9 | 9 | 9 | 9 | 10 |
| Soybean | 9 | 2 | 9 | 9 | 0 | 9 | 0 | 8 | 8 | 9 | 9 | 4 | 7 | 9 | 9 | 9 | 0 | 9 | 9 | 4 | 7 | 9 |
| Sugar beet | 10 | 9 | 9 | 10 | 9 | 9 | 6 | 9 | 9 | 9 | 7 | 9 | 9 | 10 | 9 | 8 | 3 | 10 | 10 | 9 | 9 | 9 |
| Velvetleaf | 10 | 3 | 9 | 9 | 0 | 9 | 0 | 2 | 3 | 9 | 7 | 7 | 9 | 10 | 7 | 8 | 6 | 9 | 9 | 5 | 7 | 9 |

TABLE A-continued

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| Wheat | 9 | 9 | 8 | 9 | 7 | 8 | 6 | 9 | 9 | 9 | 9 | 9 | 8 | 9 | 9 | 9 | 0 | 9 | 9 | 9 | 9 | 9 |
| Wild oat | 9 | 9 | 9 | 10 | 10 | 8 | 8 | 9 | 9 | 9 | 9 | 9 | 9 | 9 | 9 | 9 | 0 | 9 | 9 | 9 | 9 | 8 |
| PREEMERGENCE | | | | | | | | | | | | | | | | | | | | | | |
| Barley | 9 | 7 | 6 | 8 | 0 | 7 | 0 | 5 | 2 | 7 | 0 | 2 | 0 | 0 | 0 | 0 | 0 | 0 | 8 | 0 | 0 | 9 |
| Barnyardgrass | 9 | 7 | 3 | 4 | 0 | 8 | 0 | 9 | 9 | 9 | 3 | 6 | 0 | 7 | 0 | 0 | 0 | 2 | 0 | 1 | 1 | 3 |
| Cheatgrass | 8 | 7 | 7 | 8 | 6 | 8 | 0 | 7 | 6 | 8 | 0 | 4 | 0 | 7 | 1 | 0 | 0 | 7 | 9 | 0 | 0 | 9 |
| Cocklebur | 9 | — | 1 | 9 | 7 | 8 | 0 | 1 | 3 | 6 | 1 | 0 | 0 | — | — | 4 | 0 | 3 | — | 5 | 3 | 2 |
| Corn | 9 | 7 | 9 | 9 | 0 | 9 | 0 | 9 | 2 | 8 | 2 | 3 | 0 | 2 | 1 | 2 | 1 | 7 | 8 | 2 | 0 | 9 |
| Cotton | 8 | 0 | 0 | 0 | 0 | 0 | 0 | 5 | 5 | 8 | 2 | 2 | 0 | 2 | 0 | 0 | 0 | 2 | 5 | 0 | 0 | 0 |
| Crabgrass | 9 | 5 | 9 | 9 | 1 | 9 | 0 | 8 | 8 | 8 | 9 | 8 | 0 | 9 | 2 | 0 | 0 | 5 | 9 | 6 | 4 | 9 |
| Giant foxtail | 9 | 9 | 9 | 9 | 6 | 9 | 2 | 7 | 8 | 5 | 2 | 2 | 0 | 8 | 2 | 2 | 2 | 5 | 9 | 4 | 2 | 9 |
| Morningglory | 9 | 0 | 9 | 9 | 0 | 8 | 0 | 4 | 0 | 9 | 8 | 7 | 0 | 0 | 0 | 0 | 0 | 2 | 2 | 0 | 1 | 2 |
| Nutsedge | 9 | 0 | 9 | 10 | 0 | 9 | 0 | 6 | 0 | 7 | 0 | 0 | 0 | 0 | 0 | 0 | 0 | 5 | 9 | 0 | 0 | 0 |
| Rice | 9 | 8 | 9 | 9 | 8 | 9 | 0 | 8 | 0 | 8 | 4 | 9 | 0 | 8 | 2 | 3 | 0 | 9 | 9 | 2 | 5 | 9 |
| Sorghum | 9 | 8 | 9 | 9 | 2 | 9 | 0 | 9 | 5 | 9 | 8 | 9 | 1 | 8 | 1 | 2 | 1 | 2 | 9 | 0 | 0 | 9 |
| Soybean | 8 | 1 | 2 | 6 | 0 | 5 | 0 | 4 | 0 | 3 | 2 | 5 | 1 | 2 | 1 | 0 | 2 | 3 | 8 | 3 | 4 | 5 |
| Sugar beet | 9 | 8 | 9 | 9 | 0 | 9 | 0 | 8 | 8 | 9 | 8 | 8 | 3 | 8 | 2 | 2 | 2 | 6 | 8 | 0 | 0 | 9 |
| Velvetleaf | 9 | 0 | 6 | 8 | 0 | 8 | 3 | 7 | 8 | 9 | 8 | 6 | 0 | 4 | 1 | 0 | 0 | 0 | 2 | 1 | 0 | 2 |
| Wheat | 8 | 7 | 4 | 7 | 0 | 2 | 0 | 7 | 2 | 8 | 6 | 3 | 0 | 3 | 0 | 0 | 0 | 4 | 8 | 3 | 0 | 8 |
| Wild oat | 8 | 2 | 5 | 7 | 3 | 3 | 0 | 6 | 2 | 5 | 2 | 4 | 0 | 2 | 0 | 2 | 0 | 0 | 5 | 0 | 0 | 1 |

| | COMPOUND | | | | | | | | | | | | | | | | | | | | | |
|---|---|---|---|---|---|---|---|---|---|---|---|---|---|---|---|---|---|---|---|---|---|---|
| Rate (10 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| POSTEMERGENCE | | | | | | | | | | | | | | | | | | | | | | |
| Barley | 9 | 9 | 7 | 9 | 8 | 7 | 0 | 8 | 7 | 9 | 9 | 6 | 7 | 9 | 3 | 8 | 0 | 9 | 9 | 0 | 1 | 9 |
| Barnyardgrass | 9 | 9 | 6 | 10 | 0 | 9 | 0 | 9 | 9 | 9 | 9 | 9 | 5 | 9 | 8 | 7 | 7 | 7 | 9 | 0 | 0 | 8 |
| Cheatgrass | 9 | 9 | 8 | 10 | 5 | 9 | 3 | 8 | 7 | 9 | 9 | 8 | 2 | 9 | 8 | 8 | 3 | 9 | 9 | 5 | 6 | 9 |
| Cocklebur | 9 | 7 | 9 | 9 | 1 | 9 | 0 | 5 | 6 | 9 | 8 | 4 | 5 | 9 | 0 | 1 | 1 | 9 | 9 | 3 | 5 | 9 |
| Corn | 10 | 9 | 9 | 9 | 8 | 9 | 0 | 9 | 9 | 9 | 9 | 9 | 9 | 9 | 8 | 9 | 9 | 9 | 9 | 4 | 4 | 9 |
| Cotton | 9 | 0 | 6 | 8 | 0 | 8 | 0 | 0 | 0 | 3 | 0 | 0 | 3 | 8 | 1 | 0 | 1 | 9 | 9 | 3 | 5 | 9 |
| Crabgrass | 9 | 3 | 8 | 9 | 0 | 8 | 0 | 7 | 9 | 9 | 9 | 3 | 7 | 8 | 5 | 2 | 0 | 7 | 10 | 0 | 0 | 9 |
| Giant foxtail | 9 | 9 | 9 | 9 | 9 | 9 | 6 | 7 | 9 | 5 | 1 | 0 | 6 | 9 | 3 | 8 | 2 | 7 | 8 | 7 | 3 | 9 |
| Morningglory | 10 | 2 | 9 | 9 | 0 | 9 | 0 | 7 | 5 | 9 | 3 | 5 | 9 | 9 | 2 | 1 | 1 | 9 | 10 | 1 | 0 | 9 |
| Nutsedge | 10 | 0 | 5 | 9 | — | — | 0 | 0 | 0 | 9 | 0 | 0 | 3 | 9 | 0 | 0 | 0 | 5 | 6 | 0 | 0 | 5 |
| Rice | 9 | 9 | 9 | 9 | 9 | 9 | 3 | 8 | 9 | 9 | 9 | 8 | 9 | 9 | 9 | 9 | 5 | 7 | 9 | 8 | 7 | — |
| Sorghum | 10 | 8 | 9 | 9 | 9 | 9 | 0 | 8 | 9 | 9 | 8 | 8 | 9 | 9 | 9 | 9 | 8 | 9 | 9 | 8 | 7 | 9 |
| Soybean | 9 | 0 | 8 | 9 | 0 | 8 | 0 | 5 | 5 | 8 | 7 | 1 | 1 | 8 | 1 | 3 | 0 | 7 | 8 | 2 | 2 | 4 |
| Sugar beet | 9 | 8 | 9 | 9 | 6 | 9 | 2 | 7 | 9 | 9 | 2 | 7 | 8 | 9 | 3 | 7 | 3 | 9 | 9 | 3 | 6 | 9 |
| Velvetleaf | 9 | 0 | 9 | 9 | 0 | 9 | 0 | 0 | 0 | 8 | 0 | 0 | 7 | 9 | 3 | 4 | 2 | 9 | 9 | 3 | 0 | 9 |
| Wheat | 9 | 9 | 6 | 6 | 7 | 0 | 0 | 9 | 8 | 9 | 9 | 8 | 7 | 9 | 9 | 9 | 0 | 9 | 9 | 6 | 4 | 7 |
| Wild oat | 9 | 8 | 9 | 9 | 9 | 2 | 7 | 9 | 9 | 9 | 9 | 7 | 4 | 9 | 7 | 9 | 0 | 9 | 9 | 6 | 9 | 3 |
| PREEMERGENCE | | | | | | | | | | | | | | | | | | | | | | |
| Barley | 8 | 2 | 0 | 3 | 0 | 0 | 0 | 0 | 0 | 2 | 0 | 0 | 0 | 0 | 0 | 0 | 0 | 0 | 5 | 0 | 0 | 5 |
| Barnyardgrass | 2 | 2 | 0 | 2 | 0 | 0 | 0 | 2 | 0 | 7 | 2 | 0 | 0 | 0 | 0 | 0 | 0 | 0 | 0 | 0 | 0 | 0 |
| Cheatgrass | 7 | 2 | 4 | 6 | 3 | 4 | 0 | 0 | 0 | 7 | 2 | 0 | 0 | 3 | 0 | 0 | 0 | 2 | 6 | 0 | 0 | 2 |
| Cocklebur | — | 7 | 0 | — | — | 0 | — | 0 | 0 | 5 | 0 | 0 | 0 | 0 | 0 | 0 | 0 | 0 | 0 | 0 | 0 | 4 |
| Corn | 8 | 2 | 2 | 8 | 0 | 7 | 0 | 0 | 0 | 2 | 1 | 0 | 0 | 0 | 0 | 0 | 0 | 0 | 0 | 0 | 0 | 3 |
| Cotton | 3 | 0 | 0 | 0 | 0 | 0 | 0 | 0 | 0 | 2 | 0 | 0 | 0 | 0 | 0 | 0 | 0 | 0 | 0 | 0 | 0 | 0 |
| Crabgrass | 8 | 0 | 2 | 8 | 0 | 9 | 0 | 5 | 4 | 5 | 5 | 8 | 0 | 6 | 0 | 0 | 0 | 2 | 8 | 0 | 0 | 0 |
| Giant foxtail | 9 | 0 | 4 | 8 | 0 | 8 | 0 | 0 | 0 | 2 | 0 | 0 | 3 | 0 | 0 | 0 | 0 | 0 | 2 | 0 | 0 | 0 |
| Morningglory | 8 | 0 | 0 | 7 | 0 | 1 | 0 | 1 | 0 | 2 | 2 | 3 | 0 | 0 | 0 | 0 | 0 | 0 | 0 | 0 | 0 | 3 |
| Nutsedge | 8 | — | 9 | 0 | 0 | 0 | 0 | 0 | 2 | 5 | 0 | 0 | 0 | 0 | 0 | 0 | 0 | 0 | 0 | 0 | 0 | 0 |
| Rice | 9 | 4 | 6 | 9 | 0 | 8 | 0 | 0 | 0 | 3 | 0 | 2 | 0 | 3 | 0 | 0 | 0 | 3 | 5 | 0 | 0 | 8 |
| Sorghum | 9 | 1 | 2 | 9 | 0 | 9 | 0 | 2 | 0 | 5 | 2 | 3 | 0 | 2 | 0 | 0 | 0 | 0 | 0 | 0 | 0 | 8 |
| Soybean | 7 | 0 | 0 | 3 | 0 | 0 | 0 | 0 | 0 | 0 | 3 | 0 | 0 | 0 | 0 | 0 | 0 | 2 | 3 | 0 | 0 | 5 |
| Sugar beet | 5 | 7 | 3 | 8 | 0 | 7 | 0 | 3 | 7 | 6 | 5 | 6 | 0 | 5 | 0 | 0 | 0 | 2 | 2 | 0 | 0 | 3 |
| Velvetleaf | 7 | 0 | 0 | 3 | 0 | 2 | 2 | 3 | 3 | 4 | 1 | 5 | 0 | 0 | 0 | 0 | 0 | 0 | 0 | 0 | 0 | 0 |
| Wheat | 8 | 2 | 0 | 6 | 0 | 0 | 0 | 0 | 0 | 3 | 2 | 0 | 0 | 0 | 0 | 0 | 0 | 0 | 2 | 0 | 0 | 0 |
| Wild oat | 6 | 2 | 2 | 2 | 0 | 0 | 0 | 0 | 0 | 2 | 0 | 0 | 0 | 0 | 0 | 0 | 0 | 0 | 2 | 0 | 0 | 0 |

Test B

Seeds of barley (Hordeum vulgare), barnyardgrass (Echinochloa crus-galli), blackgrass (Alopecurus myosuroides), cheatgrass (Bromus secalinus), chickweed (Stellaria media), cocklebur (Xanthium pensylvanicum), corn (Zea mays), cotton (Gossypium hirsutum), crabgrass (Digitaria spp.), bedstraw (Galium aparine), giant foxtail (Setaria faberii), lambsquarters (Chenopodium album), morningglory (Ipomoea hederacea), rape (Brassica napus), rice (Oryza sativa), sorghum (Sorghum bicolor), soybeam (Glycine max), sugar beet (Beta vulgaris), velvetleaf (Abutilon theophrasti), wheat (Triticum aestivum), wild buckwheat (Polygonum convolvulus), and wild oat (Avena fatua) and purple nutsedge (Cyperus rotundus) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments.

Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (—) response means no test result.

TABLE B

| Rate (50 g/ha) | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|---|---|---|---|---|---|---|---|
| POSTEMERGENCE ||||||||||||||||||||||||||||||||||||||
| Barley | 0 | 0 | 0 | 0 | 7 | 9 | 9 | 9 | 9 | 7 | 8 | 0 | 0 | 0 | 0 | 0 | 0 | 0 | 6 | 9 | 0 | 0 | 0 | 9 | 9 | 2 | 8 | 2 | 9 | 9 | 6 | 6 | 8 | 9 | 6 | 8 | 9 | 6 |
| Barnyardgrass | 0 | 1 | 0 | 0 | 2 | 8 | 9 | 9 | 9 | 8 | 7 | 0 | 0 | 0 | 1 | 0 | 0 | 0 | 5 | 9 | 2 | 0 | 0 | 9 | 9 | 3 | 7 | 6 | 9 | 10 | 4 | 8 | 9 | 9 | 9 | 9 | 9 | 9 |
| Bedstraw | 0 | 0 | 0 | 0 | 3 | 7 | 8 | 7 | 7 | 7 | 3 | 0 | 0 | 0 | 0 | 0 | 0 | 0 | 3 | 6 | 0 | 0 | 0 | 8 | 9 | 2 | 2 | 2 | 8 | 10 | 5 | 5 | 10 | 10 | 7 | 10 | 9 | 5 |
| Blackgrass | 3 | 2 | 0 | 0 | 5 | 9 | 9 | 10 | 9 | 10 | 8 | 0 | 0 | 1 | 0 | 0 | 0 | 0 | 5 | 9 | 2 | 4 | 0 | 9 | 9 | 8 | 9 | 0 | 9 | 9 | 8 | 8 | 9 | 9 | 9 | 8 | 9 | 9 |
| Cheatgrass | 1 | 2 | 0 | 0 | 4 | 9 | 9 | 9 | 9 | 8 | 8 | 0 | 0 | 1 | 0 | 0 | 0 | 0 | 6 | 9 | 0 | 0 | 0 | 9 | 10 | 5 | 8 | 0 | 10 | 10 | 2 | 7 | 10 | 9 | 9 | 8 | 10 | 8 |
| Chickweed | 0 | 0 | 0 | 0 | 5 | 7 | 10 | 9 | 9 | 2 | 8 | 0 | 2 | 0 | 2 | 2 | 3 | 0 | 4 | 9 | 0 | 0 | 0 | 9 | 9 | 0 | 4 | 7 | 10 | 10 | 5 | 6 | 10 | 10 | 8 | 10 | 10 | 7 |
| Cocklebur | — | 0 | 0 | 0 | — | — | — | — | — | — | — | 0 | 0 | 0 | 0 | 0 | 0 | 0 | 7 | 9 | 0 | 0 | 3 | 10 | 10 | 1 | 0 | 9 | 10 | 10 | — | — | 10 | 10 | — | 10 | 10 | — |
| Corn | 0 | 6 | 0 | 0 | 5 | 9 | 9 | 9 | 9 | 9 | 9 | 0 | 0 | 1 | 2 | 2 | 0 | 0 | 7 | 9 | 0 | 0 | 0 | 9 | 9 | 6 | 9 | 4 | 9 | 9 | 9 | 9 | 9 | 10 | 9 | 9 | 9 | 9 |
| Cotton | 1 | 0 | 0 | 0 | 0 | 9 | 9 | 3 | 4 | 9 | 2 | 3 | 0 | 0 | 0 | 0 | 0 | 0 | 2 | 9 | 0 | 0 | 0 | 8 | 9 | 5 | 0 | 0 | 9 | 10 | 5 | 3 | 9 | 7 | 1 | 5 | 9 | 5 |
| Crabgrass | 0 | 2 | 0 | 0 | 0 | 6 | 8 | 3 | 7 | 7 | 1 | 2 | 0 | 0 | 0 | 0 | 0 | 0 | 2 | 9 | 0 | 0 | 0 | 8 | 9 | 6 | 2 | 4 | 9 | 9 | 3 | 0 | 9 | 7 | 2 | 5 | 8 | 8 |
| Giant foxtail | 0 | 0 | 0 | 0 | 5 | 9 | 9 | 9 | 8 | 3 | 8 | 0 | 0 | 0 | 2 | 2 | 0 | 0 | 2 | 8 | 2 | 0 | 0 | 8 | 9 | 6 | 9 | 4 | 8 | 9 | 7 | 0 | 10 | 7 | 8 | 5 | 9 | 4 |
| Lambsquarters | 3 | 2 | 0 | 0 | 7 | 9 | 9 | 4 | 5 | 8 | 5 | 0 | 0 | 0 | 0 | 0 | 0 | — | 7 | 9 | 0 | 0 | 0 | 9 | 10 | 0 | 0 | 7 | 9 | 10 | 2 | 0 | 9 | 10 | 2 | 10 | 9 | 4 |
| Morningglory | 0 | 3 | 0 | 0 | 0 | 9 | 9 | 9 | 8 | 9 | 1 | 1 | 0 | 0 | 0 | 0 | 0 | 0 | 9 | 9 | 1 | 1 | 0 | 9 | 10 | 1 | 0 | 2 | 10 | 10 | 2 | 1 | 9 | 9 | 2 | 9 | 9 | 2 |
| Nutsedge | 0 | 7 | 2 | 2 | 0 | 2 | 9 | 0 | 3 | 3 | 0 | 0 | 0 | 0 | 5 | 0 | 0 | 0 | 9 | 9 | 0 | 0 | 0 | 7 | 9 | 0 | 2 | 0 | 8 | 8 | 0 | 0 | 8 | 8 | 2 | 5 | 5 | 0 |
| Rape | 1 | 7 | 0 | 0 | 7 | 10 | 10 | 8 | 9 | 10 | 9 | 0 | 0 | 0 | 0 | 0 | 0 | 0 | 9 | 9 | 0 | 0 | 1 | 9 | 9 | 3 | 9 | 8 | 10 | 9 | 8 | 7 | 10 | 9 | 8 | 10 | 10 | 10 |
| Rice | 0 | 2 | 0 | 0 | 3 | 9 | 9 | 9 | 9 | 9 | 9 | 0 | 0 | 0 | 0 | 0 | 0 | 0 | 9 | 9 | 0 | 0 | 0 | 9 | 9 | 3 | 9 | 9 | 9 | 9 | 9 | 9 | 9 | 9 | 9 | 9 | 9 | 9 |
| Sorghum | 0 | 2 | 0 | 0 | 7 | 9 | 7 | 7 | 8 | 3 | 9 | 0 | 0 | 0 | 0 | 0 | 0 | 0 | 9 | 9 | 2 | 0 | 0 | 9 | 9 | 7 | 9 | 8 | 9 | 9 | 8 | 8 | 9 | 9 | 7 | 9 | 9 | 8 |
| Soybean | 1 | 2 | 5 | 0 | 1 | 7 | 9 | 3 | 3 | 3 | 3 | 0 | 0 | 0 | 2 | 2 | 3 | 0 | 8 | 9 | 4 | 0 | 3 | 9 | 9 | 1 | 1 | 1 | 9 | 9 | 5 | 5 | 9 | 9 | 8 | 10 | 9 | 8 |
| Sugar beet | 1 | 2 | 0 | 0 | 2 | 7 | 9 | 3 | 2 | 8 | 1 | 0 | 0 | 0 | 0 | 2 | 0 | 0 | 6 | 9 | 0 | 0 | 0 | 9 | 9 | 1 | 0 | 6 | 9 | 9 | 7 | 4 | 9 | 9 | 5 | 10 | 9 | 4 |
| Velvetleaf | 0 | 0 | 0 | 0 | 7 | 9 | 9 | 9 | 9 | 2 | 8 | 0 | 0 | 0 | 2 | 2 | 0 | 0 | 6 | 9 | 0 | 0 | 0 | 9 | 9 | 0 | 0 | 3 | 9 | 9 | 1 | 0 | 9 | 9 | 5 | 10 | 9 | 4 |
| Wheat | 0 | 0 | 0 | 0 | 2 | 7 | 9 | 3 | 6 | 9 | 0 | 0 | 0 | 0 | 2 | 3 | 0 | 0 | 4 | 8 | 0 | 0 | 0 | 9 | 9 | 0 | 2 | 5 | 9 | 9 | 7 | 9 | 9 | 10 | 6 | 7 | 9 | 7 |
| Wild buckwheat | 0 | 0 | 0 | 0 | 2 | 7 | 9 | 9 | 9 | 9 | 8 | 0 | 0 | 1 | 0 | 0 | 0 | 0 | 4 | 8 | 0 | 0 | 0 | 9 | 9 | 0 | 2 | 0 | 9 | 9 | — | 0 | 9 | 9 | 7 | 10 | 9 | 10 |
| Wild oat | 1 | 5 | 0 | 0 | 5 | 9 | 10 | 10 | 10 | 0 | 0 | 0 | 0 | 0 | 0 | 0 | 0 | 0 | 0 | 9 | 0 | 0 | 0 | 9 | 10 | 0 | 0 | 0 | 10 | 9 | 8 | 9 | 9 | 9 | 7 | 2 | 9 | 4 |
| PREEMERGENCE ||||||||||||||||||||||||||||||||||||||
| Barley | 0 | 0 | 0 | 0 | 0 | 0 | 7 | 0 | 0 | 0 | 0 | 0 | 0 | 0 | 0 | 1 | 0 | 0 | 3 | 9 | 0 | 0 | 0 | 0 | 0 | 0 | 0 | 0 | 8 | 9 | 0 | 2 | 8 | 0 | 4 | 7 | 8 | 2 |
| Barnyardgrass | 0 | 0 | 0 | 0 | 0 | 1 | 6 | 0 | 0 | 4 | 0 | 0 | 0 | 0 | 0 | 0 | 0 | 0 | 2 | 0 | 0 | 0 | 0 | 0 | 6 | 0 | 0 | 0 | 8 | 9 | 1 | 0 | 9 | 8 | 7 | 9 | 9 | 2 |
| Bedstraw | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 6 | 0 | 2 | 0 | 0 | 0 | 2 | 6 | 0 | 0 | 2 | 8 | 0 | 7 | 4 | 7 |
| Blackgrass | 2 | 0 | 0 | 0 | 0 | 8 | 9 | — | — | 0 | 0 | 0 | 0 | 0 | 4 | 4 | 0 | 4 | 0 | 4 | 2 | 2 | 0 | 2 | 8 | 0 | 0 | 0 | 8 | 9 | 4 | 4 | 9 | 7 | 0 | 8 | 9 | 0 |
| Cheatgrass | 0 | 0 | 0 | 0 | 0 | 5 | 9 | 3 | 3 | 3 | 0 | 0 | 0 | 0 | 0 | 0 | 0 | 0 | 0 | — | 2 | 2 | 0 | 7 | 6 | 0 | 0 | 0 | 9 | 9 | 6 | 7 | 9 | 9 | 0 | 9 | 9 | 9 |
| Chickweed | 3 | 0 | 0 | 0 | 6 | 9 | 8 | 7 | 2 | 4 | 0 | 0 | 0 | 0 | 0 | 0 | 0 | 0 | 0 | 1 | 0 | 0 | 0 | 8 | 4 | 0 | 0 | 0 | 9 | 9 | 2 | 2 | 8 | 9 | 9 | 9 | 9 | 7 |
| Cocklebur | — | — | — | — | — | — | — | — | — | — | — | 0 | 0 | 0 | 0 | 0 | 0 | 0 | 0 | — | 0 | 0 | 0 | 0 | 7 | 0 | 0 | 0 | — | — | 0 | 0 | — | — | — | — | — | — |
| Corn | 0 | 0 | 0 | 0 | 3 | 3 | 9 | 3 | 0 | 4 | 0 | 0 | 0 | 0 | 4 | 4 | 0 | 4 | 0 | 4 | 2 | 2 | 0 | 2 | 8 | 0 | 0 | 0 | 9 | 9 | 4 | 4 | 9 | 7 | 0 | 8 | 9 | 0 |
| Cotton | 0 | 0 | 0 | 0 | 1 | 1 | 0 | 0 | 0 | 0 | 0 | 0 | 0 | 0 | 0 | 0 | 0 | 0 | 0 | 1 | 2 | 2 | 0 | 7 | 6 | 0 | 0 | 0 | 9 | 9 | 6 | 7 | 9 | 9 | 0 | 9 | 9 | 9 |
| Crabgrass | 0 | 0 | 0 | 0 | 6 | 6 | 8 | 7 | 2 | 4 | 2 | 0 | 0 | 0 | 0 | 0 | 0 | 0 | 0 | 1 | 0 | 0 | 0 | 0 | 4 | 0 | 0 | 0 | 7 | 9 | 6 | 2 | 9 | 9 | 9 | 9 | 9 | 3 |
| Giant foxtail | 0 | 0 | 0 | 0 | 5 | 5 | 8 | 2 | 0 | 5 | 0 | 0 | 0 | 0 | 0 | 0 | 0 | 0 | 0 | 2 | 0 | 0 | 0 | 0 | 7 | 0 | 0 | 0 | 7 | 9 | 2 | 0 | 9 | 7 | 6 | 9 | 9 | 3 |
| Lambsquarters | 0 | 0 | 0 | 0 | 0 | 9 | 9 | 2 | 0 | 8 | 0 | 0 | 0 | 0 | 0 | 0 | 0 | 0 | 0 | 9 | 0 | 8 | 0 | 2 | 8 | 0 | 0 | 0 | 9 | 9 | 3 | 0 | 9 | 10 | 8 | 9 | 10 | 7 |
| Morningglory | 0 | 0 | 0 | 0 | 0 | 1 | 0 | 4 | 0 | 1 | 0 | 0 | 0 | 0 | 0 | 0 | 0 | 0 | 0 | 2 | 0 | 0 | 0 | 1 | 3 | 0 | 0 | 2 | 8 | 9 | 0 | 0 | 9 | 6 | 4 | 9 | 6 | 0 |
| Nutsedge | 0 | 0 | 0 | 0 | 0 | 0 | 1 | 0 | 0 | 0 | 0 | 0 | 0 | 0 | 3 | 0 | 0 | 0 | 0 | 7 | 0 | 0 | 0 | 0 | 0 | 0 | 0 | 0 | 6 | 8 | 5 | 0 | 9 | 0 | 0 | 7 | 7 | 5 |
| Rape | 0 | 0 | 0 | 0 | 5 | 5 | 9 | 0 | 0 | 7 | 0 | 0 | 0 | 0 | 0 | 0 | 0 | 0 | 2 | 2 | 0 | 0 | 0 | 0 | 6 | 0 | 0 | 0 | 4 | 9 | 0 | 0 | 8 | 9 | 6 | 9 | 9 | 2 |

TABLE B-continued

| | 23 | 24 | 25 | 26 | 27 | 28 | 29 | 30 | 31 | 32 | 33 |
|---|---|---|---|---|---|---|---|---|---|---|---|
| Rice | 0 | 0 | 0 | 0 | 0 | 3 | 9 | 2 | 2 | 5 | 2 |
| Sorghum | 0 | 0 | 0 | 0 | 0 | 3 | 9 | 1 | 1 | 7 | 1 |
| Soybean | 0 | 1 | 0 | 0 | 0 | 4 | 4 | 3 | 0 | 2 | 0 |
| Sugar beet | 1 | 0 | 0 | 0 | 0 | 6 | 7 | 6 | 2 | 3 | 0 |
| Velvetleaf | 0 | 0 | 0 | 0 | 0 | 1 | 1 | 3 | 0 | 0 | 0 |
| Wheat | 0 | 0 | 0 | 0 | 0 | 2 | 9 | 0 | 0 | 0 | 0 |
| Wild buckwheat | 0 | 0 | 0 | 0 | 2 | 5 | 5 | 0 | 0 | 0 | 0 |
| Wild oat | 0 | 0 | 0 | 0 | 0 | 3 | 8 | 0 | 0 | 0 | 0 |

COMPOUND

| Rate (10 g/ha) | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|---|---|---|---|---|---|---|---|

POSTEMERGENCE

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| Barley | 0 | 0 | 0 | 0 | 3 | 8 | 9 | 8 | 8 | 5 | 6 | 0 | 0 | 0 | 0 | 0 | 0 | 0 | 0 | 7 | 0 | 0 | 0 | 6 | 9 | 0 | 4 | 0 | 7 | 9 | 0 | 3 | 3 | 8 | 3 | 3 | 5 | 0 |
| Barnyardgrass | 0 | 0 | 0 | 0 | 0 | 6 | 8 | 5 | 1 | 6 | 3 | 0 | 0 | 0 | 0 | 0 | 0 | 0 | 2 | 8 | 0 | 0 | 0 | 8 | 9 | 0 | 0 | 2 | 9 | 9 | 0 | 0 | 8 | 8 | 2 | 8 | 9 | 7 |
| Bedstraw | 0 | 0 | 0 | 0 | 0 | 6 | 7 | 6 | 3 | 6 | 0 | 0 | 0 | 0 | 0 | 0 | 0 | 0 | 0 | 5 | 0 | 0 | 0 | 5 | 8 | 4 | 7 | 0 | 7 | 10 | 0 | 2 | 4 | 8 | 3 | 5 | 5 | 3 |
| Blackgrass | 0 | 0 | 0 | 0 | 2 | 7 | 8 | 9 | 8 | 2 | 4 | 0 | 0 | 0 | 0 | 0 | 0 | 0 | 3 | 7 | 0 | 0 | 0 | 5 | 6 | 4 | 7 | 7 | 9 | 9 | 0 | 4 | 9 | 9 | 5 | 5 | 7 | 8 |
| Cheatgrass | 0 | 0 | 0 | 0 | 0 | 7 | 8 | 8 | 5 | 0 | 5 | 0 | 0 | 0 | 0 | 0 | 0 | 0 | 0 | 6 | 0 | 0 | 0 | 7 | 10 | 0 | 4 | 3 | 9 | 10 | 5 | 0 | 9 | 9 | 5 | 2 | 8 | 2 |
| Chickweed | 0 | 0 | 0 | 0 | 0 | — | — | 0 | 0 | 5 | 5 | 0 | 0 | 0 | 0 | 0 | 0 | 0 | 0 | 5 | 0 | 0 | 0 | 5 | 9 | 0 | 0 | 0 | 9 | 9 | 2 | 0 | 9 | 9 | 0 | 0 | 8 | 6 |
| Cocklebur | 0 | — | 0 | 0 | — | — | — | — | — | — | — | — | — | — | — | — | — | — | — | — | — | — | — | — | — | — | — | — | — | — | — | — | — | — | — | — | — | — |
| Corn | 0 | 0 | 0 | 0 | 0 | 9 | 9 | 8 | 6 | 8 | 2 | 0 | 0 | 0 | 0 | 0 | 0 | 0 | 0 | 9 | 0 | 0 | 0 | 9 | 9 | 0 | 1 | 4 | 9 | 9 | 0 | 0 | 9 | 9 | 4 | 9 | 9 | 9 |
| Cotton | 0 | 0 | 0 | 0 | 0 | 8 | 9 | 1 | 2 | 1 | 0 | 0 | 0 | 0 | 0 | 0 | 0 | 0 | 8 | 5 | 0 | 0 | 0 | 9 | 5 | 0 | 0 | 1 | 9 | 9 | 0 | 6 | 4 | 2 | 0 | 1 | 6 | 0 |
| Crabgrass | 0 | 0 | 0 | 0 | 2 | 4 | 5 | 0 | 2 | 0 | 3 | 0 | 0 | 0 | 0 | 0 | 0 | 0 | 0 | 5 | 0 | 0 | 0 | 5 | 5 | 0 | 0 | 0 | 9 | 9 | 3 | 3 | 9 | 9 | 2 | 2 | 6 | 2 |
| Giant foxtail | 0 | 0 | 0 | 0 | 2 | 8 | 9 | 8 | 2 | 7 | 0 | 0 | 0 | 0 | 0 | 0 | 0 | 0 | 3 | 7 | 0 | 0 | 0 | 8 | 9 | 2 | 1 | 0 | 8 | 8 | 0 | 4 | 8 | 9 | 4 | 8 | 7 | 5 |
| Lambsquarters | 0 | 0 | 0 | 0 | 4 | 8 | 8 | 0 | 0 | 8 | 0 | — | 0 | 0 | 0 | 0 | 0 | 0 | 0 | 7 | 0 | 0 | 0 | 6 | 10 | 4 | 0 | 4 | 9 | 10 | 2 | 0 | 6 | 8 | 0 | 6 | 7 | 0 |
| Morningglory | 0 | 0 | 0 | 0 | 1 | 0 | 9 | 3 | 3 | 7 | 1 | 0 | 0 | 0 | 0 | 0 | 0 | 0 | 0 | 9 | 0 | 0 | 0 | 8 | 10 | 0 | 0 | 0 | 9 | 10 | 1 | 0 | 9 | 5 | 1 | 9 | 9 | 1 |
| Nutsedge | 0 | 0 | 0 | 0 | 0 | — | 5 | 0 | 0 | 0 | 0 | 0 | 0 | 0 | 0 | 0 | 0 | 0 | 0 | 8 | 0 | 0 | 0 | 2 | 9 | 0 | 0 | 0 | 4 | 7 | 0 | 0 | 4 | 4 | 0 | 0 | 5 | 0 |
| Rape | 0 | 0 | 0 | 0 | 6 | 9 | 9 | 7 | 6 | 9 | 0 | 0 | 0 | 0 | 0 | 0 | 0 | 0 | 8 | 9 | 0 | 0 | 0 | 9 | 9 | 0 | 7 | 7 | 9 | 10 | 3 | 6 | 9 | 9 | 7 | 0 | 9 | 8 |
| Rice | 0 | 0 | 0 | 0 | 0 | 5 | 9 | 8 | 8 | 7 | 7 | 0 | 0 | 0 | 0 | 0 | 0 | 0 | 8 | 9 | 0 | 0 | 0 | 9 | 9 | 0 | 0 | 3 | 9 | 9 | 5 | 6 | 9 | 9 | 9 | 10 | 9 | 9 |
| Sorghum | 0 | 0 | 0 | 0 | 0 | 9 | 9 | 9 | 4 | 9 | 2 | 0 | 0 | 0 | 0 | 0 | 0 | 0 | 2 | 9 | 0 | 0 | 0 | 9 | 9 | 0 | 0 | 0 | 9 | 9 | 0 | 0 | 9 | 9 | 1 | 9 | 9 | 0 |
| Soybean | 0 | 0 | 0 | 0 | 0 | 5 | 2 | 3 | 2 | 2 | 1 | 0 | 0 | 0 | 0 | 0 | 0 | 0 | 3 | 7 | 0 | 0 | 0 | 6 | 5 | 1 | 0 | 2 | 9 | 9 | 3 | 3 | 8 | 9 | 2 | 8 | 8 | 7 |
| Sugar beet | 0 | 0 | 0 | 0 | 2 | 5 | 6 | 2 | 2 | 6 | 0 | 0 | 0 | 0 | 0 | 0 | 0 | 0 | 2 | 8 | 2 | 0 | 0 | 8 | 5 | 0 | 0 | 0 | 9 | 9 | 0 | 0 | 9 | 9 | 7 | 10 | 8 | 7 |
| Velvetleaf | 0 | 0 | 0 | 0 | 0 | 6 | 7 | 0 | 1 | 3 | 3 | 0 | 0 | 0 | 0 | 0 | 0 | 0 | 3 | 6 | 0 | 0 | 0 | 7 | 5 | 0 | 0 | 0 | 8 | 9 | 0 | 4 | 8 | 9 | 6 | 2 | 8 | 3 |
| Wheat | 0 | 0 | 0 | 0 | 0 | 6 | 7 | 8 | 8 | 0 | 7 | 0 | 0 | 0 | 0 | 0 | 0 | 0 | 3 | 8 | 2 | 0 | 0 | 7 | 6 | 0 | 0 | 0 | 8 | 8 | 0 | 4 | 9 | 9 | 5 | 8 | 7 | 8 |
| Wild buckwheat | 0 | 0 | 0 | 0 | 0 | 8 | 8 | 2 | 2 | 7 | 0 | 0 | 0 | 0 | 0 | 0 | 0 | 0 | 0 | 8 | 0 | 0 | 0 | 7 | 6 | 0 | 0 | 0 | 9 | 8 | 0 | 3 | 9 | 9 | 5 | 2 | 8 | 5 |
| Wild oat | 0 | 0 | 0 | 0 | 0 | 8 | 8 | 9 | 8 | 0 | 7 | 0 | 0 | 0 | 0 | 0 | 0 | 0 | 0 | 8 | 0 | 0 | 0 | 5 | 6 | 0 | 2 | 0 | 8 | 8 | 0 | 4 | 9 | 9 | 5 | 8 | 7 | 5 |

PREEMERGENCE

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| Barley | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 9 | 0 | 0 | 2 | 0 | 0 | 2 | 2 | 0 |
| Barnyardgrass | 0 | 0 | 0 | 0 | 0 | 0 | 0 | 0 | 0 | 0 | 0 | 0 | 0 | 0 | 0 | 0 | 0 | 0 | 1 | 1 | 0 | 0 | 0 | 0 | 2 | 0 | 0 | 0 | 0 | 2 | 0 | 0 | 2 | 5 | 1 | 8 | 3 | 1 |
| Bedstraw | 0 | 0 | 0 | 0 | 0 | 0 | 4 | 0 | 2 | 0 | 0 | 0 | 0 | 0 | 0 | 0 | 0 | 0 | 0 | 3 | 0 | 2 | 6 | 0 | 0 | 0 | 0 | 0 | 0 | 8 | 0 | 0 | 9 | 2 | 0 | 4 | 0 | 0 |
| Blackgrass | 0 | 0 | 0 | 0 | 0 | 0 | 8 | 0 | 2 | 0 | 0 | 0 | 0 | 0 | 0 | 0 | 0 | 0 | 0 | 3 | 0 | 2 | 0 | 0 | 2 | 0 | 2 | 0 | 0 | 9 | 0 | 0 | 9 | 2 | 0 | 6 | 3 | 2 |
| Cheatgrass | 0 | 0 | 0 | 0 | 0 | 0 | 8 | 0 | 2 | 0 | 0 | 0 | 0 | 0 | 0 | 0 | 0 | 0 | 0 | 3 | 0 | 0 | 0 | 0 | 4 | 0 | 2 | 0 | 7 | 9 | 0 | 0 | 10 | 3 | 4 | 6 | 8 | 5 |
| Chickweed | 0 | 0 | 0 | 0 | 0 | 0 | 0 | 0 | 2 | 0 | 0 | 0 | 0 | 0 | 0 | 0 | 0 | 0 | 0 | 7 | 0 | 0 | 0 | 0 | 2 | 0 | 0 | 0 | 0 | 5 | 0 | 0 | 5 | 1 | 2 | 10 | 8 | 5 |
| Cocklebur | 0 | — | 0 | 0 | — | 0 | 0 | 0 | 0 | 0 | 0 | 0 | 0 | 0 | 0 | 0 | 0 | 0 | 0 | — | 0 | — | — | 0 | — | 0 | 0 | 0 | — | — | 0 | 0 | — | — | — | — | — | — |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 5 | 0 | 0 | 5 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 5 | 0 | 0 | 2 | 0 | 0 | 0 | 0 | 0 |

TABLE B-continued

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| Crabgrass | 0 | 0 | 0 | 0 | 0 | 0 | 0 | 0 | 0 | — | — | — | — | — | — | — | — | — | — | — | 0 | 0 | 0 | 7 | 0 | 0 | 4 | 0 | 5 | 6 | 2 | 0 |
| Giant foxtail | 0 | 0 | 0 | 0 | 0 | 3 | 0 | 0 | 0 | 0 | 0 | 0 | 0 | 0 | 0 | 0 | 0 | 0 | 0 | 2 | 0 | 0 | 0 | 3 | 0 | 0 | 3 | 2 | 0 | 6 | 1 | 0 |
| Lambsquarters | 0 | 0 | 0 | 2 | 0 | 7 | 0 | 0 | 0 | 0 | 0 | 0 | 0 | 3 | 0 | 0 | 0 | 0 | 0 | 0 | 0 | 0 | 0 | 8 | 0 | 0 | 8 | 9 | 0 | 5 | 9 | 2 |
| Morning-glory | 0 | 0 | 0 | 0 | 0 | 0 | 0 | 0 | 0 | 0 | 0 | 3 | 0 | 0 | 0 | 0 | 0 | 0 | — | 0 | 0 | 0 | 0 | 3 | 0 | 0 | 7 | 1 | 0 | 5 | 5 | 0 |
| Nutsedge | 0 | 0 | 0 | 0 | 0 | 0 | 0 | 0 | — | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 2 | 0 | 0 | 0 | 0 | 7 | 0 | 0 | 0 | 6 | 0 | 0 | 5 | 4 | 2 | 2 | 0 | 0 |
| Rice | 0 | 0 | 0 | 0 | 0 | 5 | 0 | 0 | 2 | 7 | 0 | 0 | 2 | 0 | 0 | 2 | 0 | 0 | 0 | 2 | 0 | 0 | 6 | 9 | 2 | 0 | 9 | 6 | 2 | 9 | 8 | 7 |
| Sorghum | 0 | 0 | 0 | 0 | 0 | 3 | 0 | 0 | 2 | 2 | 0 | 0 | 0 | 3 | 0 | 0 | 0 | 0 | 0 | 2 | 0 | 0 | 0 | 7 | 0 | 2 | 7 | 2 | 0 | 7 | 1 | 0 |
| Soybean | 0 | 0 | 0 | 0 | 0 | 1 | 0 | 0 | 0 | 2 | 0 | 0 | 0 | — | 0 | 0 | 0 | 0 | 0 | 0 | 0 | 0 | 2 | 8 | 2 | 0 | 6 | 5 | 5 | 4 | 3 | 2 |
| Sugar beet | 0 | 0 | 0 | 0 | 0 | 2 | 0 | 4 | 0 | 3 | 0 | 0 | 0 | 2 | 0 | 0 | 0 | 0 | 0 | 3 | 0 | 0 | 7 | 9 | 0 | 0 | 6 | 7 | 0 | 7 | 3 | 3 |
| Velvetleaf | 0 | 0 | 0 | 0 | 0 | 0 | 0 | 0 | 0 | 0 | 0 | 0 | 0 | 0 | 0 | 0 | 0 | 0 | 0 | 3 | 0 | 0 | — | 2 | 0 | 0 | 2 | 1 | 5 | 3 | 2 | 3 |
| Wheat | 0 | 0 | 0 | 0 | 0 | 3 | 0 | 0 | 0 | 3 | 0 | 0 | 0 | 0 | 0 | 0 | 0 | 0 | 0 | 2 | 0 | 0 | 6 | 9 | 0 | 0 | 9 | 0 | 0 | 3 | 6 | 0 |
| Wild buckwheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 2 | 0 | 0 | 0 | 0 | 0 |
| Wild oat | 0 | 0 | 0 | 0 | 0 | 2 | 0 | 0 | 0 | 0 | 0 | 2 | 0 | 0 | 0 | 0 | 0 | 0 | 0 | 3 | 0 | 0 | 5 | 8 | 0 | 0 | 3 | 0 | 0 | 0 | 2 | 0 |

Test C

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria* spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybeam (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. Plant response ratings, summarized in Table C, are reported on a 0 to 10 scale where 0 is no effect and 10 is complete control. A dash (—) esponse means no test result.

TABLE C

| | COMPOUND | | | | | | | | | | | | | | | | | | | | | | |
|---|---|---|---|---|---|---|---|---|---|---|---|---|---|---|---|---|---|---|---|---|---|---|---|
| | Rate (250 g/ha) | | | | Rate (62 g/ha) | | | | | | Rate (16 g/ha) | | | | | | Rate (4 g/ha) | | | | | Rate (1 g/ha) | |
| | 2 | 8 | 10 | 11 | 1 | 2 | 8 | 9 | 10 | 11 | 1 | 2 | 8 | 9 | 10 | 11 | 1 | 2 | 8 | 9 | 10 | 11 | 1 | 9 |
| POSTEMERGENCE | | | | | | | | | | | | | | | | | | | | | | | | |
| Barley | 10 | 9 | 10 | 10 | 10 | 10 | 8 | 5 | 10 | 10 | 10 | 8 | 8 | 4 | 9 | 10 | 10 | 7 | 7 | 0 | 9 | 8 | 9 | 0 |
| Blackgrass | 10 | 10 | 10 | 10 | 9 | 9 | 10 | 7 | 10 | 9 | 9 | 8 | 10 | 5 | 9 | 9 | 9 | 6 | 9 | 3 | 7 | 7 | 7 | 0 |
| Chickweed | 7 | 10 | 10 | 10 | 10 | 6 | 10 | 7 | 10 | 10 | 10 | 3 | 9 | 3 | 10 | 9 | 10 | 0 | 8 | 0 | 9 | 8 | 10 | 0 |
| Cocklebur | 10 | 10 | 10 | 10 | 10 | 8 | 10 | — | 10 | 10 | 10 | 2 | 9 | — | 10 | 10 | 10 | 0 | 7 | — | 10 | 10 | 9 | — |
| Corn | 10 | 9 | 10 | 10 | 10 | 10 | 9 | 10 | 10 | 10 | 10 | 8 | 8 | 0 | 10 | 10 | 9 | 8 | 8 | 0 | 9 | 9 | 9 | 0 |
| Cotton | 3 | 10 | 10 | 10 | 10 | 2 | 9 | 10 | 10 | 10 | 9 | 0 | 9 | 3 | 9 | 9 | 8 | 0 | 7 | 0 | 5 | 4 | 5 | 0 |
| Crabgrass | 9 | 10 | 10 | 10 | 10 | 8 | 7 | 10 | 10 | 10 | 9 | 3 | 7 | 3 | 9 | 9 | 6 | 3 | 5 | 0 | 8 | 7 | 4 | 0 |
| Downy brome | 10 | 9 | 10 | 10 | 10 | 10 | 9 | 7 | 10 | 9 | 10 | 10 | 8 | 0 | 9 | 9 | 10 | 9 | 8 | 0 | 5 | 7 | 9 | 0 |
| Giant foxtail | 10 | 8 | 8 | 9 | 10 | 10 | 7 | 10 | 5 | 6 | 10 | 9 | 4 | 3 | 3 | 3 | 10 | 5 | 2 | 0 | 0 | 0 | 6 | 0 |
| Green foxtail | 10 | 9 | 10 | 10 | 10 | 10 | 8 | 10 | 5 | 8 | 10 | 10 | 6 | 0 | 3 | 3 | 10 | 7 | 2 | 0 | 0 | 0 | 10 | 0 |
| Jimsonweed | 10 | 10 | 10 | 10 | 10 | 9 | 10 | 10 | 10 | 10 | 10 | 9 | 10 | 3 | 10 | 10 | 10 | 8 | 9 | 0 | 10 | 10 | 9 | 0 |
| Johnsongrass | 10 | 9 | 10 | 10 | 10 | 10 | 9 | 9 | 10 | 10 | 10 | 9 | 8 | 0 | 9 | 10 | 10 | 5 | 8 | 0 | 9 | 7 | 8 | 0 |
| Lambsquarters | 10 | 10 | 10 | 10 | 10 | 7 | 8 | 10 | 10 | 10 | 10 | 5 | 8 | 7 | 10 | 9 | 10 | 2 | 7 | 3 | 8 | 5 | 8 | 0 |
| Morningglory | 7 | 10 | 10 | 10 | 10 | 4 | 9 | 9 | 10 | 10 | 10 | 0 | 9 | 6 | 10 | 9 | 10 | 0 | 9 | 4 | 9 | 9 | 10 | 3 |
| Nutsedge | 6 | 10 | 10 | 10 | 10 | 4 | 8 | 10 | 9 | 7 | 8 | 0 | 8 | 3 | 9 | 5 | 8 | 0 | 7 | 3 | 3 | 2 | 7 | 0 |
| Rape | 10 | 10 | 10 | 10 | 10 | 10 | 10 | 9 | 9 | 10 | 10 | 5 | 9 | 9 | 9 | 10 | 10 | 0 | 8 | 3 | 9 | 10 | 10 | 3 |
| Rice Dry Seed | 10 | 9 | 10 | 10 | 10 | 10 | 9 | 6 | 10 | 10 | 10 | 10 | 8 | 0 | 10 | 10 | 10 | 8 | 8 | 0 | 9 | 9 | 9 | 0 |
| Sicklepod | 8 | 10 | 10 | 10 | 10 | 8 | 8 | 8 | 8 | 10 | 10 | 0 | 8 | 0 | 8 | 10 | 9 | 0 | 4 | 0 | 3 | 4 | 4 | 0 |
| Soybean | 9 | 9 | 10 | 10 | 10 | 7 | 8 | 8 | 9 | 8 | 10 | 1 | 8 | 0 | 8 | 7 | 10 | 0 | 3 | 0 | 6 | 7 | 9 | 0 |
| Sugar beet | 10 | 10 | 10 | 10 | 10 | 10 | 10 | 10 | 10 | 9 | 10 | 9 | 10 | 10 | 10 | 8 | 10 | 4 | 9 | 7 | 10 | 3 | 10 | 4 |
| Teaweed | 6 | 8 | 9 | 10 | 10 | 5 | 8 | 8 | 8 | 9 | 10 | 3 | 3 | 0 | 8 | 7 | 10 | 3 | 3 | 0 | 4 | 3 | 10 | 0 |
| Velvetleaf | 4 | 10 | 10 | 10 | 10 | 0 | 10 | 10 | 10 | 10 | 10 | 0 | 10 | 3 | 10 | 10 | 9 | 0 | 10 | 0 | 6 | 3 | 9 | 0 |
| Wheat | 10 | 9 | 9 | 10 | 9 | 9 | 8 | 6 | 9 | 9 | 9 | 8 | 8 | 4 | 9 | 8 | 6 | 6 | 8 | 0 | 8 | 7 | 5 | 0 |
| Wild buckwheat | 10 | 10 | 10 | — | 10 | 5 | 10 | 8 | 10 | 9 | 10 | 0 | 9 | 4 | 5 | 7 | 10 | 0 | 8 | 0 | — | 3 | 10 | 0 |
| Wild oat | 10 | 8 | 10 | 10 | 10 | 10 | 8 | 7 | 9 | 10 | 10 | 10 | 7 | 2 | 9 | 9 | 10 | 8 | 5 | 0 | 8 | 8 | 9 | 0 |
| Barnyardgrass | 10 | 9 | 10 | 10 | 10 | 10 | 9 | 10 | 10 | 10 | 10 | 8 | 9 | 3 | 9 | 10 | 5 | 4 | 9 | 0 | 9 | 9 | 4 | 0 |
| PREEMERGENCE | | | | | | | | | | | | | | | | | | | | | | | | |
| Barley | 10 | 7 | 9 | 9 | 10 | 9 | 4 | 0 | 7 | 3 | 10 | 4 | 2 | 0 | 3 | 0 | 5 | 0 | 0 | 0 | 0 | 0 | 2 | 0 |
| Blackgrass | 8 | 9 | 9 | 9 | 9 | 6 | 9 | 5 | 8 | 7 | 8 | 5 | 8 | 0 | 8 | 4 | 6 | 3 | 4 | 0 | 5 | 0 | 0 | 0 |
| Chickweed | 5 | 8 | 9 | 9 | 10 | 0 | 7 | 8 | 8 | 8 | 10 | 0 | 5 | 7 | 7 | 7 | 9 | 0 | 3 | 7 | 7 | 3 | 7 | 6 |
| Cocklebur | 8 | 5 | 9 | — | 10 | — | — | 5 | 8 | 3 | 8 | 3 | 2 | — | 3 | 0 | 7 | 0 | 0 | 0 | — | 0 | 0 | 0 |
| Corn | 10 | 9 | 10 | 10 | 10 | 7 | 6 | 3 | 9 | 4 | 8 | 4 | 4 | 0 | 8 | 4 | 3 | 0 | 0 | 0 | 2 | 2 | 2 | 0 |
| Cotton | 8 | 9 | 9 | 10 | 9 | 5 | 4 | 3 | 8 | 8 | 8 | 0 | 2 | 0 | 6 | 3 | 5 | 0 | 0 | 0 | 2 | 0 | 0 | 0 |
| Crabgrass | 9 | 10 | 10 | 10 | 10 | 3 | 9 | 10 | 10 | 10 | 10 | 2 | 9 | 10 | 9 | 8 | 6 | 0 | 3 | 4 | 4 | 3 | 4 | 3 |
| Downy brome | 10 | 10 | 10 | 9 | 10 | 10 | 7 | 2 | 10 | 9 | 10 | 6 | 5 | 0 | 7 | 3 | 8 | 0 | 3 | 0 | 3 | 0 | 3 | 0 |
| Giant foxtail | 10 | 8 | 5 | 8 | 10 | 6 | 5 | 2 | 3 | 5 | 9 | 2 | 3 | 0 | 2 | 3 | 8 | 0 | 0 | 0 | 0 | 0 | 3 | 0 |
| Green foxtail | 10 | 10 | 8 | 9 | 10 | 9 | 9 | 5 | 5 | 5 | 9 | 3 | 5 | 2 | 3 | 3 | 7 | 0 | 3 | 0 | 0 | 0 | 3 | 0 |
| Jimsonweed | 9 | 9 | 9 | 9 | 10 | 9 | 3 | 0 | 9 | 9 | 10 | 8 | 0 | 0 | 5 | 3 | 9 | 6 | 0 | 0 | 0 | 0 | 4 | 0 |
| Johnsongrass | 10 | 9 | 9 | 9 | 10 | 10 | 7 | 3 | 8 | 3 | 10 | 5 | 3 | 2 | 7 | 0 | 9 | 0 | 0 | 0 | 3 | 0 | 5 | 0 |
| Lambsquarters | 10 | 9 | 10 | 9 | 10 | 8 | 9 | 9 | 10 | 8 | 10 | — | 8 | 8 | 9 | 5 | 10 | — | 5 | 0 | 9 | 0 | 0 | 0 |
| Morningglory | 8 | 9 | 9 | 9 | 10 | 8 | 8 | 0 | 9 | 8 | 9 | 3 | 4 | 0 | 8 | 3 | 8 | 3 | 0 | 0 | 3 | 0 | 6 | 0 |
| Nutsedge | 8 | 8 | 9 | 5 | 10 | 6 | 8 | 0 | 3 | 5 | 10 | 5 | 3 | 0 | 0 | 2 | 9 | 0 | 0 | 0 | 0 | 0 | 4 | — |
| Rape | 7 | 9 | 10 | 8 | 10 | 0 | 5 | 8 | 10 | 7 | 4 | 0 | 3 | 0 | 5 | 3 | 2 | 0 | 0 | 0 | 0 | 0 | 0 | 0 |
| Rice Dry Seed | 10 | 9 | 10 | 10 | 9 | 8 | 5 | 4 | 10 | 10 | 9 | 5 | 4 | 4 | 6 | 8 | 6 | 1 | 2 | 3 | 4 | 3 | 3 | 0 |
| Sicklepod | 8 | 8 | 9 | 5 | 10 | 9 | 8 | 7 | 3 | 5 | — | 9 | 3 | 3 | 0 | 5 | 2 | 7 | — | 0 | — | 5 | 0 | 5 | — |
| Soybean | 6 | 8 | 8 | 8 | 10 | 0 | 3 | 4 | 4 | 4 | 5 | 0 | 0 | 3 | 2 | 2 | 3 | 0 | 0 | 0 | 0 | 0 | 0 | — |
| Sugar beet | 10 | 9 | 10 | 5 | 10 | 9 | 9 | 3 | 9 | 5 | 10 | 6 | 3 | 0 | 7 | 5 | 10 | 0 | 0 | 0 | 5 | 5 | 9 | 0 |
| Teaweed | 9 | 9 | 9 | 9 | 9 | 9 | 9 | 7 | 9 | 7 | 9 | 9 | 5 | 0 | 9 | 3 | 9 | 9 | 0 | — | 7 | 0 | 8 | — |
| Velvetleaf | 2 | 9 | 9 | 9 | 9 | 1 | 8 | 8 | 8 | 9 | 9 | 0 | 5 | 6 | 8 | 8 | 4 | 0 | 5 | 4 | 5 | 3 | 0 | 4 |
| Wheat | 10 | 7 | 9 | 9 | 9 | 10 | 4 | 0 | 7 | 5 | 4 | 4 | 2 | 0 | 3 | 3 | 2 | — | 0 | 0 | 0 | 0 | 0 | 0 |
| Wild buckwheat | 5 | 10 | 9 | 9 | 10 | 3 | 9 | — | 9 | 9 | 9 | 0 | 5 | — | 8 | 7 | 8 | 0 | 3 | — | 7 | 2 | 5 | — |
| Wild oat | 9 | 7 | 8 | 5 | 10 | 4 | 5 | 0 | 10 | 8 | 9 | 3 | 4 | 0 | 3 | 3 | 5 | 0 | 0 | 0 | 0 | 2 | 3 | 0 |
| Barnyardgrass | 9 | 10 | 10 | 10 | 10 | 6 | 5 | 5 | 10 | 8 | 7 | 0 | 4 | 2 | 5 | 5 | 2 | 0 | 0 | 0 | 0 | 0 | 0 | 0 |

TEST D

The compounds evaluated in this test were formulated in a non-phytotoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (*Amaranthusretroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), and umbrella sedge (*Cyperus difformis*).

All plant species were grown using normal greenhouse practices. Visual evaluations of injury expressed on treated plants, when compared to untreated controls, were recorded approximately fourteen to twenty-one days after application of the test compound. Plant response ratings, summarized in Table D, were recorded on a 0 to 10 scale where 0 is no injury and 10 is complete control. A dash (—) response means no test result.

TABLE D

| | Rate (250 g/ha) COMPOUND 5 | Rate (125 g/ha) COMPOUND 42 | POSTEMERGENCE Rate (62 g/ha) COMPOUND | | | | | | | | | | | | | | | | |
|---|---|---|---|---|---|---|---|---|---|---|---|---|---|---|---|---|---|---|---|
| | | | 3 | 4 | 5 | 6 | 14 | 18 | 21 | 22 | 29 | 30 | 42 | 47 | 51 | 52 | 55 | 56 | 58 | 59 |
| Barley Igri | 8 | 10 | 9 | 10 | 7 | 10 | 10 | 10 | 6 | 7 | 6 | 6 | 10 | 9 | 10 | 10 | 6 | 6 | 0 | 6 |
| Bedstraw | 10 | 10 | 9 | 10 | 8 | 10 | 10 | 10 | 7 | 10 | 10 | 7 | 10 | 10 | 10 | 10 | 10 | 10 | 10 | 10 |
| Blackgrass | 7 | 10 | 7 | 8 | 6 | 10 | 10 | 10 | 9 | 8 | 7 | 8 | 10 | 9 | 10 | 10 | 10 | 10 | 7 | 10 |
| Chickweed | 9 | 10 | 10 | 10 | 6 | 10 | 10 | 10 | 3 | 10 | — | — | 10 | 10 | 10 | 10 | — | — | — | — |
| Corn | 10 | 10 | 10 | 10 | 7 | 10 | 10 | 10 | 9 | 10 | 9 | 10 | 10 | 10 | 10 | 10 | 10 | 10 | 10 | 10 |
| Cotton | 0 | 9 | 7 | 8 | 0 | 7 | 9 | 7 | 3 | 7 | 8 | 0 | 8 | 9 | 9 | 10 | 10 | 10 | 9 | 10 |
| Crabgrass | 9 | 8 | 9 | 10 | 6 | 9 | 9 | 9 | 5 | 9 | 9 | 7 | 7 | 10 | 10 | 10 | 10 | 9 | 7 | 8 |
| Downy brome | 10 | 10 | 8 | 9 | 9 | 10 | 10 | 10 | 9 | 8 | 7 | 8 | 10 | 9 | 10 | 10 | 7 | 7 | 4 | 10 |
| Giant foxtail | 10 | 8 | 10 | 10 | 8 | 10 | 10 | 10 | 7 | 10 | 10 | 10 | 7 | 10 | 7 | 10 | 10 | 10 | 10 | 10 |
| Lambsquarters | 10 | 10 | 10 | 10 | 8 | 10 | 10 | 10 | 4 | 10 | 10 | 6 | 10 | 10 | 10 | 10 | 9 | 10 | 8 | 10 |
| Morningglory | 2 | 8 | 9 | 10 | 0 | 8 | 9 | 10 | 5 | 10 | 9 | 5 | 8 | 10 | 10 | 10 | 10 | 10 | 10 | 10 |
| Pigweed | 10 | 10 | 10 | 10 | 9 | 9 | 9 | 10 | 9 | 10 | 9 | 9 | 10 | 10 | 10 | 10 | 9 | 10 | 10 | 10 |
| Rape | 6 | 10 | 10 | 10 | 2 | 10 | 10 | 10 | 10 | 10 | 8 | 7 | 10 | 10 | 10 | 10 | 10 | 10 | 10 | 10 |
| Ryegrass | 10 | 8 | 8 | 10 | 10 | 10 | 10 | 10 | 10 | 10 | 6 | 10 | 8 | 9 | 10 | 10 | 7 | 8 | 6 | 8 |
| Sorghum | 9 | 10 | 10 | 10 | 8 | 10 | 10 | 10 | 7 | 10 | 9 | 9 | 10 | 10 | 10 | 10 | 10 | 10 | 10 | 10 |
| Soybean | 4 | 10 | 9 | 10 | 3 | 10 | 9 | 10 | 8 | 10 | 8 | 8 | 10 | 10 | 10 | 10 | 9 | 10 | 9 | 10 |
| Speedwell | 0 | 6 | 8 | 8 | 0 | 10 | 6 | 6 | 0 | 9 | 5 | 8 | 6 | 8 | 6 | 6 | 10 | 9 | 9 | 10 |
| Sugar beet | 9 | 10 | 8 | 10 | 6 | 10 | 10 | 10 | 7 | 10 | 7 | 7 | 10 | 10 | 10 | 10 | 10 | 10 | 10 | 10 |
| Velvetleaf | 3 | 9 | 9 | 9 | 0 | 10 | 9 | 10 | 7 | 9 | 3 | 0 | 8 | 10 | 9 | 10 | 9 | 10 | 10 | 9 |
| Wheat | 7 | 10 | 7 | 7 | 6 | 10 | 10 | 10 | 10 | 7 | 6 | 6 | 10 | 9 | 10 | 10 | 6 | 7 | 3 | 6 |
| Wild buckwheat | 6 | 10 | 8 | 10 | 6 | 10 | 10 | 8 | 9 | 10 | 8 | 8 | 10 | 10 | 10 | 10 | 10 | 10 | 9 | 10 |
| Wild oat | 8 | 10 | 7 | 8 | 8 | 9 | 10 | 10 | 9 | 6 | 6 | 7 | 10 | 9 | 10 | 10 | 6 | 6 | 0 | 6 |
| Barnyardgrass | 3 | 8 | 5 | 7 | 0 | 9 | 9 | 6 | 2 | 9 | 9 | 6 | 5 | 9 | 6 | 9 | 2 | 8 | 6 | 5 |
| Rice Japonica | 8 | 8 | 8 | 8 | 3 | 8 | 9 | 7 | 4 | 9 | 8 | 4 | 7 | 8 | 8 | 9 | 7 | 9 | 9 | 5 |
| Umbrella sedge | | 7 | 3 | 9 | — | 0 | 10 | 9 | 7 | 8 | 9 | 2 | 6 | 9 | 8 | 9 | 6 | 6 | 0 | 6 |

| | POSTEMERGENCE Rate (31 g/ha) COMPOUND | | | | | | | | | | | | | | | Rate (16 g/ha) COMPOUND | | | | | | | | |
|---|---|---|---|---|---|---|---|---|---|---|---|---|---|---|---|---|---|---|---|---|---|---|---|---|
| | 14 | 18 | 19 | 21 | 22 | 29 | 30 | 42 | 47 | 51 | 52 | 55 | 56 | 58 | 59 | 3 | 4 | 5 | 6 | 14 | 18 | 19 | 21 | 22 | 29 | 30 | 42 |
| Barley Igri | 10 | 10 | 10 | 5 | 7 | 5 | 6 | 10 | 9 | 10 | 10 | 5 | 6 | 0 | 5 | 6 | 8 | 6 | 9 | 10 | 10 | 10 | 3 | 7 | 5 | 5 | 10 |
| Bedstraw | 10 | 10 | 10 | 7 | 10 | 8 | 7 | 10 | 10 | 10 | 10 | 10 | 10 | 10 | 10 | 8 | 9 | 5 | 10 | 7 | 5 | 10 | 4 | 10 | 7 | 7 | 10 |
| Blackgrass | 10 | 10 | 10 | 5 | 8 | 7 | 7 | 8 | 9 | 10 | 10 | 10 | 10 | 7 | 8 | 6 | 7 | 3 | 9 | 10 | 10 | 10 | 3 | 8 | 7 | 6 | 8 |
| Chickweed | 10 | 10 | 10 | 0 | 10 | — | — | 10 | 10 | 10 | 10 | — | — | — | — | 10 | 10 | 3 | 10 | 9 | 8 | 10 | 0 | 10 | — | — | 8 |
| Corn | 10 | 10 | 10 | 7 | 10 | 9 | 10 | 10 | 10 | 10 | 10 | 10 | 10 | 10 | 10 | 9 | 10 | 4 | 10 | 10 | 10 | 10 | 6 | 10 | 9 | 9 | 10 |
| Cotton | 8 | 7 | 9 | 2 | 7 | 7 | 0 | 7 | 8 | 9 | 10 | 9 | 10 | 9 | 10 | 6 | 7 | 0 | 7 | 7 | 6 | 8 | 2 | 6 | 7 | 0 | 7 |
| Crabgrass | 8 | 8 | 9 | 3 | 9 | 9 | 6 | 6 | 10 | 8 | 10 | 9 | 8 | 5 | 4 | 9 | 9 | 3 | 8 | 8 | 7 | 8 | 2 | 8 | 8 | 4 | 5 |
| Downy brome | 10 | 10 | 10 | 9 | 8 | 7 | 7 | 10 | 9 | 10 | 10 | 7 | 6 | 3 | 8 | 7 | 8 | 8 | 9 | 9 | 10 | 10 | 6 | 7 | 7 | 6 | 9 |
| Giant foxtail | 10 | 10 | 10 | 7 | 10 | 10 | 9 | 7 | 10 | 7 | 10 | 10 | 10 | 9 | 10 | 9 | 10 | 7 | 10 | 10 | 8 | 10 | 5 | 10 | 10 | 9 | 7 |
| Lambsquarters | 10 | 10 | 10 | 4 | 10 | 10 | 6 | 10 | 10 | 10 | 10 | 9 | 10 | 6 | 9 | 9 | 10 | 6 | 10 | 10 | 10 | 10 | 3 | 10 | 10 | 4 | 10 |
| Morningglory | 9 | 10 | 10 | 4 | 10 | 8 | 4 | 8 | 10 | 10 | 10 | 10 | 9 | 10 | 10 | 8 | 10 | 0 | 7 | 9 | 10 | 10 | 3 | 10 | 7 | 4 | 7 |
| Pigweed | 9 | 9 | 10 | 7 | 10 | 9 | 8 | 10 | 10 | 10 | 10 | 9 | 10 | 10 | 10 | 10 | 10 | 9 | 8 | 7 | 8 | 10 | 6 | 8 | 8 | 8 | 8 |
| Rape | 10 | — | 10 | 9 | 10 | 8 | 7 | 10 | 10 | 10 | 10 | 10 | 10 | 10 | 10 | 7 | 10 | 0 | 10 | 10 | 10 | 10 | 7 | 10 | 7 | 4 | 10 |
| Ryegrass | 9 | 10 | 10 | 9 | 10 | 6 | 8 | 8 | 6 | 10 | 10 | 7 | 7 | 5 | 7 | 6 | 7 | 6 | 8 | 7 | 10 | 10 | 8 | 8 | 6 | 6 | 5 |
| Sorghum | 9 | 10 | 10 | 6 | 10 | 9 | 9 | 10 | 10 | 10 | 10 | 10 | 10 | 10 | 10 | 9 | 10 | 6 | 10 | 9 | 10 | 10 | 6 | 10 | 9 | 8 | 8 |
| Soybean | 9 | 10 | 10 | 7 | 10 | 8 | 6 | 9 | 10 | 10 | 10 | 9 | 10 | 9 | 10 | 8 | 9 | 0 | 10 | 9 | 10 | 10 | 6 | 8 | 7 | 5 | 9 |
| Speedwell | 6 | 6 | 0 | 0 | 8 | 3 | 7 | 3 | 3 | — | 5 | 9 | 7 | 7 | 10 | 8 | 8 | 0 | 10 | 5 | 6 | 0 | 0 | 8 | 0 | 5 | 3 |
| Sugar beet | 10 | 10 | 10 | 7 | 10 | 7 | 7 | 10 | 10 | 10 | 10 | 10 | 10 | 10 | 10 | 8 | 10 | 3 | 10 | 10 | 10 | 10 | 6 | 10 | 7 | 5 | 10 |
| Velvetleaf | 9 | 9 | 10 | 3 | 8 | 3 | 0 | 7 | 8 | 8 | 10 | 9 | 10 | 10 | 9 | 8 | 9 | 0 | 8 | 9 | 8 | 9 | 3 | 7 | 2 | 0 | 6 |
| Wheat | 10 | 10 | 10 | 8 | 6 | 6 | 6 | 10 | 9 | 9 | 10 | 6 | 5 | 3 | 6 | 6 | 6 | 6 | 4 | 10 | 10 | 10 | 7 | 6 | 6 | 5 | 9 |
| Wild buckwheat | 10 | 8 | 10 | 7 | 10 | 7 | 7 | 10 | 9 | 10 | 10 | 10 | 10 | 9 | 10 | 7 | 9 | 0 | 10 | 9 | 7 | 10 | 6 | 10 | 7 | 6 | 9 |
| Wild oat | 10 | 10 | 10 | 9 | 4 | 5 | 7 | 10 | 9 | 10 | 10 | 4 | 6 | 0 | 5 | 6 | 7 | 6 | 5 | 9 | 10 | 10 | 5 | 4 | 5 | 6 | 9 |
| Barnyardgrass | 2 | 4 | 1 | 2 | 9 | 8 | 1 | 4 | 8 | 4 | 9 | 1 | 8 | 0 | 2 | 0 | 6 | 0 | 6 | 2 | 0 | 1 | 0 | 7 | 8 | 0 | 2 |
| Rice Japonica | 8 | 4 | 7 | 4 | 9 | 8 | 1 | 4 | 8 | 5 | 9 | 6 | 7 | 5 | 1 | 7 | 7 | 0 | 7 | 6 | 0 | 5 | 3 | 6 | 8 | 0 | 0 |

TABLE D-continued

| | | | | | | | | | | | | | | | | | | | | | | | | | |
|---|---|---|---|---|---|---|---|---|---|---|---|---|---|---|---|---|---|---|---|---|---|---|---|---|---|
| Umbrella sedge | 9 | 9 | 9 | 4 | 8 | 9 | 0 | 5 | 9 | 7 | 8 | 4 | 6 | 0 | 4 | 0 | 0 | — | 0 | 8 | 8 | 9 | 2 | 7 | 8 | 0 | 0 |

POSTEMERGENCE

| | Rate (16 g/ha) COMPOUND | | | | | | | | | | Rate (8 g/ha) COMPOUND | | | | | | | | | | | | | | Rate (4 g/ha) COMPOUND | | | | | |
|---|---|---|---|---|---|---|---|---|---|---|---|---|---|---|---|---|---|---|---|---|---|---|---|---|---|---|---|---|---|---|
| | 47 | 51 | 52 | 55 | 56 | 58 | 59 | 14 | 18 | 19 | 21 | 22 | 29 | 30 | 42 | 47 | 51 | 52 | 55 | 56 | 58 | 59 | 3 | 4 | 5 | 6 | 14 |
| Barley Igri | 9 | 10 | 10 | 3 | 5 | 0 | 4 | 9 | 10 | 10 | 0 | 6 | 5 | 4 | 7 | 7 | 9 | 10 | 3 | 5 | 0 | 3 | 5 | 6 | 5 | 6 | 6 |
| Bedstraw | 10 | 10 | 10 | 8 | 10 | 10 | 8 | 6 | 5 | 10 | 4 | 7 | 7 | 6 | 5 | 9 | 10 | 10 | 7 | 8 | 10 | 8 | 7 | 9 | 3 | 10 | 4 |
| Blackgrass | 9 | 10 | 10 | 10 | 9 | 6 | 7 | 10 | 10 | 9 | 3 | 7 | 6 | 6 | 5 | 8 | 9 | 10 | 8 | 7 | 5 | 7 | 3 | 7 | 0 | 8 | 10 |
| Chickweed | 10 | 10 | 10 | — | — | — | — | 8 | 7 | 10 | 0 | 9 | — | — | 8 | 10 | 10 | 10 | — | — | — | — | 6 | 10 | 0 | 10 | 8 |
| Corn | 10 | 10 | 10 | 10 | 10 | 10 | 10 | 9 | 10 | 10 | 6 | 9 | 9 | 9 | 10 | 10 | 10 | 10 | 10 | 10 | 9 | 9 | 9 | 9 | 2 | 10 | 9 |
| Cotton | 7 | 7 | 10 | 8 | 10 | 8 | 10 | 5 | 5 | 6 | 0 | 4 | 4 | 0 | 6 | 7 | 6 | 9 | 6 | 10 | 7 | 9 | 2 | 5 | 0 | 6 | 5 |
| Crabgrass | 8 | 7 | 8 | 9 | 7 | 4 | 3 | 7 | 7 | 7 | 0 | 7 | 8 | 3 | 4 | 6 | 6 | 7 | 8 | 6 | 4 | 3 | 7 | 8 | 0 | 8 | 5 |
| Downy brome | 8 | 10 | 10 | 6 | 6 | 2 | 7 | 5 | 9 | 10 | 4 | 6 | 6 | 6 | 6 | 7 | 9 | 10 | 6 | 5 | 0 | 6 | 5 | 7 | 3 | 5 | 4 |
| Giant foxtail | 10 | 7 | 10 | 10 | 10 | 6 | 10 | 9 | 7 | 10 | 5 | 8 | 9 | 8 | 6 | 8 | 7 | 9 | 9 | 9 | 6 | 10 | 6 | 8 | 3 | 8 | 7 |
| Lambsquarters | 10 | 10 | 10 | 7 | 10 | 6 | 7 | 10 | 10 | 10 | 3 | 10 | 9 | 2 | 9 | 9 | 10 | 10 | 6 | 10 | 6 | 6 | 9 | 10 | 3 | 10 | 9 |
| Morningglory | 10 | 8 | 10 | 9 | 9 | 9 | 10 | 7 | 8 | 10 | 2 | 7 | 7 | 2 | 7 | 10 | 7 | 10 | 8 | 7 | 9 | 9 | 8 | 9 | 0 | 7 | 5 |
| Pigweed | 10 | 10 | 10 | 9 | 10 | 9 | 10 | 4 | 6 | 7 | 3 | 7 | 8 | 7 | 8 | 8 | 10 | 10 | 9 | 10 | 9 | 10 | 9 | 9 | 5 | 8 | 3 |
| Rape | 10 | 10 | 10 | 10 | 10 | 10 | 10 | 10 | 9 | 10 | 4 | 10 | 7 | 4 | 10 | 9 | 10 | 10 | 10 | 10 | 10 | 10 | 6 | 8 | 0 | 9 | 9 |
| Ryegrass | 4 | 10 | 10 | 7 | 6 | 4 | 6 | 5 | 8 | 7 | 4 | 7 | 5 | 6 | 4 | 2 | 7 | 10 | 6 | 4 | 3 | 6 | 4 | 5 | 4 | 6 | 3 |
| Sorghum | 10 | 10 | 10 | 10 | 10 | 9 | 10 | 9 | 10 | 10 | 5 | 10 | 9 | 8 | 7 | 10 | 10 | 10 | 9 | 10 | 9 | 10 | 8 | 10 | 6 | 8 | 8 |
| Soybean | 10 | 10 | 10 | 9 | 10 | 9 | 10 | 9 | 9 | 10 | 3 | 7 | 7 | 5 | 7 | 10 | 9 | 10 | 9 | 9 | 9 | 9 | 8 | 9 | 0 | 6 | 7 |
| Speedwell | 2 | 6 | — | 8 | 6 | 7 | 9 | 4 | 5 | 0 | 0 | 7 | 0 | 5 | 0 | 1 | 6 | — | 7 | 6 | 6 | 7 | 7 | 8 | 0 | 7 | 0 |
| Sugar beet | 10 | 10 | 10 | 10 | 10 | 10 | 8 | 10 | 10 | 9 | 5 | 10 | 3 | 5 | 8 | 10 | 10 | 10 | 10 | 10 | 10 | 8 | 8 | 10 | 0 | 10 | 9 |
| Velvetleaf | 7 | 7 | 10 | 8 | 9 | 8 | 9 | 8 | 7 | 9 | 2 | 5 | 2 | 0 | 6 | 7 | 7 | 10 | 7 | 9 | 7 | 9 | 7 | 7 | 0 | 6 | 6 |
| Wheat | 8 | 8 | 10 | 5 | 4 | 0 | 6 | 8 | 9 | 10 | 4 | 6 | 5 | 3 | 0 | 5 | 8 | 9 | 5 | 3 | 0 | 6 | 5 | 6 | 5 | 0 | 7 |
| Wild buckwheat | 9 | 10 | 10 | 8 | 10 | 9 | 10 | 9 | 5 | 7 | 3 | 7 | 7 | 2 | 9 | 9 | 9 | 10 | 7 | 10 | 9 | 7 | 5 | 9 | 0 | 9 | 6 |
| Wild oat | 9 | 10 | 10 | 3 | 5 | 0 | 4 | 7 | 10 | 10 | 4 | 0 | 4 | 5 | 5 | 8 | 9 | 9 | 0 | 4 | 0 | 3 | 5 | 6 | 4 | 0 | 7 |
| Barnyardgrass | 8 | 4 | 9 | 0 | 0 | 0 | 0 | 0 | 0 | 1 | 0 | 5 | 5 | 0 | 0 | 8 | 0 | 6 | 0 | 0 | 0 | 0 | 0 | 5 | 0 | 0 | 0 |
| Rice Japonica | 8 | 3 | 9 | 5 | 4 | 1 | 1 | 2 | 0 | 0 | 2 | 1 | 6 | 0 | 0 | 6 | 0 | 8 | 2 | 0 | 0 | 0 | 0 | 3 | 0 | 0 | 2 |
| Umbrella sedge | 9 | 3 | 8 | 0 | 3 | 0 | 0 | 3 | 6 | 7 | 0 | 6 | 8 | 0 | 0 | 7 | 1 | 7 | 0 | 2 | 0 | 0 | 0 | 0 | — | 0 | 0 |

POSTEMERGENCE

| | Rate (4 g/ha) COMPOUND | | | | | | | | | | | | | Rate (2 g/ha) COMPOUND |
|---|---|---|---|---|---|---|---|---|---|---|---|---|---|---|
| | 18 | 19 | 21 | 22 | 29 | 30 | 47 | 51 | 52 | 55 | 56 | 58 | 59 | 19 |
| Barley Igri | 9 | 10 | 0 | 5 | 5 | 4 | 5 | 9 | 9 | 0 | 4 | 0 | 2 | 9 |
| Bedstraw | 4 | 9 | 0 | 5 | 6 | 0 | 8 | 9 | 10 | 5 | 8 | 8 | 8 | 5 |
| Blackgrass | 10 | 9 | 2 | 7 | 6 | 6 | 6 | 9 | 10 | 7 | 7 | 4 | 6 | 8 |
| Chickweed | 6 | 10 | 0 | 8 | — | — | 9 | 10 | 10 | — | — | — | — | 9 |
| Corn | 10 | 10 | 6 | 7 | 8 | 8 | 10 | 10 | 10 | 9 | 10 | 9 | 9 | 10 |
| Cotton | 3 | 5 | 0 | 2 | 3 | 0 | 6 | 6 | 8 | 5 | 10 | 4 | 4 | 4 |
| Crabgrass | 6 | 6 | 0 | 6 | 7 | 0 | 5 | 5 | 6 | 7 | 5 | 3 | 2 | 6 |
| Downy brome | 8 | 9 | 0 | 5 | 6 | 6 | 4 | 8 | 10 | 5 | 4 | 0 | 5 | 8 |
| Giant foxtail | 6 | 7 | 5 | 8 | 9 | 6 | 6 | 6 | 8 | 7 | 9 | 5 | 9 | 7 |
| Lambsquarters | 9 | 10 | 0 | 10 | 8 | 2 | 9 | 10 | — | 5 | 10 | 6 | 5 | 10 |
| Morningglory | 6 | 10 | 0 | 7 | 7 | 0 | 10 | 6 | 10 | 6 | 5 | 7 | 9 | 9 |
| Pigweed | 4 | 6 | 0 | 6 | 7 | 7 | 8 | 10 | 10 | 8 | 10 | 9 | 9 | 6 |
| Rape | 8 | 7 | 2 | 7 | 6 | 0 | 9 | 9 | 10 | 8 | 10 | 10 | 10 | 6 |
| Ryegrass | 5 | 3 | 3 | 6 | 3 | 6 | 0 | 5 | 10 | 4 | 3 | 0 | 3 | 0 |
| Sorghum | 8 | 8 | 3 | 10 | 9 | 8 | 10 | 10 | 10 | 9 | 10 | 9 | 10 | 7 |
| Soybean | 7 | 10 | 0 | 6 | 7 | 3 | 10 | 8 | 9 | 8 | 9 | 9 | 9 | 10 |
| Speedwell | 4 | 0 | 0 | 5 | 0 | 3 | 0 | 5 | 0 | 5 | 3 | 6 | 6 | 0 |
| Sugar beet | 9 | 9 | 4 | 10 | 0 | 4 | 10 | 10 | 10 | 10 | 10 | 10 | 7 | 7 |
| Velvetleaf | 5 | 7 | 0 | 3 | 0 | 0 | 6 | 7 | 9 | 4 | 8 | 6 | 6 | 6 |
| Wheat | 9 | 9 | 3 | 6 | 4 | 0 | 4 | 8 | 9 | 3 | 3 | 0 | 5 | 9 |
| Wild buckwheat | 4 | 5 | 2 | 6 | 7 | 0 | 8 | 8 | 9 | 7 | 10 | 7 | 7 | 0 |
| Wild oat | 9 | 8 | 2 | 0 | 3 | 4 | 6 | 6 | 9 | 0 | 3 | 0 | 0 | 5 |
| Barnyardgrass | 0 | 0 | 0 | 5 | 3 | 0 | 6 | 0 | 4 | 0 | 0 | 0 | 0 | 0 |
| Rice Japonica | 0 | 0 | 1 | 1 | 0 | 0 | 4 | 0 | 8 | 0 | 0 | 0 | 0 | 0 |
| Umbrella sedge | 2 | 6 | 0 | 2 | 7 | 0 | 5 | 0 | 5 | 0 | 0 | 0 | 0 | 2 |

PREEMERGENCE

| | Rate (250 g/ha) COMPOUND 5 | Rate (125 g/ha) COMPOUND 42 | Rate (62 g/ha) COMPOUND | | | | | | | | | | | | | | | | |
|---|---|---|---|---|---|---|---|---|---|---|---|---|---|---|---|---|---|---|---|
| | | | 3 | 4 | 5 | 6 | 14 | 18 | 21 | 22 | 29 | 30 | 42 | 47 | 51 | 52 | 55 | 56 | 58 | 59 |
| Barley Igri | 7 | 8 | 6 | 9 | 3 | 9 | 2 | 0 | 0 | 4 | 1 | 0 | 4 | 3 | 0 | 6 | 6 | 5 | 3 | 3 |
| Bedstraw | 9 | 10 | 9 | 10 | 7 | 10 | 0 | 9 | 8 | 8 | 10 | 9 | 9 | 10 | 10 | 10 | 10 | 10 | 10 | 10 |
| Blackgrass | 7 | 9 | 5 | 10 | 3 | 8 | 7 | 10 | 0 | 10 | 10 | 10 | 7 | — | 10 | 10 | 9 | 9 | 9 | 10 |
| Chickweed | 8 | 10 | 7 | 10 | 3 | 8 | 8 | 9 | 5 | 10 | 9 | 5 | 7 | 10 | 10 | 10 | 10 | 10 | 10 | 10 |
| Corn | 0 | 4 | 2 | 9 | 0 | 7 | 2 | 10 | 2 | 9 | 4 | 0 | 2 | 3 | 6 | 10 | 7 | — | 8 | — |
| Cotton | 0 | 7 | 2 | 2 | 0 | 7 | 3 | 5 | 0 | 8 | 4 | 0 | 5 | 0 | 8 | 9 | 6 | 8 | 7 | 6 |
| Crabgrass | 10 | 7 | 8 | 9 | 5 | 10 | 5 | 5 | 0 | 7 | 7 | 4 | 7 | 7 | 9 | 10 | 8 | 10 | 10 | 8 |
| Downy brome | 8 | 10 | 9 | 10 | 6 | 8 | 5 | 0 | 2 | 8 | 9 | 0 | 9 | 8 | 8 | 9 | 3 | 4 | 10 | 10 |
| Giant foxtail | 9 | 10 | 6 | 9 | 6 | 9 | 4 | 4 | 3 | 8 | 9 | 6 | 7 | 7 | 9 | 10 | 8 | 10 | 9 |
| Lambsquarters | 10 | 10 | 10 | 10 | 9 | 10 | 7 | 10 | 9 | 10 | 10 | 9 | 10 | 6 | 10 | 10 | 10 | 10 | 10 | 10 |
| Morningglory | 6 | 6 | 9 | 9 | 4 | 8 | 0 | 3 | 0 | 8 | 3 | 2 | 4 | 4 | 9 | 10 | 10 | 4 | 6 | 8 |
| Pigweed | 9 | 10 | 9 | 9 | 8 | 10 | 7 | 8 | 8 | 10 | 8 | 3 | 10 | 10 | 9 | 10 | 10 | 10 | 10 | 10 |
| Rape | 0 | 10 | 10 | 10 | 0 | 9 | 7 | 6 | 6 | 9 | 5 | 0 | 10 | 7 | 10 | 10 | 10 | 10 | 10 | 10 |
| Ryegrass | 9 | 8 | 8 | 10 | 7 | 8 | 3 | 9 | 3 | 10 | 6 | 5 | 4 | 5 | 10 | 10 | 9 | 10 | 10 |
| Sorghum | 9 | 10 | 9 | 9 | 3 | 10 | 4 | 5 | 0 | 9 | 9 | 6 | 10 | 9 | 7 | 10 | 10 | 10 | 10 | 10 |

TABLE D-continued

| | | | | | | | | | | | | | | | | | | | | | | |
|---|---|---|---|---|---|---|---|---|---|---|---|---|---|---|---|---|---|---|---|---|---|---|
| Soybean | 2 | 7 | 4 | 4 | 2 | 6 | 2 | 4 | 0 | — | 4 | 0 | 6 | 6 | 6 | 10 | 8 | 8 | 7 | 6 |
| Speedwell | 9 | 8 | 10 | 10 | 5 | 9 | 5 | 9 | 0 | 10 | 6 | 10 | 6 | 7 | 8 | 9 | 10 | 10 | 10 | 10 |
| Sugar beet | 9 | 10 | 9 | 10 | 6 | 10 | 9 | 10 | 8 | 10 | 7 | 0 | 10 | 10 | 10 | 10 | 10 | 10 | 10 | 10 |
| Velvetleaf | 3 | 9 | 8 | 9 | 3 | 9 | 7 | 5 | 0 | 7 | 4 | 2 | 8 | 7 | 8 | 10 | 6 | 10 | 7 | 9 |
| Wheat | 8 | 8 | 9 | 9 | 4 | 6 | 0 | 0 | 0 | 3 | 4 | 2 | 6 | 5 | 0 | 7 | 8 | 5 | 4 | 5 |
| Wild buckwheat | 4 | 10 | 4 | 9 | 2 | 9 | 5 | 8 | 8 | 8 | 9 | 7 | 9 | 9 | 9 | 10 | 10 | 10 | 10 | 10 |
| Wild oat | 8 | 4 | 4 | 6 | 3 | 0 | 4 | 4 | 0 | 0 | 0 | 3 | 4 | 7 | 4 | 6 | 2 | 5 | 0 | 0 |

PREEMERGENCE

| | Rate (31 g/ha) COMPOUND | | | | | | | | | | | | | | | Rate (16 g/ha) COMPOUND | | | | | | | | | | |
|---|---|---|---|---|---|---|---|---|---|---|---|---|---|---|---|---|---|---|---|---|---|---|---|---|---|---|
| | 14 | 18 | 19 | 21 | 22 | 29 | 30 | 42 | 47 | 51 | 52 | 55 | 56 | 58 | 59 | 3 | 4 | 5 | 6 | 14 | 18 | 19 | 21 | 22 | 29 | 30 | 42 |
| Barley Igri | 0 | 0 | 0 | 0 | 3 | 0 | 0 | 3 | 2 | 0 | 4 | 4 | 3 | 0 | 0 | 3 | 0 | 0 | 4 | 0 | 0 | 0 | 0 | 2 | 0 | 0 | 3 |
| Bedstraw | 0 | 4 | 5 | 4 | 6 | 9 | 5 | 8 | 9 | 10 | 10 | 9 | 10 | 10 | 10 | 7 | 10 | 3 | 9 | 0 | 3 | 5 | 3 | 3 | 6 | 5 | 6 |
| Blackgrass | 4 | 8 | 9 | 0 | 10 | 9 | 7 | 6 | 9 | 10 | 9 | 9 | 8 | 9 | 10 | 4 | 6 | 2 | 6 | 2 | 6 | 6 | 0 | 8 | 8 | 7 | 5 |
| Chickweed | 7 | 7 | 10 | 2 | 10 | 8 | 3 | 6 | 10 | 10 | 10 | 10 | 10 | 10 | 10 | 4 | 10 | 0 | 8 | 5 | 7 | 10 | 0 | 8 | 7 | 3 | 5 |
| Corn | 0 | 4 | 2 | 0 | 7 | 3 | 0 | 0 | 2 | 6 | 10 | 7 | 3 | 6 | 4 | 2 | 4 | 0 | 6 | 0 | 2 | 2 | 0 | 2 | 2 | 0 | 0 |
| Cotton | 2 | 3 | 4 | 0 | 7 | 3 | 0 | 2 | 0 | 6 | 9 | 5 | 4 | 6 | 4 | 2 | 1 | 0 | 6 | 0 | 2 | 3 | 0 | 3 | 2 | 0 | 0 |
| Crabgrass | 2 | 4 | 5 | 0 | 6 | 6 | 3 | 3 | 5 | 8 | 10 | 6 | 10 | 10 | 6 | 7 | 5 | 0 | 6 | 0 | 2 | 5 | 0 | 5 | 4 | 0 | 0 |
| Downy brome | 3 | 0 | 9 | 2 | 6 | 3 | 0 | 8 | 6 | 6 | 8 | 9 | 3 | 2 | 8 | 9 | 10 | 3 | 5 | 2 | 0 | 7 | 0 | 3 | 0 | 0 | 5 |
| Giant foxtail | 2 | 2 | 8 | 0 | 8 | 6 | 2 | 6 | 6 | 5 | 9 | 6 | 10 | 8 | 6 | 4 | 6 | 0 | 0 | 0 | 7 | 0 | 6 | 5 | 0 | 3 |
| Lambsquarters | 7 | 10 | 10 | 2 | 10 | 9 | 9 | 10 | 6 | 10 | 10 | 10 | 10 | 10 | 10 | 10 | 10 | 2 | 10 | 2 | 5 | 10 | 0 | 9 | 5 | 0 | 9 |
| Morningglory | 0 | 2 | 0 | 0 | 7 | 2 | 0 | 2 | 3 | 9 | 10 | 9 | 4 | 6 | 8 | 5 | 5 | 3 | 6 | 0 | 0 | 0 | 0 | 7 | 0 | 0 | 0 |
| Pigweed | 2 | 7 | 9 | 2 | 9 | 6 | 3 | 10 | 10 | 9 | 9 | 10 | 10 | 10 | 10 | 9 | 9 | 6 | 10 | 0 | 7 | 9 | 0 | 8 | 5 | 0 | 10 |
| Rape | 3 | 6 | 6 | 6 | 8 | 2 | 0 | 6 | 6 | 9 | 10 | 10 | 7 | 10 | 10 | 5 | 5 | 0 | 8 | 0 | 6 | 6 | 6 | 8 | 0 | 0 | 5 |
| Ryegrass | 2 | 4 | 5 | 2 | 10 | 5 | 0 | 4 | 4 | 7 | 10 | 10 | 8 | 6 | 10 | 2 | 6 | 3 | 2 | 0 | 3 | 5 | 0 | 5 | 4 | 0 | 3 |
| Sorghum | 2 | 2 | 9 | 0 | 9 | 8 | 4 | 6 | 8 | 3 | 10 | 10 | 10 | 10 | 9 | 3 | 4 | 0 | 10 | 0 | 0 | 7 | 0 | 9 | 7 | 2 | 4 |
| Soybean | 0 | 2 | 3 | 0 | 4 | 3 | 0 | 3 | 6 | 5 | 10 | 7 | 8 | 6 | 6 | 0 | 1 | 2 | 3 | 0 | 0 | 0 | 0 | 4 | 2 | 0 | 0 |
| Speedwell | 5 | 9 | 5 | 0 | 9 | 5 | 6 | 6 | — | 8 | 9 | 10 | 9 | 10 | 10 | 9 | 9 | 3 | 8 | 2 | 8 | 3 | 0 | 8 | 5 | — | 4 |
| Sugar beet | 5 | 9 | 10 | 5 | 10 | 6 | 0 | 7 | 10 | 10 | 10 | 10 | 10 | 10 | 10 | 8 | 8 | 5 | 10 | 5 | 9 | 7 | 5 | 9 | 4 | 0 | 6 |
| Velvetleaf | 5 | 2 | 3 | 0 | 6 | 3 | 0 | 6 | 6 | 7 | 10 | 6 | 10 | 7 | 6 | 5 | 5 | 0 | 8 | 4 | 0 | 2 | 0 | 5 | 2 | 0 | 6 |
| Wheat | 0 | 0 | 0 | 0 | 2 | 3 | 0 | 4 | 3 | 0 | 6 | 5 | 3 | 0 | 5 | 4 | 7 | 0 | 3 | 0 | 0 | 0 | 0 | 0 | 0 | 0 | 3 |
| Wild buckwheat | 2 | 6 | 8 | 6 | 7 | 8 | 6 | 8 | 6 | 8 | 10 | 10 | 10 | 10 | 9 | 3 | 3 | — | 6 | 0 | 3 | 3 | 2 | 6 | 5 | 4 | 6 |
| Wild oat | 2 | 2 | 3 | 0 | 0 | 0 | 0 | 2 | 0 | 3 | 5 | 0 | 3 | 0 | 0 | 3 | 2 | 0 | 0 | 0 | 1 | 0 | 0 | 0 | 0 | 0 | 1 |

PREEMERGENCE

| | Rate (16 g/ha) COMPOUND | | | | | | | Rate (8 g/ha) COMPOUND | | | | | | | | | | | | | Rate (4 g/ha) COMPOUND | | | | |
|---|---|---|---|---|---|---|---|---|---|---|---|---|---|---|---|---|---|---|---|---|---|---|---|---|---|
| | 47 | 51 | 52 | 55 | 56 | 58 | 59 | 14 | 18 | 19 | 21 | 22 | 29 | 30 | 42 | 47 | 51 | 52 | 55 | 56 | 58 | 59 | 3 | 4 | 5 | 6 | 14 |
| Barley Igri | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 2 | 0 | 0 | 2 | 0 |
| Bedstraw | 8 | 7 | 10 | 9 | 10 | 10 | 10 | 0 | 3 | 3 | 0 | 0 | 6 | 3 | 4 | 6 | 6 | 7 | 9 | 5 | 9 | 9 | 4 | 8 | 0 | 8 | 0 |
| Blackgrass | 9 | 7 | 8 | 9 | 7 | 9 | 6 | 0 | 5 | 6 | 0 | 6 | 6 | 3 | 0 | 5 | 6 | 8 | 9 | 7 | 8 | 6 | 0 | 0 | 0 | 2 | 0 |
| Chickweed | 10 | 10 | 10 | 10 | 10 | 10 | 10 | 5 | 5 | 10 | 0 | 7 | 7 | 3 | 3 | 5 | 9 | 10 | 10 | 10 | 10 | 10 | 2 | 8 | 0 | 2 | 2 |
| Corn | 0 | 2 | 10 | 6 | — | 3 | 4 | 0 | 0 | 0 | 0 | 0 | 2 | — | 0 | 0 | 0 | 7 | 3 | — | 0 | — | 0 | 1 | 0 | 3 | 0 |
| Cotton | 0 | 5 | 9 | 4 | 3 | 5 | 4 | 0 | 0 | 2 | 0 | 3 | 0 | 0 | 0 | 3 | 8 | 3 | 3 | 4 | 2 | 0 | 0 | 0 | 3 | 0 |
| Crabgrass | 4 | 4 | 9 | 5 | 10 | 7 | 5 | 0 | 0 | 2 | 0 | 3 | 0 | 0 | 0 | 3 | 3 | 9 | 4 | 7 | 6 | 4 | 6 | 4 | 0 | 4 | 0 |
| Downy brome | 3 | 3 | 7 | 5 | 0 | 0 | 2 | 0 | 0 | 0 | 0 | 2 | 0 | 0 | 3 | 0 | 0 | 4 | 0 | 0 | 0 | 0 | 3 | 3 | 0 | 2 | 0 |
| Giant foxtail | 3 | 4 | 8 | 4 | 10 | 7 | 5 | 0 | 0 | 3 | 0 | 5 | 4 | 0 | 0 | 0 | 2 | 8 | 3 | 4 | 6 | 4 | 3 | 4 | 0 | 0 | 0 |
| Lambsquarters | 0 | 9 | 10 | 9 | 10 | 9 | 7 | 0 | 4 | 5 | 0 | 5 | 9 | — | 0 | — | 0 | 7 | 10 | 3 | 10 | 9 | 3 | 5 | 9 | 0 | 10 | 0 |
| Morningglory | 2 | 7 | 8 | 8 | 4 | 6 | 6 | 0 | 0 | 0 | 0 | 5 | 0 | 0 | 0 | 0 | 5 | 7 | 7 | 3 | 6 | 5 | 1 | 2 | 0 | 4 | 0 |
| Pigweed | 8 | 8 | 8 | 8 | 10 | 10 | 10 | 0 | 5 | 7 | 0 | 8 | 4 | 0 | 7 | 7 | 8 | 8 | 8 | 9 | 10 | 10 | 8 | 7 | 3 | 8 | 0 |
| Rape | 5 | 6 | 10 | 6 | 5 | 3 | 10 | 0 | 6 | 6 | 6 | 7 | 0 | 0 | 3 | 4 | 5 | 9 | 6 | 5 | 2 | 5 | 3 | 0 | 0 | 7 | 0 |
| Ryegrass | 3 | 3 | 10 | 7 | 5 | 4 | 10 | 0 | 1 | 2 | 0 | 3 | 0 | 0 | 2 | 0 | 0 | 7 | 7 | 0 | 3 | 0 | 0 | 3 | 0 | 0 | 0 |
| Sorghum | 4 | 2 | 10 | 6 | 9 | 10 | 6 | 0 | 0 | 2 | 0 | 7 | 5 | 0 | 2 | 3 | 0 | 10 | 0 | 3 | 7 | 4 | 0 | 0 | 0 | 4 | 0 |
| Soybean | 3 | 3 | 10 | 5 | 6 | 5 | 6 | 0 | 0 | 0 | 0 | 2 | 0 | 0 | 0 | 2 | 2 | 9 | 4 | 4 | 4 | 3 | 0 | 0 | 2 | 2 | 0 |
| Speedwell | 4 | 7 | 8 | 10 | 9 | 10 | 10 | 0 | 6 | 3 | 0 | 8 | 5 | 3 | 3 | 0 | 7 | 7 | 10 | 9 | 9 | 9 | — | 7 | 3 | 7 | 0 |
| Sugar beet | 6 | 10 | 10 | 10 | 10 | 10 | 10 | 3 | 4 | — | 4 | 9 | 4 | 0 | 5 | 5 | 9 | 10 | 9 | 9 | 10 | 9 | 3 | 8 | 0 | 2 | 0 |
| Velvetleaf | 6 | 4 | 10 | 4 | 6 | 5 | 5 | 4 | 0 | 0 | 0 | 3 | 0 | 0 | 0 | 4 | 4 | 8 | 3 | 6 | 3 | 4 | 3 | 4 | 0 | 4 | 0 |
| Wheat | 0 | 0 | 4 | 5 | 2 | 0 | 0 | 0 | 0 | 0 | 0 | 0 | 0 | 0 | 0 | 0 | 0 | 0 | 0 | 0 | 0 | 0 | 0 | 2 | 0 | 2 | 0 |
| Wild buckwheat | 6 | 7 | 9 | 8 | 9 | 10 | 8 | 0 | 3 | 3 | 0 | 6 | 5 | 0 | 2 | 0 | 7 | 9 | 8 | 8 | 8 | 8 | 2 | 0 | 0 | 5 | 0 |
| Wild oat | 0 | 0 | 4 | 0 | 0 | 0 | 0 | 0 | 0 | 0 | 0 | 0 | 0 | 0 | 0 | 0 | 0 | 3 | 0 | 0 | 0 | 0 | 2 | 2 | 0 | 0 | 0 |

PREEMERGENCE

| | Rate (4 g/ha) COMPOUND | | | | | | | | | | | | | Rate (2 g/ha) COMPOUND |
|---|---|---|---|---|---|---|---|---|---|---|---|---|---|---|
| | 18 | 19 | 21 | 22 | 29 | 30 | 47 | 51 | 52 | 55 | 56 | 58 | 59 | 19 |
| Barley Igri | 0 | 0 | 0 | 0 | 0 | 0 | 0 | 0 | 0 | 0 | 0 | 0 | 0 | 0 |
| Bedstraw | 0 | 0 | 0 | 0 | 2 | 0 | 3 | 5 | 7 | 3 | 5 | 8 | — | 0 |
| Blackgrass | 3 | 4 | 0 | 3 | 5 | 3 | 4 | 5 | 8 | 8 | 4 | 4 | 5 | 3 |
| Chickweed | 3 | 9 | 0 | 6 | 3 | — | 0 | 8 | 10 | 10 | 10 | 9 | 9 | 3 |
| Corn | 0 | 0 | 0 | 0 | 0 | 2 | 0 | 0 | 4 | 0 | 0 | 0 | — | 0 |
| Cotton | 0 | 0 | 0 | 2 | 0 | 0 | 0 | 7 | 2 | 2 | 3 | 0 | 0 |
| Crabgrass | 0 | 0 | 0 | 0 | 0 | 0 | 0 | 0 | 8 | 3 | 5 | 3 | 3 | 0 |
| Downy brome | 0 | 0 | 0 | 0 | 0 | 0 | 0 | 3 | 0 | 0 | 0 | 0 | 0 |
| Giant foxtail | 0 | 2 | 0 | 2 | 3 | 0 | 0 | 0 | 6 | 2 | 0 | 4 | 3 | 0 |
| Lambsquarters | 0 | 0 | 0 | 7 | 0 | — | 0 | 4 | 7 | 0 | 10 | — | 3 | 0 |
| Morningglory | 0 | 0 | 0 | 3 | 0 | 0 | 0 | 3 | 7 | 5 | 3 | 5 | 4 | 0 |
| Pigweed | 4 | 7 | 0 | 7 | 3 | 0 | 7 | 5 | 8 | 8 | 9 | 8 | 8 | 3 |
| Rape | 6 | 6 | 6 | 5 | 0 | 0 | 3 | 3 | 8 | 6 | 3 | 0 | 4 | 6 |
| Ryegrass | 0 | 2 | 0 | 0 | 0 | 0 | 0 | 0 | 6 | 4 | 0 | 0 | 0 | 0 |
| Sorghum | 0 | 0 | 0 | 2 | 2 | 0 | 2 | 0 | 7 | 0 | 2 | 5 | 3 | 0 |

TABLE D-continued

| | | | | | | | | | | | | | | |
|---|---|---|---|---|---|---|---|---|---|---|---|---|---|---|
| Soybean | 0 | 0 | 0 | 0 | 0 | 0 | 0 | 0 | 7 | 3 | 4 | 3 | 2 | 0 |
| Speedwell | 4 | 2 | 0 | 7 | 0 | 2 | 0 | 5 | 7 | 8 | 5 | 9 | 8 | 0 |
| Sugar beet | 0 | 3 | 0 | 9 | 0 | 0 | 0 | 3 | 10 | 8 | 6 | 9 | 8 | 0 |
| Velvetleaf | 0 | 0 | 0 | 1 | 0 | 0 | 3 | 2 | 5 | 0 | 4 | 0 | 4 | 0 |
| Wheat | 0 | 0 | 0 | 0 | 0 | 0 | 0 | 0 | 0 | 0 | 0 | 0 | 0 | 0 |
| Wild buckwheat | 0 | 2 | 0 | 5 | 0 | 0 | 0 | 0 | 9 | 6 | 6 | 8 | 0 | 0 |
| Wild oat | 0 | 0 | 0 | 0 | 0 | 0 | 0 | 0 | 0 | 0 | 0 | 0 | 0 | 0 |

TEST E

Plastic pots were partially filled with silt loam soil. The soil was then flooded with water and Japonica rice (Oryza sativa) sprouted seeds and 1.5 leaf transplants were planted in the soil.

Seeds of barnyardgrass (*Echinochloa crus-galli*) were planted in saturated soil and plants grown to the 1 leaf and 2 leaf stages for testing. At testing, the water level for all plantings was raised to 2 cm above the soil surface. Chemical treatments were formulated in a non-phytotoxic solvent and applied directly to the paddy water.

Treated plants and controls were maintained in a greenhouse for approximately 21 days, after which all species were compared to controls and visually evaluated. Plant response ratings, summarize in Table E are reported on a 0 to 10 scale where 0 is no effect and 10 is complete control. A dash (—) response means no test result.

TABLE E

| | COMPOUND | | | | |
|---|---|---|---|---|---|
| | Rate (500 g/ha) 6 | Rate (250 g/ha) 6 | Rate (100 g/ha) 6 | Rate (40 g/ha) 6 | Rate (16 g/ha) 6 |
| Flood | | | | | |
| 1-LF B.Y. Grass | 10 | 10 | 9 | 4 | 4 |
| 2-LF B.Y. Grass | 7 | 6 | 3 | 3 | 8 |
| Jap Direct Seed | 9 | 9 | 9 | 5 | 3 |
| Jap Rice Eff | 9 | 8 | 8 | 6 | 4 |

TEST G

Seeds, rhizomes, or plant parts of alfalfa (*Medicago sativa*), barnyardgrass (*Echinochloa crus-galli*), bermudagrass (*Cynodon dactylon*), broadleaf signalgrass (*Brachiaria plantaginea*), common ragweed (*Ambrosia elatior*), field bindweed (*Convolvulus* spp.), guineagrass (*Panicum maximum*), johnsongrass (*Sorghum halepense*), Kentucky bluegrass (*Poa pratensis*), large crabgrass (*Digitaria sanguinalis*), P. J. legume (*Pueraria javanica*), pitted morningglory (*Ipomoea lacunosa*), purple nutsedge (*Cyperus rotundus*), smooth crabgrass (*Digitaria ischaemum*), purslane (*Portulaca oleracea*), TX panicum (*Panicum Texas*), and yellow nutsedge (*Cyperus esculentus*) were planted into greenhouse pots containing greenhouse planting medium. Each pot contained only one plant species. The test compound was dissolved in a non-phytotoxic solvent and applied preemergence and/or postemergence to the plants. Preemergence applications were made within one day of planting the seeds or plant parts. Postemergence applications were applied when the plants were in the two to four leaf stage (three to twenty cm).

Kentucky bluegrass was treated postemergence only. Test chemicals were dissolved in a non-phytotoxic solvent and applied preemergence and postemergence to the plants. Untreated control plants and treated plants were placed in the greenhouse and visually evaluated for injury at 13 to 21 days after herbicide application. Plant response ratings, summarized in Table G, are based on a 0 to 10 scale where 0 is no injury and 10 is complete control.

TABLE G

| | COMPOUND |
|---|---|
| Rate (64 g/ha) | 4 |
| POSTEMERGENCE | |
| Alfalfa | 10 |
| Barnyardgrass | 9 |
| Bermudagrass | 8 |
| Brdlf sgnalgrass | 9 |
| Field bindweed | 10 |
| Guineagrass | 8 |
| Johnsongrass | 10 |
| KY. Bluegrass | 2 |
| Large crabgrass | 10 |
| P.J. Legume | — |
| Pitted mrnglory | 8 |
| Purple nutsedge | 10 |
| Purslane | 7 |
| Ragweed | 9 |
| Smooth crbgrass | 9 |
| TX panicum | 7 |
| Yellow nutsedge | 5 |
| Rate (64 g/ha) | 4 |
| PREEMERGENCE | |
| Alfalfa | 8 |
| Barnyardgrass | 5 |
| Bermudagrass | 9 |
| Brdlf sgnalgrass | 10 |
| Field bindweed | 8 |
| Guineagrass | 9 |
| Johnsongrass | 9 |
| KY. Bluegrass | — |
| Large crabgrass | 9 |
| P.J. Legume | 8 |
| Pitted mrnglory | 7 |
| Purple nutsedge | 10 |
| Purslane | 9 |
| Ragweed | 9 |
| Smooth crbgrass | 9 |
| TX panicum | 10 |
| Yellow nutsedge | 10 |
| Rate (32 g/ha) | 4 |
| POSTEMERGENCE | |
| Alfalfa | 9 |
| Barnyardgrass | 10 |
| Bermudagrass | 5 |
| Brdlf sgnalgrass | 10 |
| Field bindweed | 8 |
| Guineagrass | 8 |
| Johnsongrass | 10 |
| KY. Bluegrass | 2 |
| Large crabgrass | 9 |
| P.J. Legume | — |
| Pitted mrnglory | 8 |
| Purple nutsedge | 10 |
| Purslane | 7 |
| Ragweed | 10 |
| Smooth crbgrass | 9 |
| TX panicum | 7 |
| Yellow nutsedge | 5 |
| Rate (32 g/ha) | 4 |
| PREEMERGENCE | |
| Alfalfa | 8 |
| Barnyardgrass | 1 |
| Bermudagrass | 7 |
| Brdlf sgnalgrass | 10 |
| Field bindweed | 8 |
| Guineagrass | 8 |

TABLE G-continued

| | COMPOUND |
|---|---|
| Johnsongrass | 8 |
| KY. Bluegrass | — |
| Large crabgrass | 5 |
| P.J. Legume | 7 |
| Pitted mrnglory | 3 |
| Purple nutsedge | 10 |
| Purslane | 9 |
| Ragweed | 9 |
| Smooth crbgrass | 9 |
| TX panicum | 9 |
| Yellow nutsedge | 9 |
| Rate (16 g/ha) | 4 |
| POSTEMERGENCE | |
| Alfalfa | 7 |
| Barnyardgrass | 8 |
| Bermudagrass | 4 |
| Brdlf sgnalgrass | 8 |
| Field bindweed | 8 |
| Guineagrass | 6 |
| Johnsongrass | 9 |
| KY. Bluegrass | 2 |
| Large crabgrass | 8 |
| P.J. Legume | — |
| Pitted mrnglory | 6 |
| Purple nutsedge | 6 |
| Purslane | 4 |
| Ragweed | 9 |
| Smooth crbgrass | 8 |
| TX panicum | 7 |
| Yellow nutsedge | 5 |
| Rate (16 g/ha) | 4 |
| PREEMERGENCE | |
| Alfalfa | 7 |
| Barnyardgrass | 0 |
| Bermudagrass | 3 |
| Brdlf sgnalgrass | 9 |
| Field bindweed | 8 |
| Guineagrass | 6 |
| Johnsongrass | 8 |
| KY. Bluegrass | — |
| Large crabgrass | 1 |
| P.J. Legume | 7 |
| Pitted mrnglory | 3 |
| Purple nutsedge | 10 |
| Purslane | 9 |
| Ragweed | 9 |
| Smooth crbgrass | 6 |
| TX panicum | 8 |
| Yellow nutsedge | 6 |
| Rate (4 g/ha) | 4 |
| POSTEMERGENCE | |
| Alfalfa | 6 |
| Barnyardgrass | 7 |
| Bermudagrass | 3 |
| Brdlf sgnalgrass | 8 |
| Field bindweed | 8 |
| Guineagrass | 6 |
| Johnsongrass | 9 |
| KY. Bluegrass | 2 |
| Large crabgrass | 6 |
| P.J. Legume | — |
| Pitted mrnglory | 1 |
| Purple nutsedge | 1 |
| Purslane | 4 |
| Ragweed | 9 |
| Smooth crbgrass | 3 |
| TX panicum | 7 |
| Yellow nutsedge | 3 |
| Rate (4 g/ha) | 4 |
| PREEMERGENCE | |
| Alfalfa | 6 |
| Barnyardgrass | 0 |
| Bermudagrass | 0 |
| Brdlf sgnalgrass | 8 |
| Field bindweed | 4 |
| Guineagrass | 1 |
| Johnsongrass | 2 |
| KY. Bluegrass | — |
| Large crabgrass | 0 |
| P.J. Legume | 5 |
| Pitted mrnglory | 2 |
| Purple nutsedge | 5 |
| Purslane | 9 |
| Ragweed | 6 |
| Smooth crbgrass | 2 |
| TX panicum | 3 |
| Yellow nutsedge | 0 |
| Rate (1 g/ha) | 4 |
| POSTEMERGENCE | |
| Alfalfa | 3 |
| Barnyardgrass | 1 |
| Bermudagrass | 0 |
| Brdlf sgnalgrass | 8 |
| Field bindweed | 4 |
| Guineagrass | 3 |
| Johnsongrass | 9 |
| KY. Bluegrass | 0 |
| Large crabgrass | 4 |
| P.J. Legume | — |
| Pitted mrnglory | 0 |
| Purple nutsedge | — |
| Purslane | 1 |
| Ragweed | 1 |
| Smooth crbgrass | 0 |
| TX panicum | 3 |
| Yellow nutsedge | 2 |
| Rate (1 g/ha) | 4 |
| PREEMERGENCE | |
| Alfalfa | 5 |
| Barnyardgrass | 0 |
| Bermudagrass | 0 |
| Brdlf sgnalgrass | 0 |
| Field bindweed | 1 |
| Guineagrass | 0 |
| Johnsongrass | 1 |
| KY. Bluegrass | — |
| Large crabgrass | 0 |
| P.J. Legume | 5 |
| Pitted mrnglory | 3 |
| Purple nutsedge | 2 |
| Purslane | 2 |
| Ragweed | 1 |
| Smooth crbgrass | 1 |
| TX panicum | 0 |
| Yellow nutsedge | 0 |

TEST H

Seeds selected from crop and weed species consisting of blackgrass (*Alopecurus myosuroides*), catchweed bedstraw (*Galium aparine*), chickweed (*Stellariamedia*), lambsquarters (*Chenopodium album*), scentless chamomile (*Matricaria inodora*), speedwell (*Veronica persica*), sugar beet (*Beta vulgaris*), field violet (*Viola arvensis*), wheat (*Triticum aestivum*), wild buckwheat (*Polygonum convolvulus*), wild oat (*Avena fatua*) were planted and treated preemergence with test chemicals dissolved in a non-phytotoxic solvent. Selected species from this list of crops and weeds were also treated with postemergence applications of test chemicals.

Plants ranged in height from two to twenty cm (two to three leaf stage) for postemergence treatments. Treated plants and controls were maintained in a greenhouse for approximately 24 days, after which all species were compared to controls and visually evaluated.

The ratings, summarized in Table H, are based on a scale of 0 to 10 where 0 is no effect and 10 is complete control. A dash (—) response means no test.

TABLE H

| | COMPOUND |
|---|---|
| Rate (64 g/ha) | 11 |
| POSTEMERGENCE | |

TABLE H-continued

| | COMPOUND |
|---|---|
| Bedstraw | 0 |
| Blackgrass | 10 |
| Chickweed | 5 |
| Field violet | 7 |
| Lambsquarters | 7 |
| Persian Speedwell | 0 |
| Sntls Chamomile | 5 |
| Sugar beet | 4 |
| Wheat | 8 |
| Wild buckwheat | 7 |
| Wild oat | 8 |
| Rate (32 g/ha) | 11 |
| POSTEMERGENCE | |
| Bedstraw | 0 |
| Blackgrass | 9 |
| Chickweed | 4 |
| Field violet | 4 |
| Lambsquarters | 5 |
| Persian Speedwell | 0 |
| Sntls Chamomile | 3 |
| Sugar beet | 3 |
| Wheat | 8 |
| Wild buckwheat | 7 |
| Wild oat | 7 |
| Rate (16 g/ha) | 11 |
| POSTEMERGENCE | |
| Bedstraw | 0 |
| Blackgrass | 8 |
| Chickweed | 4 |
| Field violet | 3 |
| Lambsquarters | 0 |
| Persian Speedwell | 0 |
| Sntls Chamomile | 0 |
| Sugar beet | 2 |
| Wheat | 6 |
| Wild buckwheat | 2 |
| Wild oat | 5 |
| Rate (8 g/ha) | 11 |
| POSTEMERGENCE | |
| Bedstraw | 0 |
| Blackgrass | 4 |
| Chickweed | 0 |
| Field violet | 0 |
| Lambsquarters | 0 |
| Persian Speedwell | 0 |
| Sntls Chamomile | 0 |
| Sugar beet | 0 |
| Wheat | 5 |
| Wild buckwheat | 0 |
| Wild oat | 0 |

What is claimed is:

1. A compound of the formula

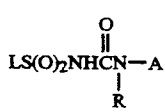

I wherein:
L is

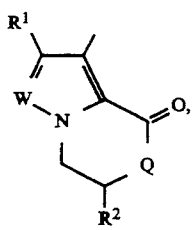

L-1

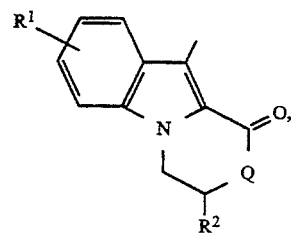

L-2

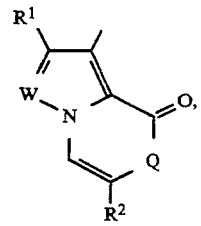

L-3

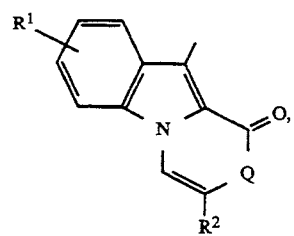

L-4

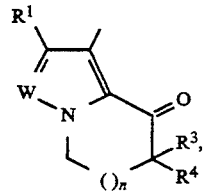

L-5

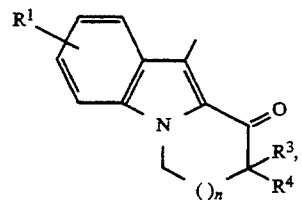

L-6

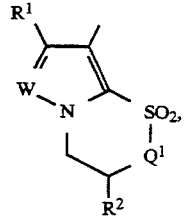

L-7

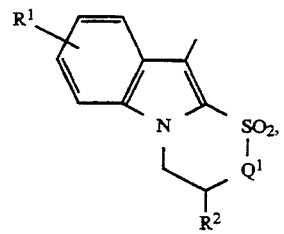

L-8

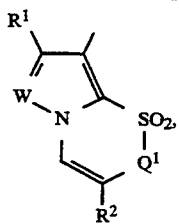 L-9

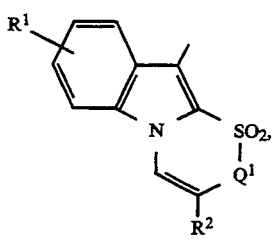 L-10

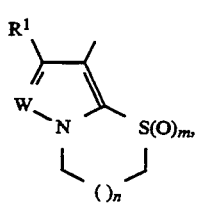 L-11

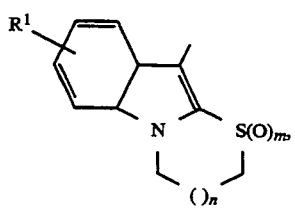 L-12

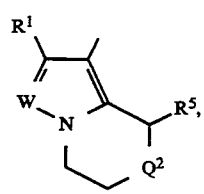 L-13

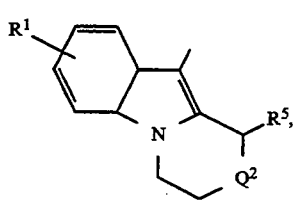 L-14

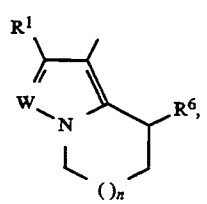 L-15

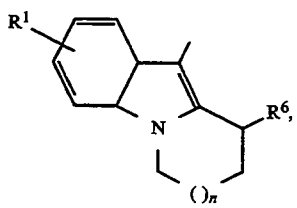 L-16

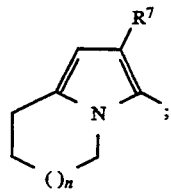 L-17

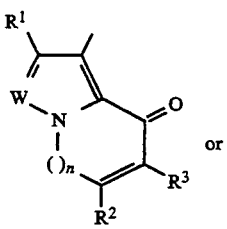 L-18

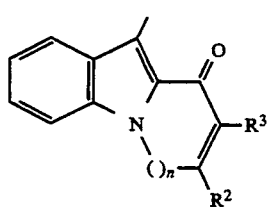 L-19

Q is O, S or $NR^8$;
$Q^1$ is O or $NR^8$;
$Q^2$ is O, S or $NCH_3$;
R is H or $CH_3$;
$R^1$ is H, $CH_3$, Cl or Br;
$R^2$ is H or $CH_3$;
$R^3$ is H, $CH_3$, F, Cl or Br;
$R^4$ is H, $CH_3$, F, Cl or Br;
$R^5$ is H or $C_1-C_3$ alkyl;
$R^6$ is H, $C_1-C_3$ alkyl, $C_1-C_3$ alkoxy, F, Cl, ($C_1-C_2$ alkyl)carbonyloxy or $C_1-C_2$ alkylsulfonyloxy;
$R^7$ is $CO_2R^9$, $CO_2NR^{10}R^{11}$, $S(O)_2NR^{10}R^{11}$ or $S(O)_2R^{12}$;
$R^8$ is H, $C_1-C_4$ alkyl, $C_1-C_4$ haloalkyl, allyl, propargyl or $C_2-C_4$ alkoxyalkyl;
$R^9$ is $C_1-C_4$ alkyl;
$R^{10}$ is H or $C_1-C_2$ alkyl;
$R^{11}$ is H or $C_1-C_2$ alkyl;
$R^{12}$ is $C_1-C_3$ alkyl;
w is $CR^{13}$ or N;
$R^{13}$ is H, $CH_3$, Cl or Br;
m is 0, 1 or 2;
n is 0 or 1;
A is

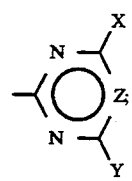 A-1

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino or di($C_1-C_3$ alkyl)amino;
Y is H, $C_1-C_4$ alkyl, $C_1-C_4$ alkoxy, $C_1-C_4$ haloalkoxy, $C_1-C_4$ alkylthio, $C_1-C_4$ haloalkylthio, $C_2-C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido, cyano,

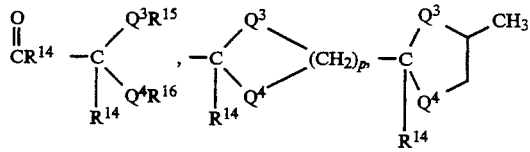

or $N(OCH_3)CH_3$;

p is 2 or 3;
$Q^3$ and $Q^4$ are independently O or S;
$R^{14}$ is H or $C_1$-$C_3$ alkyl;
$R^{15}$ and $R^{16}$ are independently $C_1$-$C_3$ alkyl; and
Z is CH, $CCH_3$, $CC_2H_5$, CCl or CBr;
and their agriculturally suitable salts; provided that
1) when X is halogen, then Z is CH and Y is $OCH_3$, $OCH_2CH_3$, $NH_2$, $NHCH_3$, $N(CH_3)_2$, $OCF_2H$, $OCF_2Br$ or $N(OCH_3)CH_3$; and
2) when X or Y is $C_1$ haloalkoxy, then Z is CH.

2. The compounds of claim 1 where
X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$;
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH\!=\!CH_2$, $OCH_2C\!\equiv\!CH$, $OCH_2CH_2OCH_3$, $CH_2SCH_3$,

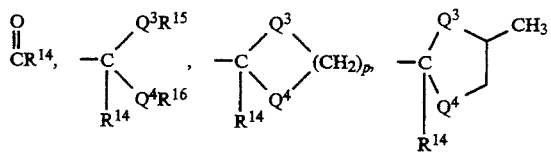

$OCF_2H$, $SCF_2H$, cyclopropyl, $C\!\equiv\!CH$ or $C\!\equiv\!CCH_3$;
$R^{14}$ is H or $CH_3$;
$R^{15}$ and $R^{16}$ are independently $CH_3$ or $CH_2CH_3$;
Z is CH; and
R is H.

3. The compounds of claim 2 wherein L is L-1, L-2, L-3, L-7, L-8 or L-9.

4. The compounds of claim 3 where $R^8$ is H, $C_1$-$C_3$ alkyl or allyl.

5. The compounds of claim 4 where
Z is CH;
X is $CH_3$, $OCH_3$, $OCH_2CH_3$, Cl or $OCF_2H$; and
Y is $CH_3$, $OCH_3$, $CH(OCH_3)_2$ or $OCF_2H$.

6. The compounds of claim 5 where L is L-1; and W is CH.

7. The compounds of claim 5 where L is L-2.

8. The compounds of claim 5 where L is L-7.

9. The compound of claim 1 which is 3,4-dihydro-N-[[(4-methoxy-6-methyl-2-pyrimidin-2-yl)-amino]carbonyl]-1-oxo-1H-[1,4]-oxazine[4,3-a]indole-10-sulfonamide.

10. The compound of claim 1 which is N-[[(4,6-dimethoxy-2-pyrimidinyl)amino]carbonyl]-3-4-dihydro-2H-pyrrolo[1,2-e]-[1,2,5]thiadiazine-8-sulfonamide, 1,1-dioxide.

11. The compound of claim 1 which is N-[[(4,6-dimethoxy-2-pyrimidinyl)amino]carbonyl]-3,4-dihydro-2-methyl-2H-pyrazolo-[1,5-e][1,2,5]thiadiazine-8-sulfonamide,1,1,-dioxide.

12. An agriculturally suitable composition for controlling the growth of undesired vegetation comprising an effective amount of a compound of claim 1 and at least one of the following: surfactant, solid diluent or liquid diluent.

13. An agriculturally suitable composition for controlling the growth of undesired vegetation comprising an effective amount of a compound of claim 2 and at least one of the following: surfactant, solid diluent or liquid diluent.

14. An agriculturally suitable composition for controlling the growth of undesired vegetation comprising an effective amount of a compound of claim 3 and at least one of the following: surfactant, solid diluent or liquid diluent.

15. An agriculturally suitable composition for controlling the growth of undesired vegetation comprising an effective amount of a compound of claim 4 and at least one of the following: surfactant, solid diluent or liquid diluent.

16. An agriculturally suitable composition for controlling the growth of undesired vegetation comprising an effective amount of a compound of claim 5 and at least one of the following: surfactant, solid diluent or liquid diluent.

17. An agriculturally suitable composition for controlling the growth of undesired vegetation comprising an effective amount of a compound of claim 6 and at least one of the following: surfactant, solid diluent or liquid diluent.

18. An agriculturally suitable composition for controlling the growth of undesired vegetation comprising an effective amount of a compound of claim 7 and at least one of the following: surfactant, solid diluent or liquid diluent.

19. An agriculturally suitable composition for controlling the growth of undesired vegetation comprising an effective amount of a compound of claim 8 and at least one of the following: surfactant, solid diluent or liquid diluent.

20. An agriculturally suitable composition for controlling the growth of undesired vegetation comprising an effective amount of a compound of claim 9 and at least one of the following: surfactant, solid diluent or liquid diluent.

21. An agriculturally suitable composition for controlling the growth of undesired vegetation comprising an effective amount of a compound of claim 11 and at least one of the following: surfactant, solid diluent or liquid diluent.

22. An agriculturally suitable composition for controlling the growth of undesired vegetation comprising an effective amount of a compound of claim 12 and at least one of the following: surfactant, solid diluent or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

27. A method for controlling the growth of undesired vegetation which comprises applying to the locus to be protected an effective amount of a compound in claim 5.

28. A method for controlling the growth of undesired vegetation which comprises applying to the locus to be protected an effective amount of a compound of claim 6.

29. A method for controlling the growth of undesired vegetation which comprises applying to the locus to be protected an effective amount of a compound of claim 7.

30. A method for controlling the growth of undesired vegetation which comprises applying to the locus to be protected an effective amount of a compound of claim 8.

31. A method for controlling the growth of undesired vegetation which comprises applying to the locus to be protected an effective amount of a compound of claim 9.

32. A method for controlling the growth of undesired vegetation which comprises applying to the locus to be protected an effective amount of a compound of claim 11.

33. A method for controlling the growth of undesired vegetation which comprises applying to the locus to be protected an effective amount of a compound of claim 12.

* * * * *